(12) United States Patent
Lewis et al.

(10) Patent No.: US 11,690,850 B2
(45) Date of Patent: Jul. 4, 2023

(54) INHIBITORS OF RECEPTOR INTERACTING PROTEIN KINASE I FOR THE TREATMENT OF DISEASE

(71) Applicant: Board of Regents, The University of Texas System, Austin, TX (US)

(72) Inventors: Richard T. Lewis, Missouri City, TX (US); Matthew Hamilton, Missouri City, TX (US); William J. Ray, Houston, TX (US); Fernando Alvarez, Austin, TX (US); Naphtali Reyna, Arlington, TX (US); Jason Cross, Pearland, TX (US); Suyambu Kesava Vijayan Ramaswamy, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 138 days.

(21) Appl. No.: 16/952,422

(22) Filed: Nov. 19, 2020

(65) Prior Publication Data

US 2021/0154204 A1  May 27, 2021

Related U.S. Application Data

(60) Provisional application No. 62/940,428, filed on Nov. 26, 2019.

(51) Int. Cl.
| | |
|---|---|
| *A61K 31/553* | (2006.01) |
| *A61K 31/551* | (2006.01) |
| *C07D 237/24* | (2006.01) |
| *C07D 401/12* | (2006.01) |
| *C07D 471/04* | (2006.01) |
| *C07D 417/12* | (2006.01) |
| *C07D 403/12* | (2006.01) |
| *C07D 413/12* | (2006.01) |
| *C07D 409/12* | (2006.01) |
| *C07D 498/04* | (2006.01) |
| *C07D 487/04* | (2006.01) |
| *C07D 413/14* | (2006.01) |
| *C07D 401/14* | (2006.01) |
| *C07D 491/107* | (2006.01) |
| *A61P 35/00* | (2006.01) |
| *A61K 31/50* | (2006.01) |
| *A61K 31/501* | (2006.01) |
| *A61K 31/506* | (2006.01) |
| *A61K 31/55* | (2006.01) |
| *A61K 45/06* | (2006.01) |

(52) U.S. Cl.
CPC ............ *A61K 31/553* (2013.01); *A61K 31/50* (2013.01); *A61K 31/501* (2013.01); *A61K 31/506* (2013.01); *A61K 31/55* (2013.01); *A61K 31/551* (2013.01); *A61K 45/06* (2013.01); *A61P 35/00* (2018.01); *C07D 237/24* (2013.01); *C07D 401/12* (2013.01); *C07D 401/14* (2013.01); *C07D 403/12* (2013.01); *C07D 409/12* (2013.01); *C07D 413/12* (2013.01); *C07D 413/14* (2013.01); *C07D 417/12* (2013.01); *C07D 471/04* (2013.01); *C07D 487/04* (2013.01); *C07D 491/107* (2013.01); *C07D 498/04* (2013.01)

(58) Field of Classification Search
CPC .. C07D 401/12; C07D 401/14; C07D 403/12; C07D 409/12; C07D 413/12; C07D 413/14; C07D 417/12; C07D 471/04; C07D 487/04; C07D 491/107; C07D 498/04; C07D 237/24
See application file for complete search history.

(56) References Cited

U.S. PATENT DOCUMENTS

| | | | |
|---|---|---|---|
| 6,291,476 B1 | 9/2001 | Kordik | |
| 2012/0122889 A1 | 5/2012 | Yuan | |
| 2013/0184287 A1 | 7/2013 | Gray | |
| 2013/0281428 A1* | 10/2013 | Ohki | C07D 451/02 546/261 |
| 2014/0066466 A1 | 3/2014 | Yuan | |
| 2014/0228367 A1 | 8/2014 | Flynn | |
| 2014/0364431 A1* | 12/2014 | Gong | A61K 31/506 544/235 |
| 2015/0353533 A1* | 12/2015 | Bandyopadhyay | A61P 1/04 514/212.07 |
| 2016/0002255 A1 | 1/2016 | Brockunier | |
| 2016/0075654 A1 | 3/2016 | Bunker | |
| 2016/0221963 A1 | 8/2016 | Beigelman | |
| 2017/0008877 A1* | 1/2017 | Patel | A61P 9/10 |
| 2017/0226127 A1* | 8/2017 | Estrada | A61P 23/00 |

(Continued)

FOREIGN PATENT DOCUMENTS

| | | |
|---|---|---|
| WO | 2010075561 | 7/2010 |
| WO | 2010122088 | 10/2010 |

(Continued)

OTHER PUBLICATIONS

Ameriks; Bioorg. Med. Chem. Lett. 20 (2010) 4060-4064. doi:10.1016/j.bmcl.2010.05.086 (Year: 2010).*

(Continued)

*Primary Examiner* — Daniel R Carcanague

(74) *Attorney, Agent, or Firm* — Cynthia Hathaway; Lauren L. Stevens; Erik M. Larsen

(57) ABSTRACT

Disclosed herein are compounds which inhibit RIPK1, pharmaceutical compositions, and methods of treatment of RIPK1-mediated diseases, such as neurodegenerative disorders, inflammatory disorders, and cancer.

24 Claims, No Drawings

(56) References Cited

U.S. PATENT DOCUMENTS

| | | | |
|---|---|---|---|
| 2017/0266199 A1* | 9/2017 | Berger | A61K 31/55 |
| 2018/0170927 A1 | 6/2018 | Patel | |
| 2018/0319819 A1 | 11/2018 | Yogo | |
| 2019/0092714 A1 | 3/2019 | Suzuki | |
| 2019/0241565 A1* | 8/2019 | Patel | A61P 1/18 |
| 2020/0062735 A1* | 2/2020 | Anbari | A61P 35/00 |
| 2021/0032271 A1* | 2/2021 | Patel | C07D 519/00 |
| 2021/0094921 A1 | 4/2021 | Lewis | |
| 2021/0094951 A1 | 4/2021 | Lewis | |
| 2021/0115010 A1 | 4/2021 | Soth | |

FOREIGN PATENT DOCUMENTS

| | | | |
|---|---|---|---|
| WO | 2011115725 | 9/2011 | |
| WO | 2012125544 | 9/2012 | |
| WO | 2014125444 | 8/2014 | |
| WO | 2016027253 | 2/2016 | |
| WO | 2016044331 | 3/2016 | |
| WO | 2016101887 | 6/2016 | |
| WO | 2016185423 | 11/2016 | |
| WO | 2017069279 | 4/2017 | |
| WO | 2017096301 | 6/2017 | |
| WO | 2017136727 | 8/2017 | |
| WO | 2018100070 | 6/2018 | |
| WO | 2018107060 | 6/2018 | |
| WO | 2019051038 | 3/2019 | |
| WO | 2019110832 | 6/2019 | |
| WO | WO-2019213445 A1 * | 11/2019 | A61K 31/553 |
| WO | WO-2019213447 A1 * | 11/2019 | A61K 31/553 |
| WO | 2021046515 | 3/2021 | |
| WO | 2021062199 | 3/2021 | |
| WO | 2021108198 | 6/2021 | |
| WO | WO-2021173917 A1 * | 9/2021 | |

OTHER PUBLICATIONS

Degterev; PNAS 2019, 116, 9714-9722. https://doi.org/10.1073/pnas.1901179116 (Year: 2019).*
Chemical Abstracts STN Database, Record for RN 924068-54-2, "N-(3-Chlorophenyl)-1,4-dihydro-6-methyl-4-oxo-1-phenyl-3-pyridazinecarboxamide", Entered STN Mar. 1, 2007. (Year: 2007).*
Chemical Abstracts STN Database, Record for RN 1277246-48-6, "1-(2-Fluorophenyl)-N-(hexahydro-2-oxo-1H-azepin-3-yl)-1,4-dihydro-6-methyl-4-oxo-3-pyridazinecarboxamide", Entered STN Apr. 11, 2011. (Year: 2011).*
Berger, S. et al., "Characterization of GSK'963: A Structurally Distinct, Potent and Selective Inhibitor of RIP1 Kinase", Cell Death Discov., 1:15009, (2015).
Choi, S. et al., "Optimization of Tricyclic Nec-3 Necroptosis Inhibitors for In Vitro Liver Microsomal Stability", Bioorg Med Chem Lett., 22(17):5685-8, (2012).
Harris, P. et al., "Identification of a RIP1 Kinase Inhibitor Clinical Candidate (GSK3145095) for the Treatment of Pancreatic Cancer", ACS Med Chem Lett., 10(6):857-62, (2019).
Jagtap, P. et al., "Structure-Activity Relationship Study of Tricyclic Necroptosis Inhibitors", J Med Chem., 50(8):1886-95, (2007).
Ren, Y. et al., "Discovery of a Highly Potent, Selective, and Metabolically Stable Inhibitor of Receptor-Interacting Protein 1 (RIP1) for the Treatment of Systemic Inflammatory Response Syndrome", J Med Chem., 60(3):972-86, (2017).
U.S. Appl. No. 17/014,184; Application as filed, filed Sep. 8, 2020; 245 pages.
U.S. Appl. No. 17/033,104; Application as filed, filed Sep. 25, 2020; 295 pages.
Yoshikawa, M. et al., "Discovery of 7-Oxo-2,4,5,7-tetrahydro-6 H-pyrazolo[3,4-c]pyridine Derivatives as Potent, Orally Available, and Brain-Penetrating Receptor Interacting Protein 1 (RIP1) Kinase Inhibitors: Analysis of Structure-Kinetic Relationships", J Med Chem., 61(6):2384-409, (2018).
International Application No. PCT/US2020/049667; International Preliminary Report on Patentability, dated Mar. 17, 2022; 8 pages.
International Application No. PCT/US2020/049667; International Search Report and Written Opinion of the International Searching Authority, dated Feb. 4, 2021; 11 pages.
International Application No. PCT/US2020/052789; International Preliminary Report on Patentability, dated Apr. 7, 2022; 7 pages.
International Application No. PCT/US2020/052789; International Search Report and Written Opinion of the International Searching Authority, dated Feb. 17, 2021; 10 pages.
International Application No. PCT/US2020/061171; International Preliminary Report on Patentability, dated Jun. 9, 2022; 6 pages.
International Application No. PCT/US2020/061171; International Search Report and Written Opinion of the International Searching Authority, dated Mar. 17, 2021; 9 pages.
PubChem CID 122183864 Create Date: Oct. 26, 2016 (Oct. 26, 2016), especially p. 2 formula.
PubChem CID 1481295, N-Methyl-4-oxo-1-phenyl-1,4-dihydro-3-pyridazinecarboxamide, create date Jul. 11, 2005.
PubChem CID 58072278, 1-Methyl-4-oxopyridazine-3-carboxamide, create date Aug. 19, 2012.
PubChem CID 891989 Create Date: Jul. 9, 2005 (Jul. 9, 2005), especially p. 2 formula.
PubChem Compound Record for CID 132165444, CN(C(=O)C12CC(C1)(C2)C(=O)O)C, Create Date: Jan. 29, 2018.
PubChem Compound Record for CID 86010391, 3-Methylbicyclo[1.1.1]pentane-1-carboxamide, Create Date: Nov. 3, 2014.
Chemical Abstracts STN Registry Database, record for RN 2323881-41-8, "[3-(4-Cyclopropyl-1 H-1,2,3-triazol-1-yl)-1-pyrrolidinyl][3-(trifluoromethyl)bicyclo[1.1.1]pent-1-yl]methanone", Entered STN Jun. 4, 2019, (2019).
Chemical Abstracts STN Registry Database, record for RN 2373678-19-2, "3-[[2-(3-Methoxyphenyl)-1-pyrrolidinyl]carbonyl] bicyclo[1.1.1]pentane-1-carboxylic acid", Entered STN Sep. 4, 2019, (2019).
U.S. Appl. No. 17/014,184, Non-Final Office Action, dated Sep. 27, 2022; 31 pages.
U.S. Appl. No. 17/033,104, Non-Final Office Action, dated Oct. 27, 2022; 24 pages.

* cited by examiner

INHIBITORS OF RECEPTOR INTERACTING PROTEIN KINASE I FOR THE TREATMENT OF DISEASE

This application claims priority to, and the benefit of, U.S. Application No. 62/940,428, filed Nov. 26, 2019, the entirety of which is incorporated by reference herein.

Disclosed herein are new compounds and compositions and their application as pharmaceuticals for the treatment of disease. Methods of inhibition of RIPK1 in a human or animal subject are also provided for the treatment of diseases mediated by RIPK1 such as neurodegenerative disorders, inflammatory disorders, and cancer.

The role of Receptor Interacting Protein Kinase 1 (RIPK1) in the regulation of apoptotic or necroptotic cell death pathways has been reported, and its emerging role in the mediation coordinating the response to pro-inflammatory signaling in a number of cell types and contexts is emerging. RIPK1 consists of an N-terminal kinase domain, a RHIM (RIP homotypic interaction motif) domain, and a death domain, which collectively undergo extensive post-translational modification in response to signaling through various receptors such as tumor necrosis factor α receptors (TNFRs), toll-like receptors, NOD-like receptor, and others. RIPK1 has been most extensively studied in the context of TNFR1 signaling, which triggers its recruitment to the C-terminal domain of the receptor via the protein TRADD (TNF receptor associated death domain protein). There RIPK1 is ubiquitinated by the E3 ubiquitin ligases TNF receptor-associated factor 2 (TRAF2) or TRAF5 and the cellular inhibitor of apoptosis proteins (cIAPs) cIAP1 and cIAP2. This molecular assembly is known as complex 1. Cylindromatosis (CYLD) then mediates the deubiquitination of RIPK1 to allow assembly of complex IIb, also known as the necrosome. The necrosome consists of the RIPK1 homolog RIPK3 and the pseudokinase MLKL. The assembly and function of the necrosome is inhibited by caspase 8 such that only when caspase 8 activity is blocked is the necrosome functional. In that context the necrosome causes necroptosis, an inflammatory form of programmed cell death in which membrane lysis causes the release of cellular contents into the extracellular space.

RIPK1 can also, in different contexts, regulate apoptosis and inflammation. When cIAPs are inhibited so that RIPK1 ubiquitination does not occur, RIPK1 participates in apoptosis. Ubiquitinated RIPK1 can also recruit NF-κB essential modulator (NEMO) and TAK1 binding protein 2 or 3 (TAB2/3), leading to activation of inhibitor of kappa B (IKB) kinase beta (IKK) and transforming growth factor beta (TGF)-activated kinase 1 (TAK1), which in turn promotes the NF-κB pro-inflammatory or pro-survival gene expression programs. Given its role in inflammation, RIPK1 has been implicated in many diseases featuring chronic and acute inflammatory signaling, including viral infections, sepsis, retinal degeneration, traumatic brain injury, ischemic stroke, intracerebral hemorrhage, amyotrophic lateral sclerosis, acute kidney injury, myocardial reperfusion injury, Alzheimer's disease, ulcerative colitis, osteoarthritis, and others. In animal models of these diseases, RIPK1 kinase inhibitors such as necrostatin-1 have shown to be effective, leading to the development of such molecules for clinical trials in a number of indications.

DETAILED DESCRIPTION

Provided is a compound of structural Formula (I):

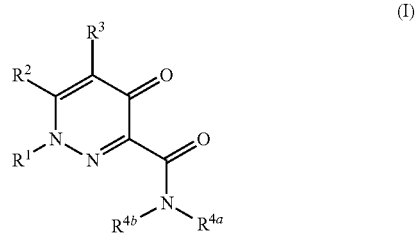

or a salt thereof, wherein:
$R^1$ is chosen from alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^5$;
$R^2$ is chosen from H, alkyl, haloalkyl, and (alkoxy)alkyl;
$R^3$ is chosen from H, CN, halo, alkyl, and alkoxy;
or $R^2$ and $R^3$, together with the intervening atoms, combine to form a 5-, 6-, or 7-membered cycloalkyl, heterocycloalkyl, aryl, or heteroaryl;
$R^{4a}$ and $R^{4b}$ are independently chosen from H, alkyl, cycloalkyl, heterocycloalkyl, aryl, heteroaryl, (alkenyl)alkyl, (alkynyl)alkyl, (cycloalkyl)alkyl, (heterocycloalkyl)alkyl, (aryl)alkyl, (heteroaryl)alkyl, (cycloalkyl)(aryl)alkyl, and (cycloalkyl)(heteroaryl)alkyl, any one of which is optionally substituted with one or more $R^6$,
or $R^{4a}$ and $R^{4b}$, together with the intervening nitrogen, combine to form heterocycloalkyl, which is optionally substituted with one or more $R^6$;
each $R^5$ is independently chosen from CN, halo, hydroxy, oxo, alkyl, and (alkyl)oxy; and
each $R^6$ is independently chosen from CN, halo, hydroxy, oxo, alkyl, haloalkyl, cycloalkyl, heterocycloalkyl, aryl, heteroaryl, (alkenyl)alkyl, (alkynyl)alkyl, (cycloalkyl)alkyl, (heterocycloalkyl)alkyl, (aryl)alkyl, (heteroaryl)alkyl, (alkyl)oxy, (cycloalkyl)oxy, (heterocycloalkyl)oxy, (aryl)oxy, (heteroaryl)oxy, (alkyl)NH, (cycloalkyl)NH, (heterocycloalkyl)NH, (aryl)NH, (heteroaryl)NH, (alkyl)(alkyl)N, (cycloalkyl)(alkyl)N, (heterocycloalkyl)(alkyl)N, (aryl)(alkyl)N, and (heteroaryl)(alkyl)N.

Also provided herein is a compound of structural Formula (II):

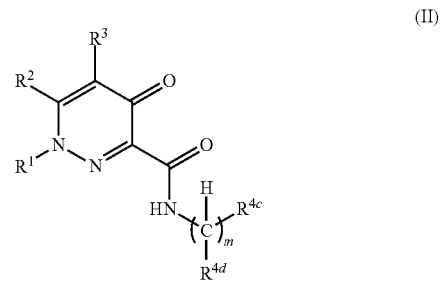

or a salt thereof, wherein:
m is chosen from 0, 1, and 2;
$R^1$ is chosen from alkyl, cycloalkyl, heterocycloalkyl, aryl, heteroaryl, (cycloalkyl)alkyl, (heterocycloalkyl)

alkyl, (aryl)alkyl, and (heteroaryl)alkyl, any one of which is optionally substituted with one or more $R^5$;

$R^2$ is chosen from H, alkyl, haloalkyl, and (alkoxy)alkyl;

$R^3$ is chosen from H, CN, halo, alkyl, and alkoxy;

or $R^2$ and $R^3$, together with the intervening atoms, combine to form a 5-, 6-, or 7-membered cycloalkyl, heterocycloalkyl, aryl, or heteroaryl;

$R^{4c}$ is chosen from alkyl, alkenyl, alkynyl, cycloalkyl, heterocycloalkyl, aryl, and heteroaryl, any one of which is optionally substituted with one or more $R^6$;

each $R^{4d}$ is independently chosen from H and alkyl;

each $R^5$ is independently chosen from CN, halo, hydroxy, oxo, alkyl, and (alkyl)oxy; and each $R^6$ is independently chosen from CN, halo, hydroxy, oxo, alkyl, haloalkyl, cycloalkyl, heterocycloalkyl, aryl, heteroaryl, (alkenyl)alkyl, (alkynyl)alkyl, (cycloalkyl)alkyl, (heterocycloalkyl)alkyl, (aryl)alkyl, (heteroaryl)alkyl, (alkyl)oxy, (cycloalkyl)oxy, (heterocycloalkyl)oxy, (aryl)oxy, (heteroaryl)oxy, (alkyl)NH, (cycloalkyl)NH, (heterocycloalkyl)NH, (aryl)NH, (heteroaryl)NH, (alkyl)(alkyl)N, (cycloalkyl)(alkyl)N, (heterocycloalkyl)(alkyl)N, (aryl)(alkyl)N, and (heteroaryl)(alkyl)N.

Also provided herein is a compound of structural Formula (III):

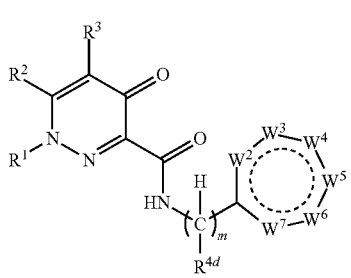

or a salt thereof, wherein:

m is chosen from 0, 1, and 2;

$R^1$ is chosen from alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^5$;

$R^2$ is chosen from H, alkyl, haloalkyl, and (alkoxy)alkyl;

$R^3$ is chosen from H, CN, halo, alkyl, and alkoxy;

or $R^2$ and $R^3$, together with the intervening atoms, combine to form a 5-, 6-, or 7-membered cycloalkyl, heterocycloalkyl, aryl, or heteroaryl;

each $R^{4d}$ is independently chosen from H and alkyl;

$W^2$ is chosen from $CHR^{6a}$, $CR^{6a}$, $NR^{6a}$, N, O, and S;

$W^3$ is chosen from $CHR^{6b}$, $CR^{6b}$, $NR^{6b}$, N, O, and S;

$W^4$ is chosen from a bond, $CHR^{6c}$, $CR^{6c}$, $NR^{6c}$, N, O, and S;

$W^5$ is chosen from $CHR^{6d}$, $CR^{6d}$, $NR^{6d}$, N, O, and S;

$W^6$ is chosen from $CHR^{6e}$, $CR^{6e}$, $NR^{6e}$, N, O, and S;

$W^7$ is chosen from $CHR^{6f}$, $CR^{6f}$, $NR^{6f}$, N, O, and S;

$W^2$, $W^3$, $W^4$, $W^5$, $W^6$, and $W^7$, together with the intervening carbon, combine to form a 6- or 7-membered cycloalkyl, heterocycloalkyl, aryl, or heteroaryl;

each $R^5$ is independently chosen from CN, halo, hydroxy, oxo, alkyl, and (alkyl)oxy; and $R^{6a}$ and $R^{6b}$ can combine, together with the intervening two atoms, to form a 5-, 6-, or 7-membered cycloalkyl, heterocycloalkyl, aryl, or heteroaryl, any one of which is optionally substituted with one or more $R^6$;

$R^{6c}$ and $R^{6d}$ can combine, together with the intervening two atoms, to form a 5-, 6-, or 7-membered cycloalkyl, heterocycloalkyl, aryl, or heteroaryl, any one of which is optionally substituted with one or more $R^6$;

$R^{6e}$ and $R^{6f}$ can combine, together with the intervening two atoms, to form a 5-, 6-, or 7-membered cycloalkyl, heterocycloalkyl, aryl, or heteroaryl, any one of which is optionally substituted with one or more $R^6$; and $R^{6a}$ and $R^{6e}$ can combine to form alkylene, which is optionally substituted with one or more $R^6$;

each of $R^{6a}$, $R^{6b}$, $R^{6c}$, $R^{6d}$, $R^{6e}$ and $R^{6f}$, unless otherwise defined, is independently chosen from H, CN, halo, hydroxy, oxo, alkyl, cycloalkyl, heterocycloalkyl, aryl, and heteroaryl; and each $R^6$ is independently chosen from CN, halo, hydroxy, oxo, alkyl, haloalkyl, cycloalkyl, heterocycloalkyl, aryl, heteroaryl, (alkenyl)alkyl, (alkynyl)alkyl, (cycloalkyl)alkyl, (heterocycloalkyl)alkyl, (aryl)alkyl, (heteroaryl)alkyl, (alkyl)oxy, (cycloalkyl)oxy, (heterocycloalkyl)oxy, (aryl)oxy, (heteroaryl)oxy, (alkyl)NH, (cycloalkyl)NH, (heterocycloalkyl)NH, (aryl)NH, (heteroaryl)NH, (alkyl)(alkyl)N, (cycloalkyl)(alkyl)N, (heterocycloalkyl)(alkyl)N, (aryl)(alkyl)N, and (heteroaryl)(alkyl)N.

Also provided herein is a compound of structural Formula (IV):

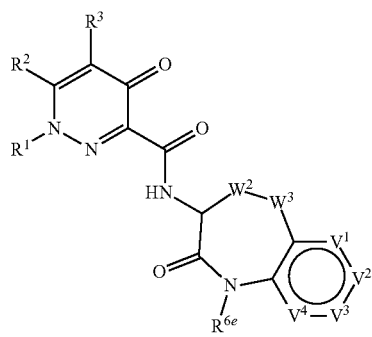

or a salt thereof, wherein:

$R^1$ is chosen from alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^5$;

$R^2$ is chosen from H, alkyl, haloalkyl, and (alkoxy)alkyl;

$R^3$ is chosen from H, CN, halo, alkyl, and alkoxy;

or $R^2$ and $R^3$, together with the intervening atoms, combine to form a 5-, 6-, or 7-membered cycloalkyl, heterocycloalkyl, aryl, or heteroaryl;

$V^1$ is chosen from a bond, $CR^{6g}$, N, $NR^{6g}$, O, and S;

$V^2$, $V^3$, and $V^4$ are independently chosen from $CR^{6g}$, N, $NR^{6g}$, O, and S;

$V^1$, $V^2$, $V^3$, and $V^4$, together with the intervening two carbons, combine to form a 5- or 6-membered aryl or heteroaryl;

$W^2$ is chosen from a bond and $CHR^{6h}$;

$W^3$ is chosen from a bond, $CHR^{6h}$, $NR^{6h}$, O, and S;

if $W^2$ is a bond, then $W^3$ is $CHR^{6h}$;

each $R^5$ is independently chosen from CN, halo, hydroxy, oxo, alkyl, and (alkyl)oxy;

$R^{6e}$ is chosen from H, alkyl, and cycloalkyl; and each $R^{6g}$ and $R^{6h}$ is independently chosen from H, CN, halo, hydroxy, oxo, alkyl, haloalkyl, cycloalkyl, heterocycloalkyl, aryl, heteroaryl, (cycloalkyl)alkyl, (heterocycloalkyl)alkyl, (aryl)alkyl, (heteroaryl)alkyl, (alkyl)oxy, (cycloalkyl)oxy, (aryl)oxy, (heteroaryl)oxy, (heterocycloalkyl)oxy, (alkyl)NH, (cycloalkyl)NH, (heterocycloalkyl)NH, (aryl)NH, (heteroaryl)NH, (alkyl)(alkyl)N, (cycloalkyl)(alkyl)N, (heterocycloalkyl)(alkyl)N, (aryl)(alkyl)N, and (heteroaryl)(alkyl)N;

or two $R^{6h}$ on adjacent atoms, together with the atoms to which they are attached, combine to form cycloalkyl or heterocycloalkyl.

Also provided herein is a compound of structural Formula (V):

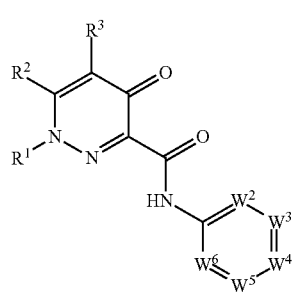

or a salt thereof, wherein:

$R^1$ is chosen from alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^5$;

$R^2$ is chosen from H and alkyl;

$R^3$ is chosen from H, CN, halo, alkyl, and alkoxy;

or $R^2$ and $R^3$, together with the intervening atoms, combine to form a 5-, 6-, or 7-membered cycloalkyl, heterocycloalkyl, aryl, or heteroaryl;

$W^2$ is chosen from $CR^{6a}$ and N;
$W^3$ is chosen from $CR^{6b}$ and N;
$W^4$ is chosen from $CR^{6c}$ and N;
$W^5$ is chosen from $CR^{6d}$ and N;
$W^6$ is chosen from $CR^{6e}$ and N;

$R^{6a}$ and $R^{6b}$, together with the intervening two carbons, can combine to form aryl or heteroaryl, either one of which is optionally substituted with one $R^6$, $R^{6b}$ and $R^{6c}$, together with the intervening two carbons, can combine to form aryl or heteroaryl, either one of which is optionally substituted with one $R^6$, $R^{6c}$ and $R^{6d}$, together with the intervening two carbons, can combine to form aryl or heteroaryl, either one of which is optionally substituted with one $R^6$;

$R^{6d}$ and $R^{6e}$, together with the intervening two carbons, can combine to form aryl or heteroaryl, either one of which is optionally substituted with one $R^6$;

each $R^{6a}$, $R^{6b}$, $R^{6c}$, $R^{6d}$, and $R^{6e}$ unless otherwise defined, is independently chosen from H, CN, halo, hydroxy, alkyl, cycloalkyl, heterocycloalkyl, aryl, heteroaryl, (alkenyl)alkyl, (alkynyl)alkyl, (cycloalkyl)alkyl, (heterocycloalkyl)alkyl, (aryl)alkyl, (heteroaryl)alkyl, (alkyl)oxy, (cycloalkyl)oxy, (heterocycloalkyl)oxy, (aryl)oxy, (heteroaryl)oxy, (alkyl)NH, (cycloalkyl)NH, (heterocycloalkyl)NH, (aryl)NH, (heteroaryl)NH, (alkyl)(alkyl)N, (cycloalkyl)(alkyl)N, (heterocycloalkyl)(alkyl)N, (aryl)(alkyl)N, and (heteroaryl)(alkyl)N; and each $R^6$ is independently chosen from CN, halo, hydroxy, oxo, alkyl, haloalkyl, cycloalkyl, heterocycloalkyl, aryl, heteroaryl, (alkenyl)alkyl, (alkynyl)alkyl, (cycloalkyl)alkyl, (heterocycloalkyl)alkyl, (aryl)alkyl, (heteroaryl)alkyl, (alkyl)oxy, (cycloalkyl)oxy, (heterocycloalkyl)oxy, (aryl)oxy, (heteroaryl)oxy, (alkyl)NH, (cycloalkyl)NH, (heterocycloalkyl)NH, (aryl)NH, (heteroaryl)NH, (alkyl)(alkyl)N, (cycloalkyl)(alkyl)N, (heterocycloalkyl)(alkyl)N, (aryl)(alkyl)N, and (heteroaryl)(alkyl)N.

In some embodiments, $R^1$ is chosen from $C_{1-6}$alkyl, $C_{3-7}$cycloalkyl, 3- to 7-membered heterocycloalkyl, $C_{6-14}$aryl, 5- to 14-membered heteroaryl, ($C_{2-6}$alkenyl)$C_{1-6}$alkyl, ($C_{2-6}$alkynyl)$C_{1-6}$ alkyl, ($C_{3-7}$cycloalkyl)$C_{1-6}$alkyl, (3- to 7-membered heterocycloalkyl)$C_{1-6}$alkyl, ($C_{6-14}$aryl)$C_{1-6}$alkyl, and (5- to 14-membered heteroaryl)$C_{1-6}$alkyl, any one of which is optionally substituted with one or more $R^5$.

In some embodiments, $R^1$ is chosen from $C_{1-6}$alkyl, $C_{3-7}$cycloalkyl, 3- to 7-membered heterocycloalkyl, $C_{6-14}$aryl, 5- to 14-membered heteroaryl, ($C_{2-6}$alkenyl)methyl, ($C_{2-6}$alkynyl)methyl, ($C_{3-7}$cycloalkyl)methyl, (3- to 7-membered heterocycloalkyl)methyl, ($C_{6-14}$aryl)methyl, and (5- to 14-membered heteroaryl)methyl, any one of which is optionally substituted with one or more $R^5$.

In some embodiments, $R^1$ is chosen from phenyl, pyridyl, pyridazinyl, pyrimidinyl, pyrazinyl, (phenyl)methyl, (pyridyl)methyl, (pyridazinyl)methyl, (pyrimidinyl)methyl, and (pyrazinyl)methyl, any one of which is optionally substituted with one or more $R^5$.

In some embodiments, $R^1$ is chosen from phenyl, pyridyl, pyridazinyl, pyrimidinyl, and pyrazinyl, any one of which is optionally substituted with one or more $R^5$.

In some embodiments, $R^1$ is chosen from phenyl, pyridyl, (phenyl)methyl, and (pyridyl)methyl, any one of which is optionally substituted with one or more $R^5$.

In some embodiments, $R^1$ is chosen from phenyl and pyridyl, any one of which is optionally substituted with one or more $R^5$.

In some embodiments, $R^1$ is phenyl, and is optionally substituted with one or more $R^5$.

In some embodiments, $R^1$ is chosen from $C_{1-6}$alkyl, $C_{3-7}$cycloalkyl, and 3- to 7-membered heterocycloalkyl, and is optionally substituted with one or more $R^5$.

In some embodiments, $R^1$ is $C_{1-6}$alkyl, and is optionally substituted with one or more $R^5$.

In some embodiments, $R^1$ is optionally substituted with 1, 2, or 3 $R^5$.

In some embodiments, $R^1$ is optionally substituted with 1 or 2 $R^5$.

In some embodiments, $R^1$ is optionally substituted with 1 $R^5$.

In some embodiments, $R^1$ is substituted with 1 $R^5$.

In some embodiments, $R^1$ is unsubstituted with an $R^5$.

In some embodiments, $R^1$ is chosen from $C_{1-4}$ alkyl and halo$C_{1-4}$ alkyl.

In some embodiments, $R^1$ is chosen from $C_{1-4}$ alkyl and fluoro$C_{1-4}$ alkyl.

In some embodiments, $R^1$ is chosen from —CHF$_2$, —CF$_3$, —CH$_2$CF$_3$, and —CH$_2$CF$_2$CF$_3$.

In some embodiments, $R^1$ is chosen from:

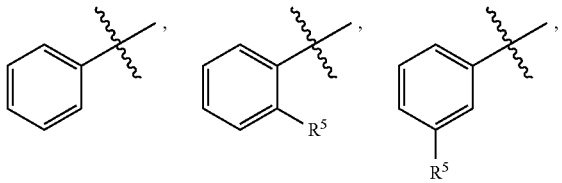

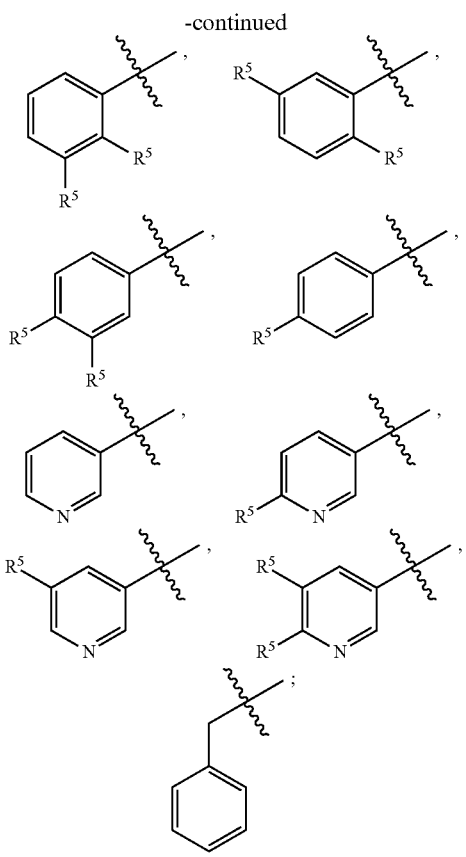

and each $R^5$ is independently chosen from F, Cl, CN, $CH_3$, and $OCH_3$.

In some embodiments, $R^2$ is chosen from alkyl and (alkoxy)alkyl.

In some embodiments, $R^2$ is chosen from methyl, ethyl, chloromethyl, bromomethyl, 2-chloroethyl, 2-bromoethyl, (methoxy)methyl, (ethoxy)methyl, 2-(methoxy)ethyl, and 2-(ethoxy)ethyl.

In some embodiments, $R^2$ is chosen from methyl, chloromethyl, bromomethyl, and (methoxy)methyl.

In some embodiments, $R^2$ is methyl.

In some embodiments, $R^3$ is chosen from H, CN, halo, and alkyl.

In some embodiments, $R^3$ is chosen from H, CN, and halo.

In some embodiments, $R^3$ is chosen from H, CN, F, Cl, and Br.

In some embodiments, $R^3$ is chosen from H, CN, Cl, and Br.

In some embodiments, $R^3$ is chosen from H, Cl, and Br.

In some embodiments, $R^3$ is H.

In some embodiments, $R^2$ and $R^3$, together with the intervening atoms, combine to form a 5-, 6-, or 7-membered cycloalkyl, heterocycloalkyl, aryl, or heteroaryl.

In some embodiments, $R^{4a}$ is H.

In some embodiments, $R^{4b}$ is chosen from $C_{1-6}$alkyl, $C_{3-7}$cycloalkyl, 4- to 11-membered heterocycloalkyl, $C_{6-14}$aryl, 5- to 14-membered heteroaryl, $(C_{2-6}$alkenyl$)C_{1-6}$alkyl, $(C_{2-6}$alkynyl$)C_{1-6}$alkyl, $(C_{3-7}$cycloalkyl$)C_{1-6}$alkyl, (4- to 11-membered heterocycloalkyl$)C_{1-6}$alkyl, $(C_{6-10}$aryl$)C_{1-6}$alkyl, (5- to 14-membered heteroaryl$)C_{1-6}$alkyl, $(C_{3-7}$cycloalkyl$)(C_{6-14}$ aryl$)C_{1-6}$alkyl, and $(C_{3-7}$cycloalkyl$)($5- to 14-membered heteroaryl$)C_{1-6}$alkyl, any one of which is optionally substituted with one or more $R^6$.

In some embodiments, $R^{4b}$ is chosen from $C_{1-6}$alkyl, $C_{3-7}$cycloalkyl, 4- to 11-membered heterocycloalkyl, $C_{6-14}$ aryl, 5- to 14-membered heteroaryl, $(C_{2-6}$alkenyl)methyl, $(C_{2-6}$alkynyl)methyl, $(C_{3-7}$cycloalkyl)methyl, (4- to 11-membered heterocycloalkyl)methyl, $(C_{6-10}$aryl)methyl, (5- to 14-membered heteroaryl)methyl, $(C_{3-7}$cycloalkyl$)(C_{6-14}$ aryl)methyl, and $(C_{3-7}$cycloalkyl$)($5- to 14-membered heteroaryl)methyl, any one of which is optionally substituted with one or more $R^6$.

In some embodiments, $R^{4b}$ is chosen from $C_{1-6}$alkyl, cyclopropyl, cyclobutyl, 2,3,4,5-tetrahydro-1H-benzo[b]azepinyl, 2,3,4,5-tetrahydrobenzo[b][1,4]oxazepinyl, phenyl, pyrrolyl, imidazolyl, pyrazolyl, thiazolyl, isothiazolyl, oxazolyl, isoxazoyl, 1,2,3-oxadiazolyl, 1,2,3-thiadiazolyl, 1,2,4-oxadiazolyl, 1,2,4-thiadiazolyl, pyridinyl, pyrazinyl, pyrimidinyl, pyridazinyl, quinolinyl, isoquinolinyl, indolinyl, acridinyl, pyrazolo[1,5-a]pyridinyl, benzo[d]thiazolyl, 1H-benzo[d]imidazolyl, 1H-benzo[d][1,2,3]triazolyl, (cyclopropyl)methyl, (cyclobutyl)methyl, (2,3,4,5-tetrahydro-1H-benzo[b]azepinyl)methyl, (2,3,4,5-tetrahydrobenzo[b]-[1,4]oxazepinyl)methyl, (phenyl)methyl, (pyrrolyl)methyl, (imidazolyl)methyl, (pyrazolyl)methyl, (thiazolyl)methyl, (isothiazolyl)methyl, (oxazolyl)methyl, (isoxazoyl)methyl, (1,2,3-oxadiazolyl)methyl, (1,2,3-thiadiazolyl)methyl, (1,2,4-oxadiazolyl)methyl, (1,2,4-thiadiazolyl)methyl, (pyridinyl)methyl, (pyrazinyl)methyl, (pyrimidinyl)methyl, (pyridazinyl)-methyl, (quinolinyl)methyl, (isoquinolinyl)methyl, (indolinyl)methyl, (acridinyl)methyl, (pyrazolo[1,5-a]pyridinyl)methyl, (benzo[d]thiazolyl)methyl, 1H-benzo[d]imidazolyl, and (1H-benzo[d][1,2,3]triazolyl)methyl, any one of which is optionally substituted with one or more $R^6$.

In some embodiments, $R^{4b}$ is 4- to 11-membered heteroaryl, which is optionally substituted with one or more $R^6$. In some embodiments, $R^{4b}$ is 9- or 10-membered bicyclic heteroaryl, either one of which is optionally substituted with one or more $R^6$. In some embodiments, $R^{4b}$ is 9-membered bicyclic heteroaryl, which is optionally substituted with one or more $R^6$. In some embodiments, $R^{4b}$ is 10-membered bicyclic heteroaryl, which is optionally substituted with one or more $R^6$. In some embodiments, $R^{4b}$ is 13- or 14-membered tricyclic heteroaryl, either one of which is optionally substituted with one or more $R^6$. In some embodiments, $R^{4b}$ is 14-membered tricyclic heteroaryl, which is optionally substituted with one or more $R^6$. In some embodiments, $R^{4b}$ is 5- or 6-membered monocyclic heteroaryl, either one of which is optionally substituted with one or more $R^6$.

In some embodiments, $R^{4b}$ is 5-membered monocyclic heteroaryl which is optionally substituted with one or more $R^6$. In some embodiments, $R^{4b}$ is chosen from pyrrolyl, furyl, thienyl, pyrazolyl, imidazolyl, oxazolyl, thiazolyl, isoxazolyl, and isothiazolyl, any one of which is optionally substituted with one or more $R^6$. In some embodiments, $R^{4b}$ is chosen from thiophen-2-yl, pyrazol-4-yl, thiazol-2-yl, isoxazol-4-yl, and isothiazol-5-yl, any one of which is optionally substituted with one or more $R^6$.

In some embodiments, $R^{4b}$ is 6-membered monocyclic heteroaryl which is optionally substituted with one or more $R^6$. In some embodiments, $R^{4b}$ is chosen from pyridinyl, pyridazinyl, pyrimidinyl, and pyrazinyl, any one of which is optionally substituted with one or more $R^6$. In some embodiments, $R^{4b}$ is chosen from pyridinyl and pyrimidinyl, either one of which is optionally substituted with one or more $R^6$. In some embodiments, $R^{4b}$ is pyrimidinyl which is optionally substituted with one or more $R^6$.

In some embodiments, $R^{4b}$ is optionally substituted with one, two, or three $R^6$. In some embodiments, $R^{4b}$ is optionally substituted with one or two $R^6$. In some embodiments, $R^{4b}$ is substituted with one or two $R^6$. In some embodiments, $R^{4b}$ is substituted with two $R^6$.
In some embodiments, $R^{4b}$ is
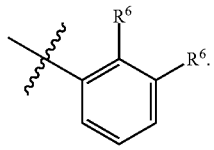
In some embodiments, $R^{4b}$ is optionally substituted with one $R^6$.
In some embodiments, $R^{4b}$ is substituted with one $R^6$.
In some embodiments, $R^{4b}$ is chosen from:
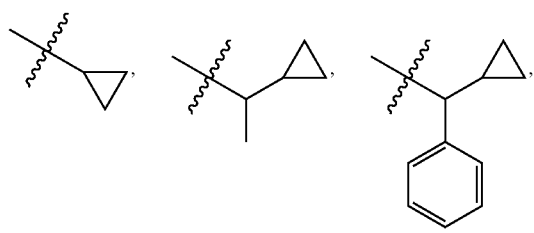
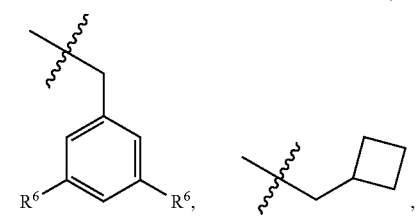
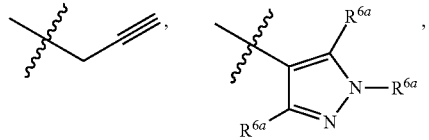
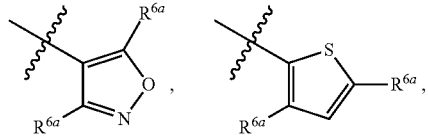
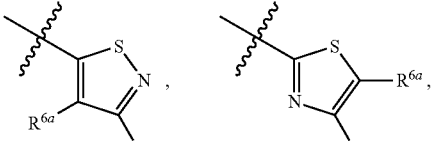
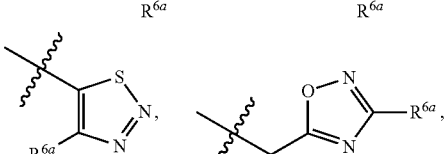
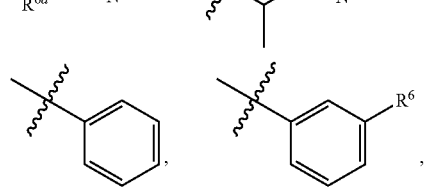
-continued
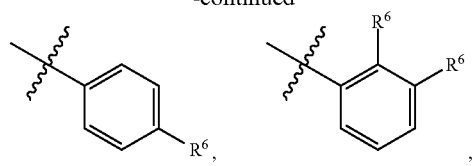
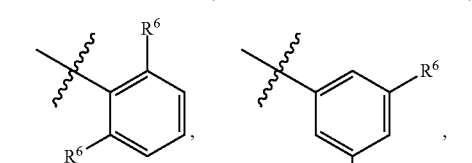
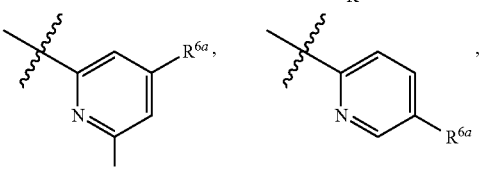
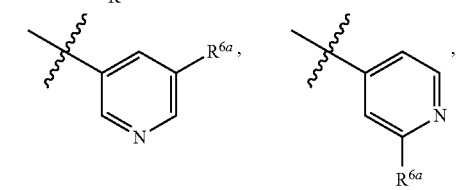
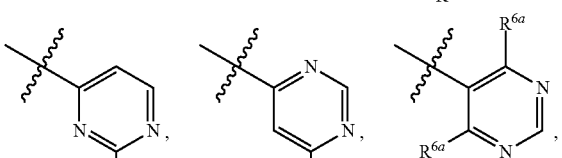
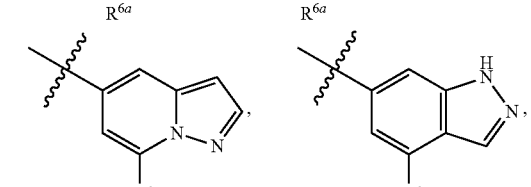
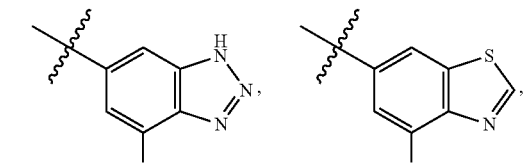
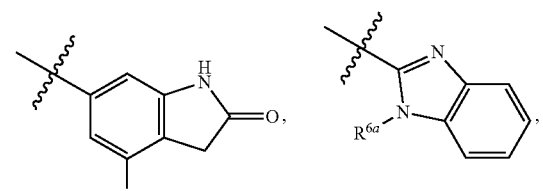
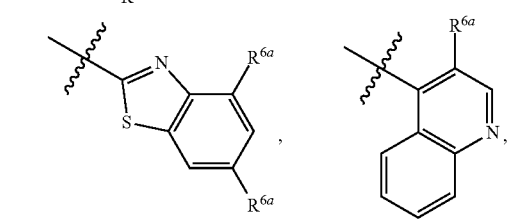

-continued

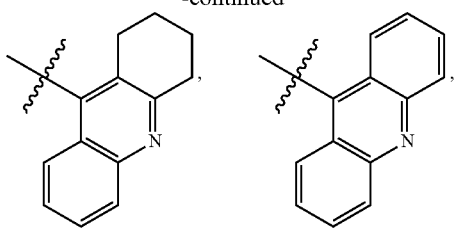

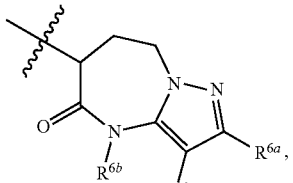

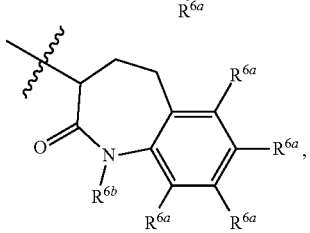

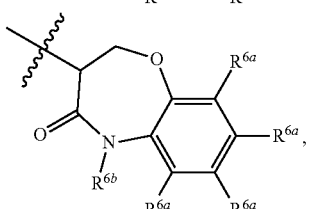

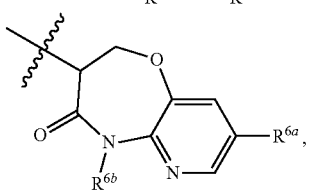

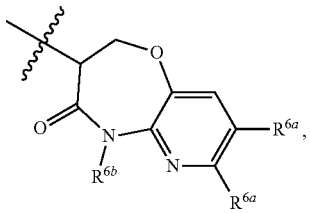

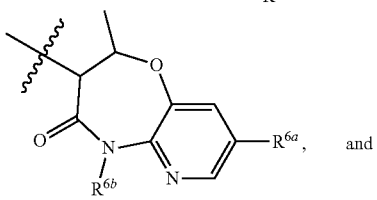, and

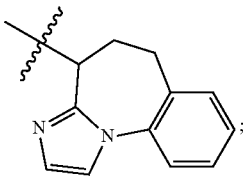;

each $R^6$ is independently chosen from CN, halo, hydroxy, oxo, $C_{1-6}$alkyl, halo$C_{1-6}$alkyl, $C_{3-7}$cycloalkyl, 4- to 11-membered heterocycloalkyl, $C_{6-10}$aryl, 5- to 10-membered heteroaryl, $(C_{2-6}$alkenyl$)C_{1-6}$alkyl, $(C_{2-6}$alkynyl$)C_{1-6}$alkyl, $(C_{3-7}$cycloalkyl$)C_{1-6}$alkyl, (4- to 11-membered heterocycloalkyl$)C_{1-6}$alkyl, $(C_{6-10}$aryl$)C_{1-6}$alkyl, (5- to 10-membered heteroaryl)$C_{1-6}$alkyl, $(C_{1-6}$alkyl)oxy, $(C_{3-7}$cycloalkyl)oxy, (4- to 11-membered heterocycloalkyl)oxy, $(C_{6-10}$aryl)oxy, (5- to 10-membered heteroaryl)oxy, $(C_{1-6}$alkyl)NH, $(C_{3-7}$cycloalkyl)NH, (4- to 11-membered heterocycloalkyl)NH, $(C_{1-6}$alkyl)$(C_{1-6}$alkyl)N, $(C_{3-7}$cycloalkyl)(alkyl)N, and (4- to 11-membered heterocycloalkyl)$(C_{1-6}$alkyl)N;

each $R^{6a}$ is independently chosen from H, CN, halo, hydroxy, oxo, $C_{1-6}$alkyl, halo$C_{1-6}$alkyl, $C_{3-7}$cycloalkyl, 4- to 11-membered heterocycloalkyl, $C_{6-10}$aryl, 5- to 10-membered heteroaryl, $(C_{2-6}$alkenyl$)C_{1-6}$alkyl, $(C_{2-6}$alkynyl$)C_{1-6}$alkyl, $(C_{3-7}$cycloalkyl$)C_{1-6}$alkyl, (4- to 11-membered heterocycloalkyl$)C_{1-6}$alkyl, $(C_{6-10}$aryl$)C_{1-6}$alkyl, (5- to 10-membered heteroaryl)$C_{1-6}$alkyl, $(C_{1-6}$alkyl)oxy, $(C_{3-7}$cycloalkyl)oxy, (4- to 11-membered heterocycloalkyl)oxy, $(C_{6-10}$aryl)oxy, (5- to 10-membered heteroaryl)oxy, $(C_{1-6}$alkyl)NH, $(C_{3-7}$cycloalkyl)NH, (4- to 11-membered heterocycloalkyl)NH, $(C_{1-6}$alkyl)$(C_{1-6}$alkyl)N, $(C_{3-7}$cycloalkyl)(alkyl)N, and (4- to 11-membered heterocycloalkyl)$(C_{1-6}$alkyl)N; and $R^{6b}$ is chosen from H and $C_{1-6}$alkyl.

In some embodiments, $R^{4b}$ is chosen from

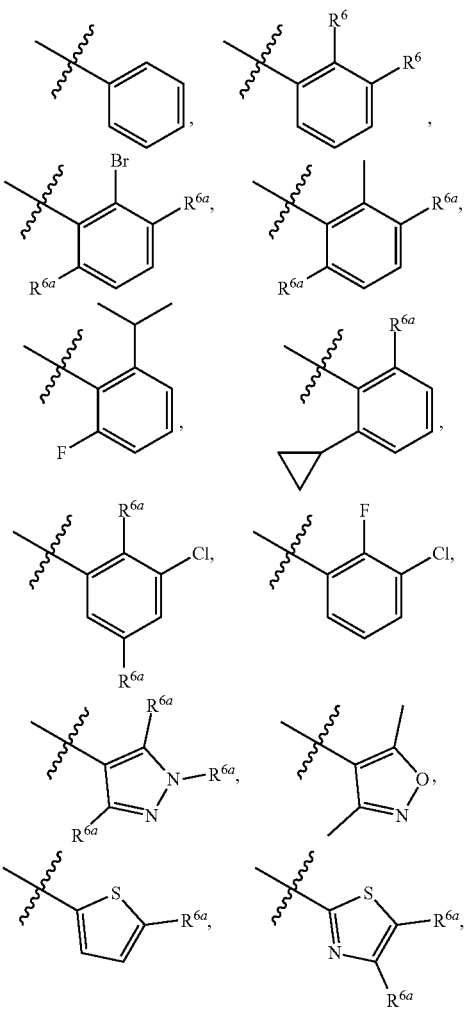

-continued
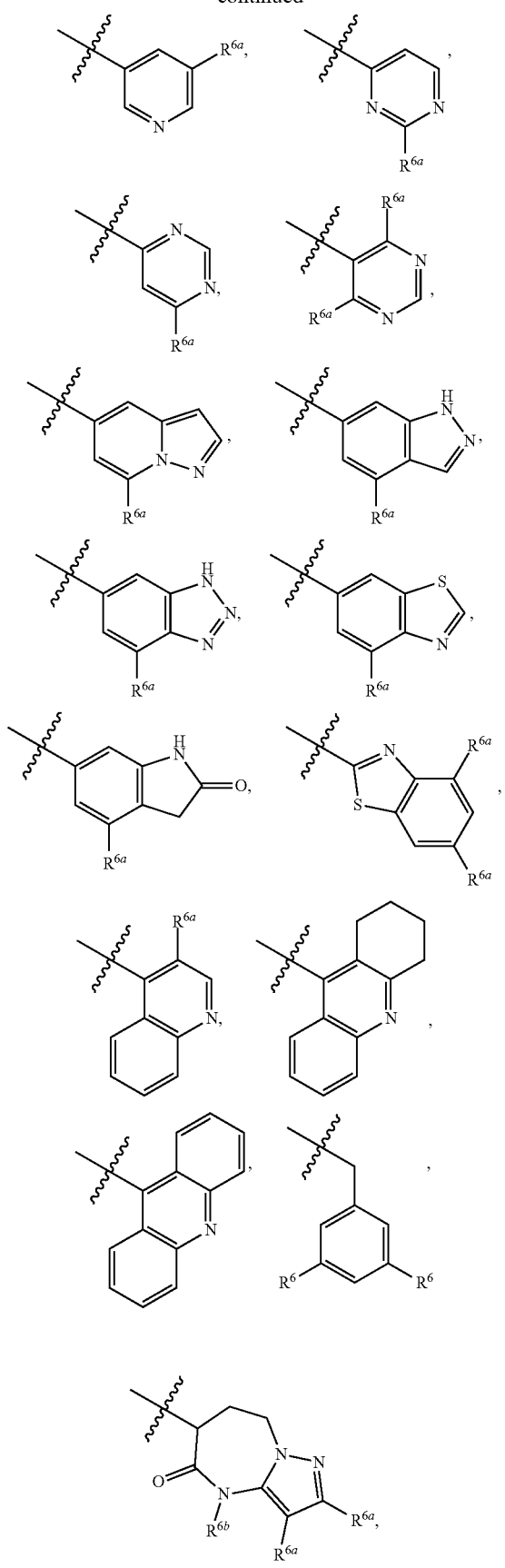
-continued
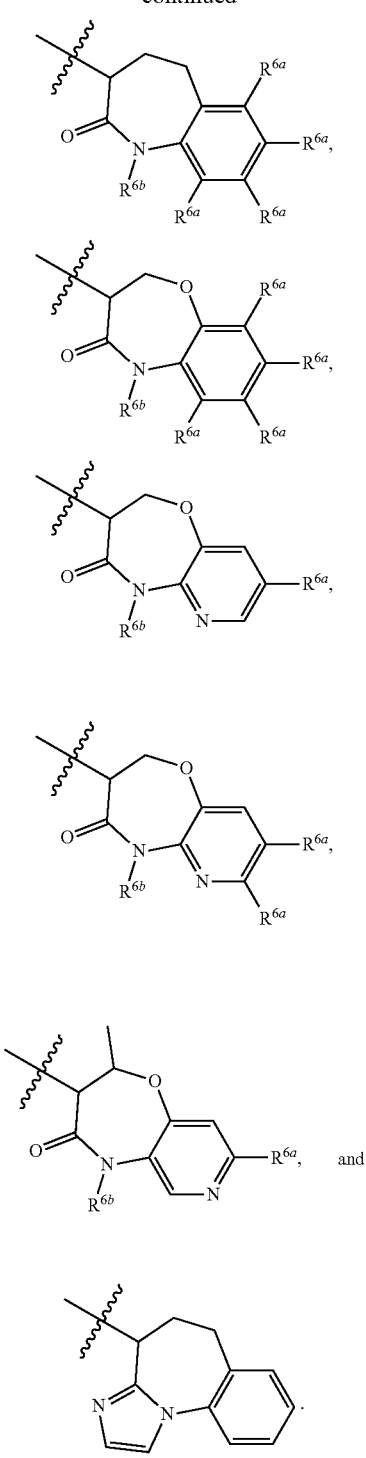
In some embodiments, $R^{4b}$ is
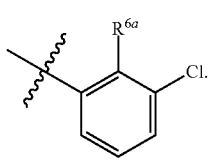

In some embodiments, $R^{4b}$ is
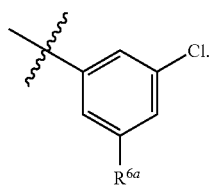
In some embodiments, $R^{4b}$ is
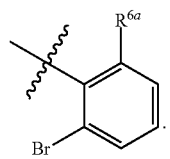
In some embodiments, $R^{4b}$ is
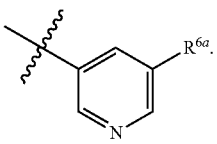
In some embodiments, $R^{4b}$ is chosen from
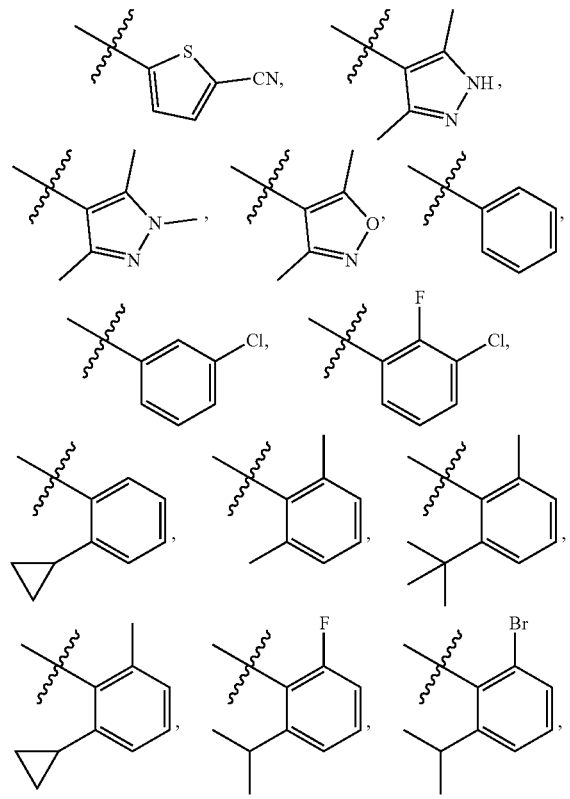
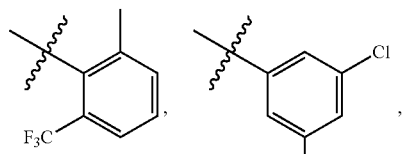
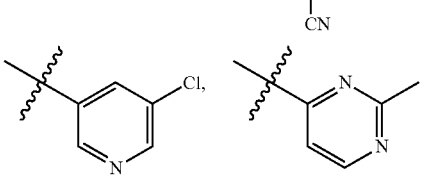
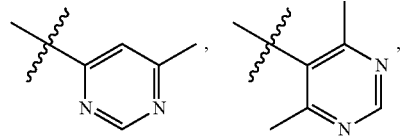
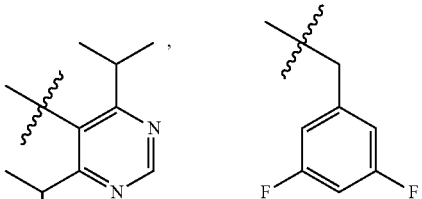
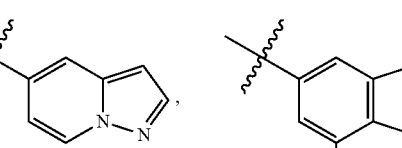
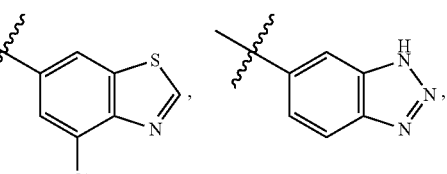
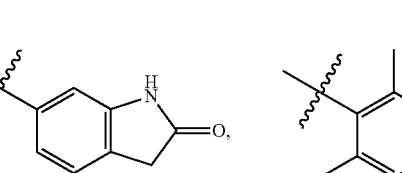

In some embodiments, $R^{4b}$ is chosen from

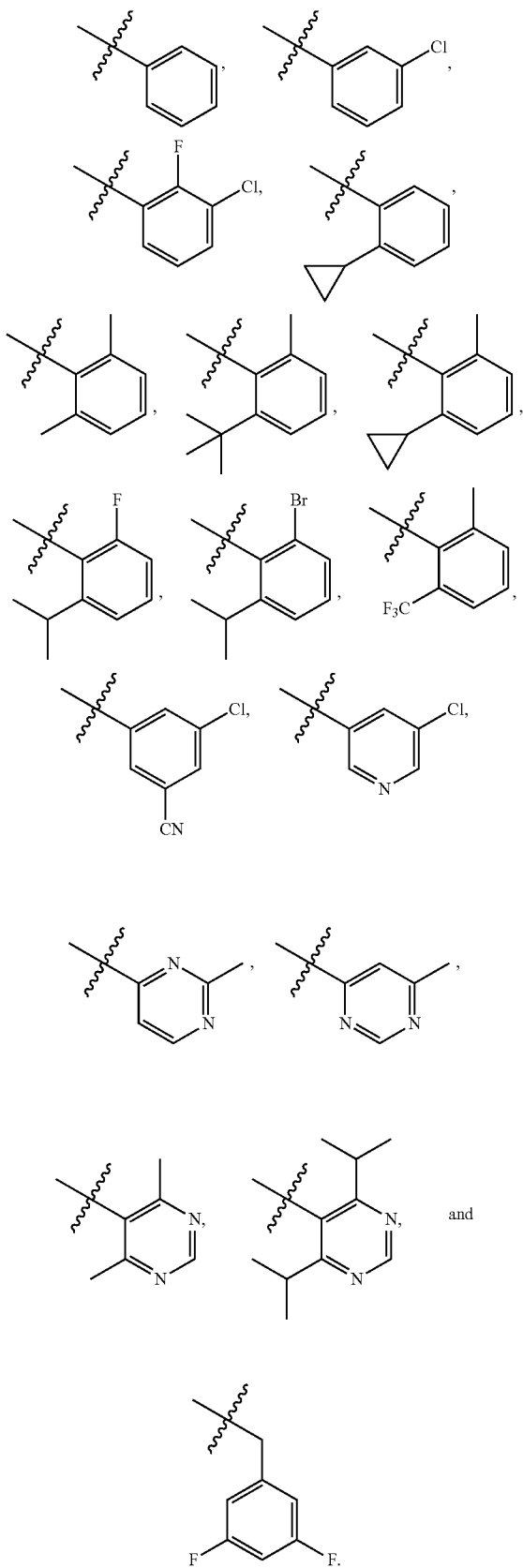

In some embodiments, $R^{4b}$ is

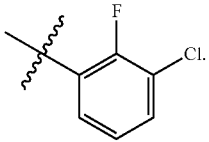 [SMILES: *c1cccc(Cl)c1F]

In some embodiments, $R^{4b}$ is unsubstituted with an $R^6$.

In some embodiments, $R^{4a}$ and $R^{4b}$, together with the intervening nitrogen, combine to form heterocycloalkyl, which is optionally substituted with one or more $R^6$.

In some embodiments, $R^{4a}$ and $R^{4b}$, together with the intervening nitrogen, combine to form pyrrolidinyl or piperidinyl, either one of which is optionally substituted with one or more $R^6$.

In some embodiments, $R^{4a}$ and $R^{4b}$, together with the intervening nitrogen, combine to form pyrrolidinyl, which is optionally substituted with one or more $R^6$.

In some embodiments, the heterocycloalkyl formed by the combination of $R^{4a}$ and $R^{4b}$ is optionally substituted with one or two $R^6$.

In some embodiments, the heterocycloalkyl formed by the combination of $R^{4a}$ and $R^{4b}$ is optionally substituted with one $R^6$.

In some embodiments, the heterocycloalkyl formed by the combination of $R^{4a}$ and $R^{4b}$ is substituted with one $R^6$.

In some embodiments, the heterocycloalkyl formed by the combination of $R^{4a}$ and $R^{4b}$ is unsubstituted with an $R^6$.

In some embodiments, m is chosen from 0 and 1.

In some embodiments, m is 0.

In some embodiments, m is 1.

In some embodiments, $R^{4c}$ is chosen from $C_{1-6}$alkyl, $C_{3-7}$cycloalkyl, 4- to 11-membered heterocycloalkyl, $C_{6-14}$aryl, 5- to 14-membered heteroaryl, $C_{2-6}$alkenyl, and $C_{2-6}$alkynyl, any one of which is optionally substituted with one or more $R^6$.

In some embodiments, $R^{4c}$ is chosen from $C_{1-6}$alkyl, $C_{2-6}$alkenyl, $C_{2-6}$alkynyl, cyclopropyl, cyclobutyl, 2,3,4,5-tetrahydro-1H-benzo[b]azepinyl, 2,3,4,5-tetrahydrobenzo[b][1,4]oxazepinyl, phenyl, pyrrolyl, imidazolyl, pyrazolyl, thiazolyl, isothiazolyl, oxazolyl, isoxazoyl, 1,2,3-oxadiazolyl, 1,2,3-thiadiazolyl, 1,2,4-oxadiazolyl, 1,2,4-thiadiazolyl, pyridinyl, pyrazinyl, pyrimidinyl, pyridazinyl, quinolinyl, isoquinolinyl, indolinyl, acridinyl, pyrazolo[1,5-a]pyridinyl, benzo[d]thiazolyl, 1H-benzo[d]imidazolyl, and 1H-benzo[d][1,2,3]-triazolyl, any one of which is optionally substituted with one or more $R^6$.

In some embodiments, $R^{4c}$ is chosen from 2,3,4,5-tetrahydro-1H-benzo[b]azepinyl, 2,3,4,5-tetrahydrobenzo[b][1,4]oxazepinyl, phenyl, pyrrolyl, imidazolyl, pyrazolyl, thiazolyl, isothiazolyl, oxazolyl, isoxazoyl, 1,2,3-oxadiazolyl, 1,2,3-thiadiazolyl, 1,2,4-oxadiazolyl, 1,2,4-thiadiazolyl, pyridinyl, pyrazinyl, pyrimidinyl, pyridazinyl, quinolinyl, isoquinolinyl, indolinyl, acridinyl, pyrazolo[1,5-a]pyridinyl, benzo[d]thiazolyl, 1H-benzo[d]imidazolyl, and 1H-benzo[d][1,2,3]triazolyl, any one of which is optionally substituted with one or more $R^6$.

In some embodiments, $R^{4c}$ is chosen from $C_{1-6}$alkyl, $C_{3-7}$cycloalkyl, 4- to 11-membered heterocycloalkyl, $C_{6-14}$aryl, and 5- to 14-membered heteroaryl, any one of which is optionally substituted with one or more $R^6$.

In some embodiments, $R^{4c}$ is chosen from:
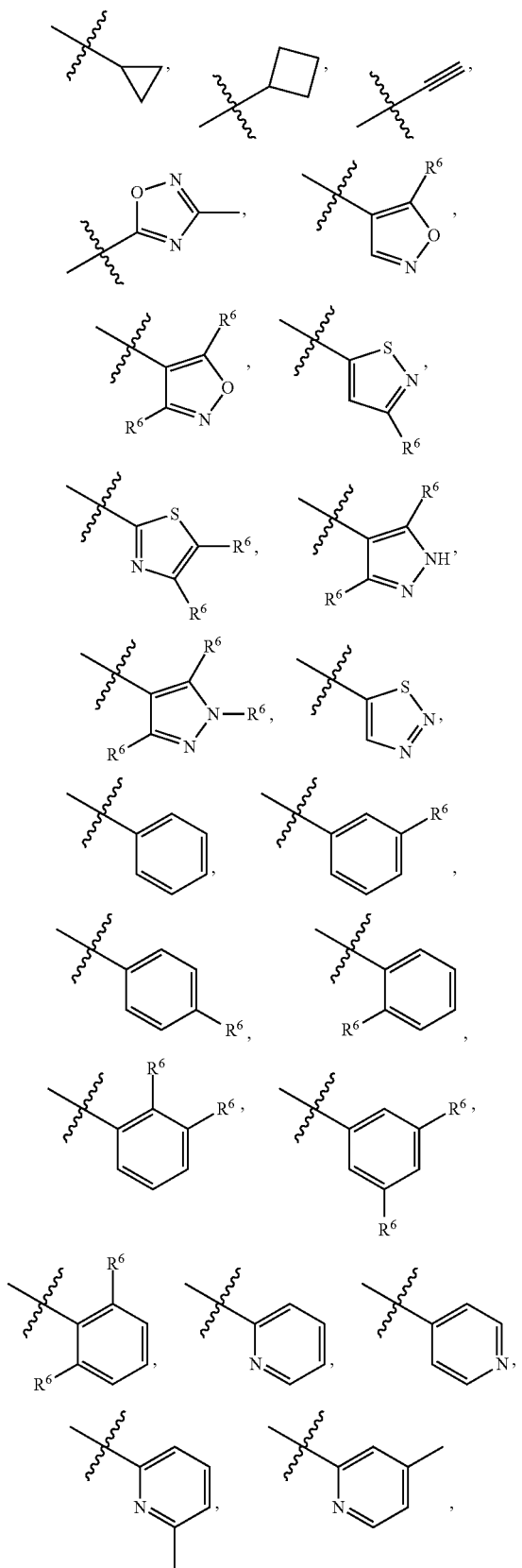
In some embodiments, $R^{4c}$ is chosen from:
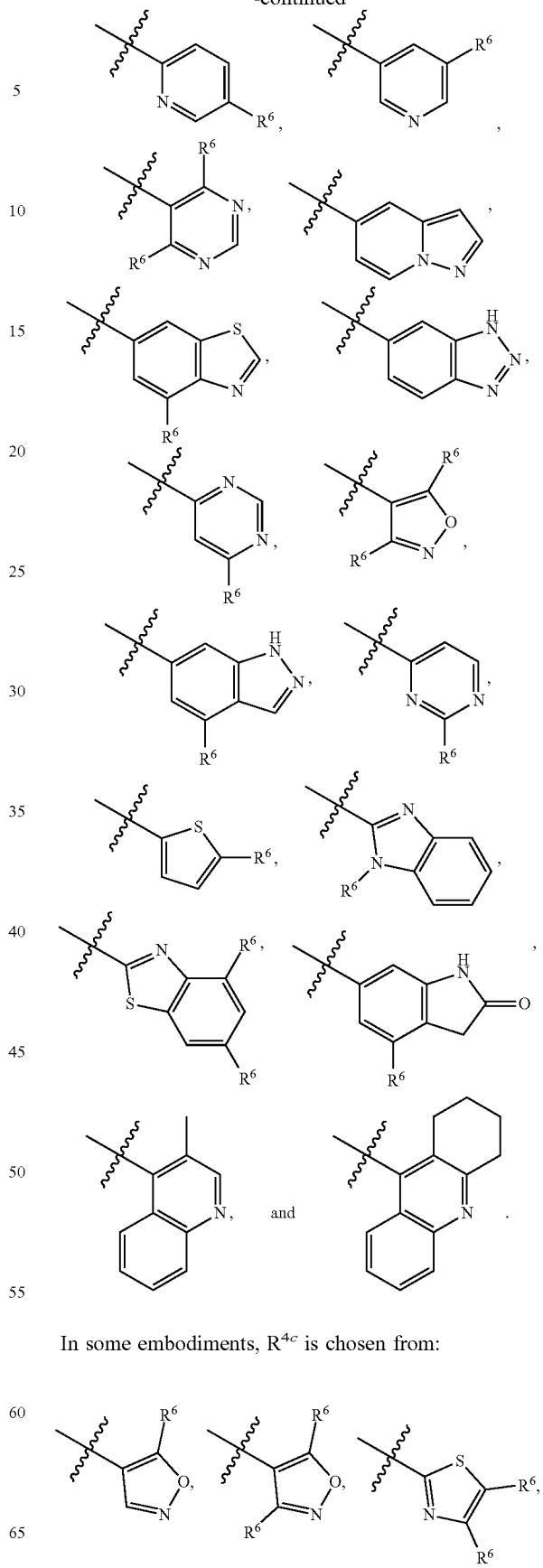

-continued
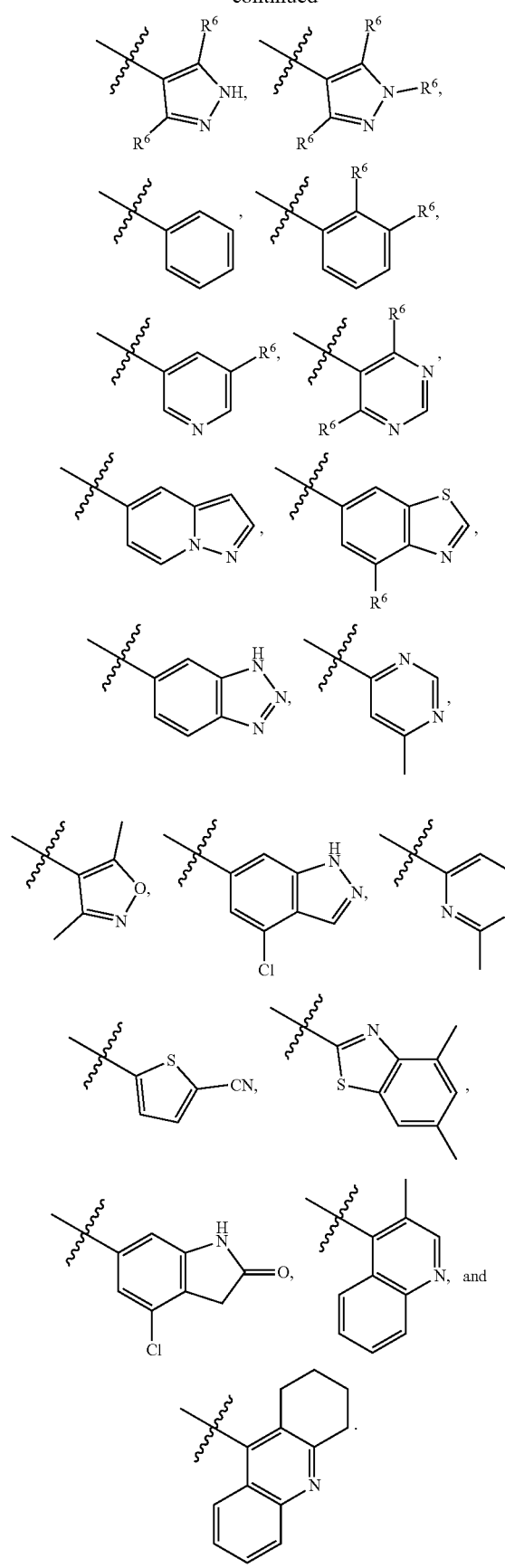
In some embodiments, $R^{4c}$ is chosen from:

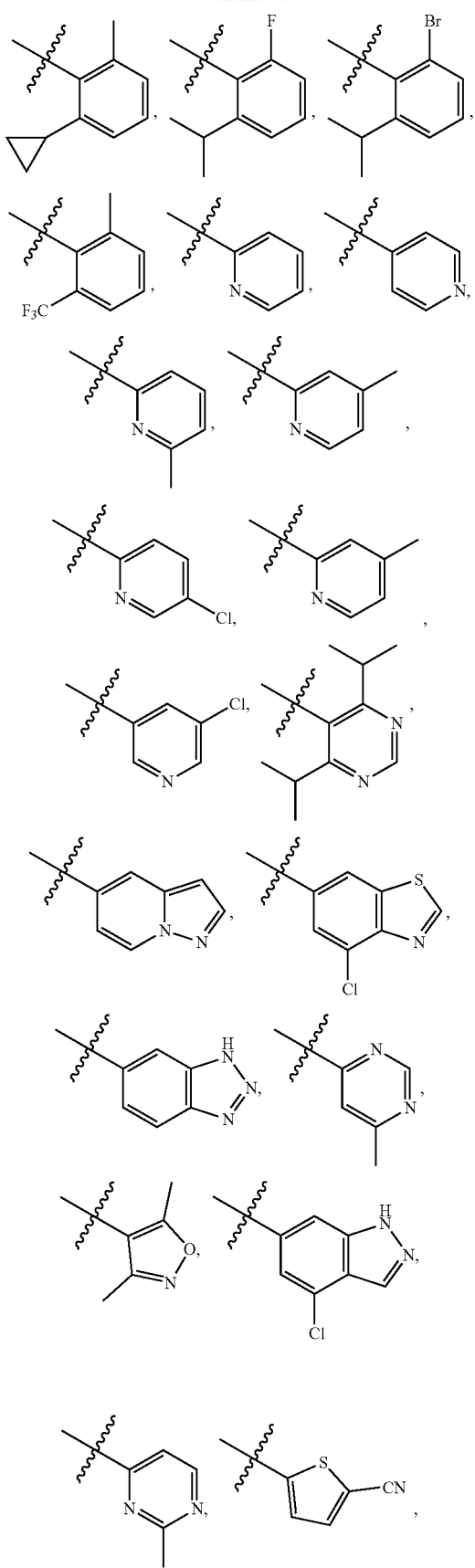
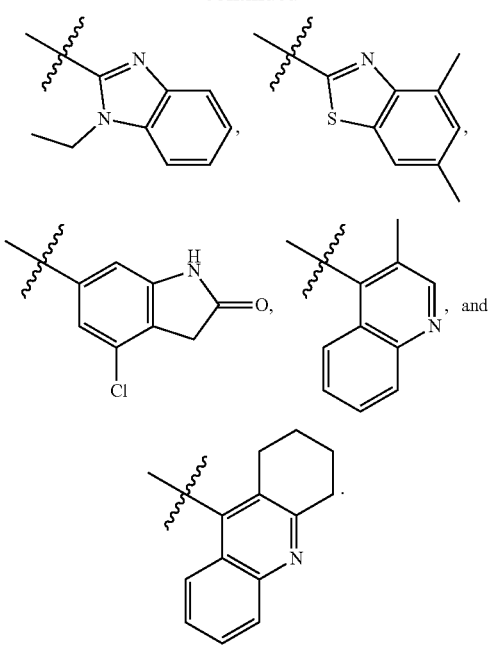
In some embodiments, $R^{4c}$ is chosen from:
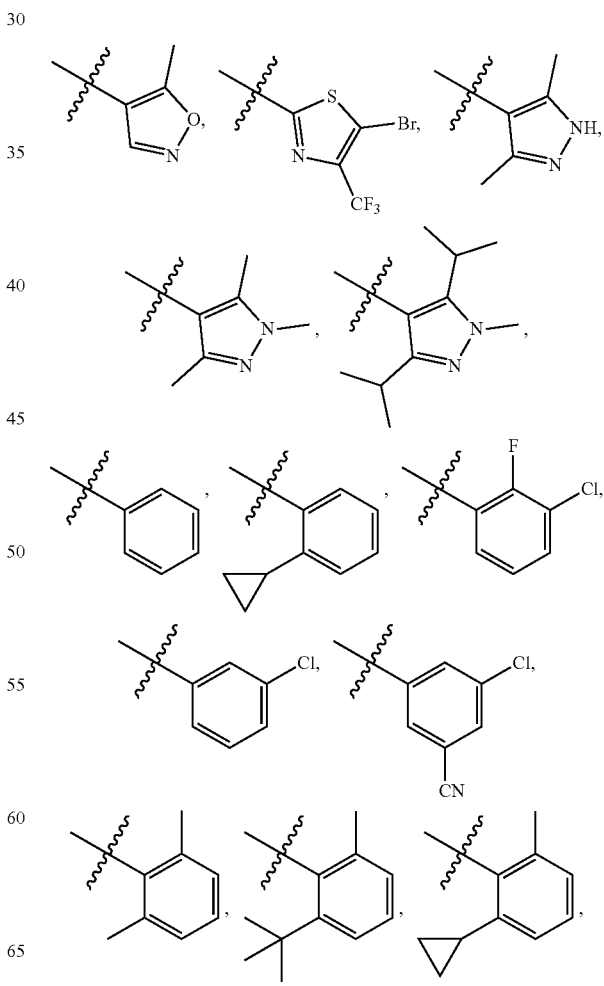

-continued

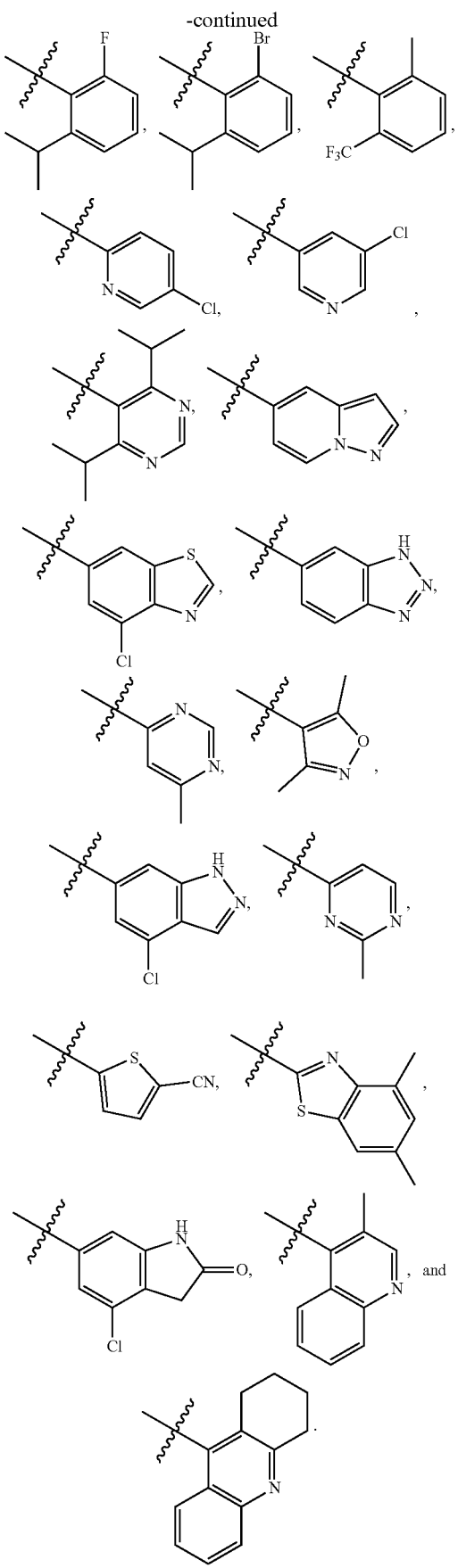

In some embodiments, each $R^{4d}$ is independently chosen from H and $C_{1-6}$alkyl.

In some embodiments, each $R^{4d}$ is independently chosen from H, $CH_3$, and $CH_2CH_3$.

In some embodiments, each $R^{4d}$ is independently chosen from H and $CH_3$.

In some embodiments, at most one $R^{4d}$ is not H.

In some embodiments, each $R^{4d}$ is H.

In some embodiments, each $R^5$ is independently chosen from CN, halo, hydroxy, oxo, $C_{1-6}$alkyl, $C_{3-7}$cycloalkyl, and $(C_{1-6}$alkyl$)$oxy.

In some embodiments, each $R^5$ is independently chosen from CN, F, Cl, Br, hydroxy, methyl, and methoxy.

In some embodiments, each $R^5$ is independently chosen from F and Ck.

In some embodiments, $R^5$ is F.

In some embodiments, $W^4$ is chosen from $CHR^{6c}$, $NR^{6c}$, and $CR^{6c}$; and $W^2$, $W^3$, $W^4$, $W^5$, $W^6$, and $W^7$, together with the intervening carbon, combine to form a 7-membered cycloalkyl, heterocycloalkyl, aryl, or heteroaryl.

In some embodiments, $W^4$ is a bond; and $W^2$, $W^3$, $W^5$, $W^6$, and $W^7$, together with the intervening carbon, combine to form a 6-membered cycloalkyl, heterocycloalkyl, aryl, or heteroaryl.

In some embodiments, $W^2$ is chosen from $CR^{6a}$ and N; $W^3$ is chosen from $CR^{6b}$ and N; $W^5$ is chosen from $CR^{6d}$ and N; $W^6$ is chosen from $CR^{6e}$ and N; $W^7$ is chosen from $CR^{6f}$ and N; and $W^2$, $W^3$, $W^5$, $W^6$, and $W^7$, together with the intervening carbon, combine to form phenyl or a 6-membered heteroaryl.

In some embodiments, at most two of $W^2$, $W^3$, $W^5$, $W^6$, and $W^7$ are N.

In some embodiments, exactly one of $W^2$, $W^3$, $W^5$, $W^6$, and $W^7$ is N.

In some embodiments, exactly two of $W^2$, $W^3$, $W^5$, $W^6$, and $W^7$ are N.

In some embodiments, $W^2$ is $CR^{6a}$; $W^3$ is $CR^{6b}$; $W^5$ is $CR^{6d}$; $W^6$ is $CR^{6e}$; $W^7$ is $CR^{6f}$; and $W^2$, $W^3$, $W^5$, $W^6$, and $W^7$, together with the intervening carbon, combine to phenyl.

In some embodiments, $W^2$ is chosen from $CHR^{6a}$, $NR^{6a}$, and $CR^{6a}$; $W^3$ is chosen from $CHR^{6b}$, $NR^{6b}$, and $CR^{6b}$; $R^{6a}$ and $R^{6b}$ combine, together with the intervening two atoms, to form a 5-, 6-, or 7-membered cycloalkyl, heterocycloalkyl, aryl, or heteroaryl, any one of which is optionally substituted with one or more $R^6$; and $R^{6c}$, $R^{6d}$, $R^{6e}$, and $R^{6f}$ are independently chosen from H, CN, halo, hydroxy, oxo, alkyl, cycloalkyl, heterocycloalkyl, aryl, and heteroaryl.

In some embodiments, $W^2$ is chosen from $CR^{6a}$ and $NR^{6a}$; $W^3$ is chosen from $CR^{6b}$ and $NR^{6b}$; $R^{6a}$ and $R^{6b}$ combine, together with the intervening two atoms, to form a 5-, 6-, or 7-membered aryl or heteroaryl, any one of which is optionally substituted with one or more $R^6$.

In some embodiments, $W^2$ is chosen from $CHR^{6a}$, $NR^{6a}$ and $CR^{6a}$; $W^3$ is chosen from $CHR^{6b}$, $NR^{6b}$ and $CR^{6b}$; $W^6$ is chosen from $CR^{6e}$ and $NR^{6e}$; $W^7$ is chosen from $CR^{6f}$ and $NR^{6f}$; $R^{6a}$ and $R^{6b}$ combine, together with the intervening two atoms, to form a 5-, 6-, or 7-membered cycloalkyl, heterocycloalkyl, aryl or heteroaryl, any one of which is optionally substituted with one or more $R^6$; and $R^{6e}$ and $R^{6f}$ combine, together with the intervening two atoms, to form a 5-, 6-, or 7-membered aryl or heteroaryl, any one of which is optionally substituted with one or more $R^6$; and $R^bc$ and $R^{6d}$ are independently chosen from H, CN, halo, hydroxy, oxo, alkyl, cycloalkyl, heterocycloalkyl, aryl, and heteroaryl.

In some embodiments, $W^4$ and $W^5$ are $CH_2$.

In some embodiments, $W^2$ is $CHR^{6a}$; $W^6$ is $CHR^{6e}$; $R^{6b}$, $R^{6c}$ and $R^{6f}$ are independently chosen from CN, halo, hydroxy, oxo, alkyl, cycloalkyl, heterocycloalkyl, aryl, and heteroaryl; and $R^{6a}$ and $R^{6e}$ combine to form alkylene, which is optionally substituted with one or more $R^6$.

In some embodiments, $W^2$ is chosen from $CHR^{6a}$, $NR^{6a}$, O, and S; $W^3$ is chosen from $CHR^{6b}$, $NR^{6b}$, O, and S; $W^2$, $W^3$, $W^4$, $W^5$, $W^6$, and $W^7$, together with the intervening carbon, combine to form a 7-membered cycloalkyl or heterocycloalkyl; and each of $R^{6a}$ and $R^{6b}$ is independently chosen from H, CN, halo, hydroxy, oxo, alkyl, cycloalkyl, heterocycloalkyl, aryl, and heteroaryl.

In some embodiments, $W^2$ is chosen from $CHR^{6a}$ and O; and $W^3$ is chosen from $CHR^{6b}$ and O.

In some embodiments, $W^2$ and $W^3$ are independently chosen from $CH_2$ and O.

In some embodiments, exactly one of $W^2$ and $W^3$ is O.

In some embodiments, $W^2$ is O.

In some embodiments, $W^3$ is O.

In some embodiments, $W^5$ is chosen from $CHR^{6d}$, $NR^{6d}$, and $CR^{6d}$, $R^{6c}$ and $R^{6d}$ combine, together with the intervening two atoms, to form a 5-, 6-, or 7-membered cycloalkyl, heterocycloalkyl, aryl, or heteroaryl, any one of which is optionally substituted with one or more $R^6$; and $R^{6a}$, $R^{6b}$, $R^{6e}$, and $R^{6f}$ are independently chosen from H, CN, halo, hydroxy, oxo, alkyl, cycloalkyl, heterocycloalkyl, aryl, and heteroaryl.

In some embodiments, $W^4$ is chosen from $CR^{6c}$ and $NR^{6c}$; $W^5$ is chosen from $CR^{6d}$ and $NR^{6d}$; $R^{6c}$ and $R^{6d}$ combine, together with the intervening two atoms, to form a 5-, 6-, or 7-membered aryl or heteroaryl, any one of which is optionally substituted with one or more $R^6$.

In some embodiments, $W^4$ is chosen from $CR^{6c}$ and $NR^{6c}$; $W^5$ is chosen from $CR^{6d}$ and $NR^{6d}$; $W^6$ is chosen from $CR^{6e}$ and $NR^{6e}$; $W^7$ is chosen from $CR^{6f}$ and $NR^{6f}$; $R^{6c}$ and $R^{6d}$ combine, together with the intervening two atoms, to form a 5-, 6-, or 7-membered aryl or heteroaryl, any one of which is optionally substituted with one or more $R^6$; $R^{6e}$ and $R^{6f}$ combine, together with the intervening two atoms, to form a 5-, 6-, or 7-membered aryl or heteroaryl, any one of which is optionally substituted with one or more $R^6$; and $R^{6a}$ and $R^{6b}$ are independently chosen from H, CN, halo, hydroxy, oxo, alkyl, cycloalkyl, heterocycloalkyl, aryl, and heteroaryl.

In some embodiments, $W^7$ is C=O.

In some embodiments, $W^2$ and $W^3$ are $CHR^{6h}$. In some embodiments, $W^2$ and $W^3$ are $CH_2$.

In some embodiments, $W^6$ is $NR^{6e}$; and $R^{6e}$ is chosen from H, alkyl, and cycloalkyl.

In some embodiments, at least one of $W^2$, $W^3$, $W^4$, $W^5$, and $W^6$ is N.

In some embodiments, exactly one of $W^2$, $W^3$, $W^4$, $W^5$, and $W^6$ is N.

In some embodiments, $W^2$ is N.
In some embodiments, $W^3$ is N.
In some embodiments, $W^4$ is N.
In some embodiments, $W^5$ is N.

In some embodiments, exactly two of $W^2$, $W^3$, $W^4$, $W^5$, and $W^6$ are N.

In some embodiments, none of $W^2$, $W^3$, $W^4$, $W^5$, and $W^6$ is N.

In some embodiments, exactly one of $W^2$, $W^3$, $W^4$, $W^5$, and $W^6$ is N.

In some embodiments, exactly two of $W^2$, $W^3$, $W^4$, $W^5$, and $W^6$ are N.

In some embodiments, $W^2$ is $CR^6a$; $W^3$ is $CR^{6b}$; and $R^{6a}$ and $R^{6b}$, together with the intervening two carbons, combine to form cycloalkyl, heterocycloalkyl, aryl or heteroaryl, either of which is optionally substituted with one $R^6$. In some embodiments, $R^{6a}$ and $R^{6b}$, together with the intervening two carbons, combine to form aryl or heteroaryl, either one of which is optionally substituted with one $R^6$. In some embodiments, $R^{6a}$ and $R^{6b}$, together with the intervening two carbons, combine to form phenyl or 5-membered heteroaryl, either one of which is optionally substituted with one $R^6$. In some embodiments, $R^{6a}$ and $R^{6b}$, together with the intervening two carbons, combine to form 5-membered heteroaryl which is optionally substituted with one $R^6$. In some embodiments, $R^{6a}$ and $R^{6b}$, together with the intervening two carbons, combine to form pyrazolyl, thiazolyl, or triazolyl, any one of which is optionally substituted with one $R^6$.

In some embodiments, $W^3$ is $CR^{6b}$; $W^4$ is $CR^{6c}$; and $R^{6b}$ and $R^{6c}$, together with the intervening two carbons, combine to form cycloalkyl, heterocycloalkyl, aryl, or heteroaryl, any of which is optionally substituted with one $R^6$. In some embodiments, $R^{6b}$ and $R^{6c}$, together with the intervening two carbons, combine to form aryl or heteroaryl, either one of which is optionally substituted with one $R^6$. In some embodiments, $R^{6b}$ and $R^{6c}$, together with the intervening two carbons, combine to form phenyl or 5-membered heteroaryl, either one of which is optionally substituted with one $R^6$. In some embodiments, $R^{6b}$ and $R^{6c}$, together with the intervening two carbons, combine to form 5-membered heteroaryl which is optionally substituted with one $R^6$. In some embodiments, $R^{6b}$ and $R^{6c}$, together with the intervening two carbons, combine to form pyrazolyl, thiazolyl, or triazolyl, any one of which is optionally substituted with one $R^6$.

In some embodiments, wherein: $W^4$ is $CR^{6c}$; $W^5$ is $CR^{6d}$; and $R^{6c}$ and $R^{6d}$, together with the intervening two carbons, combine to form cycloalkyl, heterocycloalkyl, aryl or heteroaryl, either one of which is optionally substituted with one $R^6$. In some embodiments, $R^{6c}$ and $R^{6d}$, together with the intervening two carbons, combine to form aryl or heteroaryl, either one of which is optionally substituted with one $R^6$. In some embodiments, $R^{6c}$ and $R^{6d}$, together with the intervening two carbons, combine to form phenyl or 5-membered heteroaryl, either one of which is optionally substituted with one $R^6$. In some embodiments, $R^{6c}$ and $R^{6d}$, together with the intervening two carbons, combine to form 5-membered heteroaryl which is optionally substituted with one $R^6$. In some embodiments, $R^{6c}$ and $R^{6d}$, together with the intervening two carbons, combine to form pyrazolyl, thiazolyl, or triazolyl, any one of which is optionally substituted with one $R^6$.

In some embodiments, $W^5$ is $CR^{6d}$; and $W^6$ is $CR^{6e}$; and $R^{6d}$ and $R^{6e}$, together with the intervening two carbons, combine to form cycloalkyl, heterocycloalkyl, aryl or heteroaryl, either one of which is optionally substituted with one $R^6$. In some embodiments, $R^{6d}$ and $R^{6e}$, together with the intervening two carbons, combine to form aryl or heteroaryl, either one of which is optionally substituted with one $R^6$. In some embodiments, $R^{6d}$ and $R^{6e}$, together with the intervening two carbons, combine to form phenyl or 5-membered heteroaryl, either one of which is optionally substituted with one $R^6$. In some embodiments, $R^{6d}$ and $R^{6e}$, together with the intervening two carbons, combine to form 5-membered heteroaryl which is optionally substituted with one $R^6$. In some embodiments, $R^{6d}$ and $R^{6e}$, together with the intervening two carbons, combine to form pyrazolyl, thiazolyl, or triazolyl, any one of which is optionally substituted with one $R^6$.

In some embodiments, $V^1$ is a bond; $V^2$, $V^3$, and $V^4$ are independently chosen from $CR^{6g}$, N, $NR^{6g}$, O, and S; and $V^2$, $V^3$, and $V^4$, together with the intervening two carbons, combine to form a 5-membered heteroaryl.

In some embodiments, at least one of $V^2$, $V^3$, and $V^4$ is chosen from N and $NR^{6g}$.

In some embodiments, at least two of $V^2$, $V^3$, and $V^4$ are chosen from N and $NR^{6g}$.

In some embodiments, at least one of $V^2$, $V^3$, and $V^4$ is chosen from O and S.

In some embodiments, at most three of $V^2$, $V^3$, and $V^4$ are $CR^{6g}$.

In some embodiments, at most two of $V^2$, $V^3$, and $V^4$ are $CR^{6g}$.

In some embodiments, $V^1$, $V^2$, $V^3$, and $V^4$ are independently chosen from $CR^{6g}$ and N; and $V^1$, $V^2$, $V^3$, and $V^4$, together with the intervening two carbons, combine to form phenyl or a 6-membered heteroaryl.

In some embodiments, either one or two of $V^1$, $V^2$, $V^3$, and $V^4$ are N.

In some embodiments, exactly one of $V^1$, $V^2$, $V^3$, and $V^4$ is N.

In some embodiments, at most one of $V^1$, $V^2$, $V^3$, and $V^4$ is N. In some embodiments, $V^1$, $V^2$, $V^3$, and $V^4$ are $CR^{6g}$; and $V^1$, $V^2$, $V^3$, and $V^4$, together with the intervening two carbons, combine to form phenyl.

In some embodiments, each $R^6$ is independently chosen from F, Cl, Br, CN, $CH_3$, $CH_2CH_3$, $CH(CH_3)_2$, $C(CH_3)_3$, $OCH_3$, and $CF_3$.

In some embodiments, each $R^6$ is independently chosen from CN, halo, hydroxy, oxo, $C_{1-6}$alkyl, halo$C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)-oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)($C_{1-6}$alkyl)N, ($C_{6-10}$aryl)($C_{1-6}$alkyl)N, and (5- to 10-membered heteroaryl heteroaryl)($C_{1-6}$alkyl)N.

In some embodiments, at most one $R^6$ is chosen from $C_{1-6}$alkyl, halo$C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)($C_{1-6}$alkyl)N, ($C_{6-10}$aryl)($C_{1-6}$alkyl)N, and (5- to 10-membered heteroaryl heteroaryl)($C_{1-6}$alkyl)N.

In some embodiments, each $R^6$ is chosen from CN, halo, hydroxy, oxo, $C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, and (5- to 10-membered heteroaryl)oxy.

In some embodiments, at most one $R^6$ is chosen from $C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, and (5- to 10-membered heteroaryl)oxy.

In some embodiments, each $R^6$ is independently chosen from CN, halo, hydroxy, oxo, ($C_{3-7}$cycloalkyl)$C_{1-2}$alkyl, (4- to 11-membered heterocycloalkyl)$C_{1-2}$alkyl, ($C_{6-10}$aryl)$C_{1-2}$alkyl, (5- to 10-membered heteroaryl)$C_{1-2}$alkyl, ($C_{1-6}$alkyl)oxy, ($C_{3-7}$cycloalkyl)oxy, (4- to 11-membered heterocycloalkyl)oxy, ($C_{6-10}$aryl)oxy, and (5- to 10-membered heteroaryl)oxy.

In some embodiments, at most one $R^6$ is chosen from ($C_{3-7}$cycloalkyl)$C_{1-2}$alkyl, (4- to 11-membered heterocycloalkyl)$C_{1-2}$alkyl, ($C_{6-10}$aryl)$C_{1-2}$alkyl, (5- to 10-membered heteroaryl)$C_{1-2}$alkyl, ($C_{1-6}$alkyl)oxy, ($C_{3-7}$cycloalkyl)oxy, (4- to 11-membered heterocycloalkyl)oxy, ($C_{6-10}$aryl)oxy, and (5- to 10-membered heteroaryl)oxy.

In some embodiments, each $R^6$ is independently chosen from CN, halo, hydroxy, oxo, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)($C_{1-6}$alkyl)N, ($C_{6-10}$aryl)($C_{1-6}$alkyl)N, and (5- to 10-membered heteroaryl heteroaryl)($C_{1-6}$alkyl)N.

In some embodiments, at most one $R^6$ is chosen from ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)($C_{1-6}$alkyl)N, ($C_{6-10}$aryl)($C_{1-6}$alkyl)N, and (5- to 10-membered heteroaryl heteroaryl)($C_{1-6}$alkyl)N.

In some embodiments, each $R^6$ is independently chosen from CN, halo, hydroxy, oxo, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($CH_3$)N, ($C_{3-7}$cycloalkyl)($CH_3$)N, (4- to 11-membered heterocycloalkyl)($CH_3$)N, ($C_{6-10}$aryl)($CH_3$)N, and (5- to 10-membered heteroaryl heteroaryl)($CH_3$)N.

In some embodiments, at most one $R^6$ is chosen from ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($CH_3$)N, ($C_{3-7}$cycloalkyl)($CH_3$)N, (4- to 11-membered heterocycloalkyl)($CH_3$)N, ($C_{6-10}$aryl)($CH_3$)N, and (5- to 10-membered heteroaryl heteroaryl)($CH_3$)N.

In some embodiments, each $R^6$ is independently chosen from CN, halo, hydroxy, oxo, $C_{1-6}$alkyl, halo$C_{1-6}$alkyl, $C_{3-7}$cycloalkyl, 4- to 11-membered heterocycloalkyl, $C_{6-10}$aryl, and 5- to 10-membered heteroaryl.

In some embodiments, each $R^6$ is independently chosen from CN, halo, hydroxy, oxo, $C_{1-6}$alkyl, halo$C_{1-6}$alkyl, $C_{3-7}$cycloalkyl, and 4- to 11-membered heterocycloalkyl.

In some embodiments, each $R^6$ is independently chosen from CN, halo, hydroxy, oxo, $C_{1-6}$alkyl, halo$C_{1-6}$alkyl, and $C_{3-7}$cycloalkyl.

In some embodiments, each $R^6$ is independently chosen from CN, halo, hydroxy, oxo, methyl, ethyl, halomethyl, haloethyl, and $C_{3-6}$ cycloalkyl.

In some embodiments, each $R^6$ is independently chosen from CN, halo, oxo, methyl, fluoromethyl, difluoromethyl, trifluoromethyl, and $C_{3-6}$ cycloalkyl.

In some embodiments, each $R^6$ is independently chosen from CN, halo, oxo, methyl, difluoromethyl, trifluoromethyl, and $C_{3-5}$ cycloalkyl.

In some embodiments, each $R^6$ is independently chosen from CN, F, Cl, Br, oxo, methyl, trifluoromethyl, and cyclopropyl.

In some embodiments, at least one $R^6$ is $C_{1-6}$alkyl.

In some embodiments, at least one $R^6$ is halo.

In some embodiments, at least one $R^6$ is Cl.

In some embodiments, $R^{6a}$, $R^{6b}$, $R^{6c}$, $R^{6d}$, and $R^{6e}$ are independently chosen from H, CN, halo, hydroxy, $C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)(alkyl)N, (aryl)(alkyl)N, and (heteroaryl)(alkyl)N.

In some embodiments, at most one of $R^{6a}$, $R^{6b}$, $R^{6c}$, $R^{6d}$, and $R^{6e}$ is chosen from $C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)(alkyl)N, (aryl)(alkyl)N, and (heteroaryl)(alkyl)N.

In some embodiments, $R^{6a}$, $R^{6b}$, $R^{6c}$, $R^{6d}$, and $R^{6e}$ a are independently chosen from H, CN, halo, hydroxy, $C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, and (5- to 10-membered heteroaryl)NH.

In some embodiments, at most one of $R^{6a}$, $R^{6b}$, $R^{6c}$, $R^{6d}$, and $R^{6e}$ is chosen from $C_{1-6}$alkyl, $C_{3-7}$cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy.

In some embodiments, $R^{6a}$, $R^{6b}$, $R^{6c}$, $R^{6d}$, and $R^{6e}$ are independently chosen from H, CN, halo, hydroxy, $C_{1-6}$alkyl, $C_{3-7}$cycloalkyl, 4- to 11-membered heterocycloalkyl, $C_{6-10}$aryl, 5- to 10-membered heteroaryl, ($C_{1-6}$alkyl)oxy, ($C_{3-7}$cycloalkyl)oxy, (4- to 11-membered heterocycloalkyl)oxy, ($C_{6-10}$aryl)oxy, and (5- to 10-membered heteroaryl)oxy.

In some embodiments, at most one of $R^{6a}$, $R^{6b}$, $R^{6c}$, $R^{6d}$, and $R^{6e}$ is chosen from $C_{1-6}$alkyl, $C_{3-7}$cycloalkyl, 4- to 11-membered heterocycloalkyl, $C_{6-10}$aryl, 5- to 10-membered heteroaryl, ($C_{1-6}$alkyl)oxy, ($C_{3-7}$cycloalkyl)oxy, (4- to 11-membered heterocycloalkyl)oxy, ($C_{6-10}$aryl)oxy, and (5- to 10-membered heteroaryl)oxy.

In some embodiments, $R^{6a}$, $R^{6b}$, $R^{6c}$, $R^{6d}$, and $R^{6e}$ a are independently chosen from H, CN, halo, hydroxy, $C_{1-6}$alkyl, $C_{3-7}$cycloalkyl, 4- to 11-membered heterocycloalkyl, $C_{6-10}$aryl, 5- to 10-membered heteroaryl, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)(alkyl)N, (aryl)(alkyl)N, and (heteroaryl)(alkyl)N.

In some embodiments, at most one of $R^{6a}$, $R^{6b}$, $R^{6c}$, $R^{6d}$, and $R^{6e}$ is chosen from $C_{1-6}$alkyl, $C_{3-7}$cycloalkyl, 4- to 11-membered heterocycloalkyl, $C_{6-10}$aryl, 5- to 10-membered heteroaryl, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)(alkyl)N, (aryl)(alkyl)N, and (heteroaryl)(alkyl)N.

In some embodiments, $R^{6a}$, $R^{6b}$, $R^{6c}$, $R^{6d}$, and $R^{6e}$ are independently chosen from H, CN, halo, hydroxy, alkyl, cycloalkyl, heterocycloalkyl, aryl, and heteroaryl.

In some embodiments, $R^{6a}$, $R^{6b}$, $R^{6c}$, $R^{6d}$, and $R^{6e}$ are independently chosen from H, CN, halo, hydroxy, $C_{1-6}$alkyl, $C_{3-7}$cycloalkyl, 4- to 11-membered heterocycloalkyl, $C_{6-10}$aryl, and 5- to 10-membered heteroaryl.

In some embodiments, $R^{6a}$, $R^{6b}$, $R^{6c}$, $R^{6d}$, and $R^{6e}$ are independently chosen from H, CN, halo, hydroxy, methyl, ethyl, cyclopropyl, and cyclobutyl.

In some embodiments, $R^{6a}$, $R^{6b}$, $R^{6c}$, $R^{6d}$, and $R^{6e}$ are independently chosen from H, CN, halo, hydroxy, and methyl.

In some embodiments, at least one of $R^{6a}$, $R^{6b}$, $R^{6c}$, $R^{6d}$, and $R^{6e}$ is not H.

In some embodiments, at least one of $R^{6a}$, $R^{6b}$, $R^{6c}$, $R^{6d}$, and $R^{6e}$ is alkyl.

In some embodiments, at least one of $R^{6a}$, $R^{6b}$, $R^{6c}$, $R^{6d}$, and $R^{6e}$ is methyl.

In some embodiments, at least one of $R^{6a}$, $R^{6b}$, $R^{6c}$, $R^{6d}$, and $R^{6e}$ is halo.

In some embodiments, at least two of $R^{6a}$, $R^{6b}$, $R^{6c}$, $R^{6d}$, and $R^{6e}$ are halo.

In some embodiments, at least one of $R^{6a}$, $R^{6b}$, $R^{6c}$, $R^{6d}$, and $R^{6e}$ is Cl.

In some embodiments, at least one of $R^{6a}$, $R^{6b}$, $R^{6c}$, $R^{6d}$, and $R^{6e}$ is F.

In some embodiments, at least one of $R^{6a}$, $R^{6b}$, $R^{6c}$, $R^{6d}$, and $R^{6e}$ is Br.

In some embodiments, none of $W^2$, $W^3$, $W^4$, $W^5$, and $W^6$ is N.

In some embodiments, at least one of $R^{6a}$, $R^{6b}$, $R^{6c}$, $R^{6d}$, and $R^{6e}$ is not H.

In some embodiments, at least two of $R^{6a}$, $R^{6b}$, $R^{6c}$, $R^{6d}$, and $R^{6e}$ are not H.

In some embodiments, each $R^{6a}$ is independently chosen from H, F, Cl, Br, CN, $CH_3$, $CH_2CH_3$, $CH(CH_3)_2$, $C(CH_3)_3$, $OCH_3$, and $CF_3$.

In some embodiments, at most one $R^{6a}$ is H.

In some embodiments, $R^{6a}$ is $CH_3$.

In some embodiments, $R^{6a}$ is cyclopropyl.

In some embodiments, $R^{6a}$ is halo. In some embodiments, $R^{6a}$ is Cl. In some embodiments, $R^{6a}$ is Br. In some embodiments, $R^{6a}$ is F.

In some embodiments, $R^{6a}$ is not halo. In some embodiments, $R^{6a}$ is not F.

In some embodiments, $R^{6a}$ is not alkyl. In some embodiments, $R^{6a}$ is not $CH(CH_3)_2$.

In some embodiments, $R^{6b}$ is chosen from H, $CH_3$, and $CH_2CH_3$.

In some embodiments, $R^{6b}$ is Cl. In some embodiments, $R^{6b}$ is F. In some embodiments, $R^{6b}$ is Br.

In some embodiments, $R^{6b}$ is not halo. In some embodiments, $R^{6b}$ is not F.

In some embodiments, $R^{6b}$ is not alkyl. In some embodiments, $R^{6b}$ is not methyl.

In some embodiments, $R^{6b}$ is not cycloalkyl.

In some embodiments, neither of $R^{6a}$ and $R^{6b}$ is H.

In some embodiments, neither of $R^{6a}$ and $R^{6e}$ is H.

In some embodiments, $R^{6c}$ is F.

In some embodiments, $R^{6c}$ is not alkyl. In some embodiments, $R^{6c}$ is not $CH_3$.

In some embodiments, $R^{6d}$ is not halo. In some embodiments, $R^{6d}$ is not F. In some embodiments, $R^{6d}$ is not Cl.

In some embodiments, $R^{6d}$ is not alkyl. In some embodiments, $R^{6d}$ is not methyl.

In some embodiments, $R^{6d}$ is not cycloalkyl.

In some embodiments, $R^{6e}$ is H. In some embodiments, $R^{6e}$ is $C_{1-6}$alkyl. In some embodiments, $R^{6e}$ is $CH_3$.

In some embodiments, $R^{6e}$ is not $CH(CH_3)_2$.

In some embodiments, $R^{6f}$ is chosen from alkyl and cycloalkyl.

In some embodiments, each $R^{6g}$ is independently chosen from H, CN, halo, hydroxy, oxo, $C_{1-6}$alkyl, halo$C_{1-6}$alkyl, $C_{3-7}$cycloalkyl, 4- to 11-membered heterocycloalkyl, $C_{6-10}$aryl, 5- to 10-membered heteroaryl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($C_{1-6}$alkyl)N, ($C_{3-7}$cycloalkyl)($C_{1-6}$alkyl)N, (4- to 11-membered heterocycloalkyl)($C_{1-6}$alkyl)N, ($C_{6-10}$aryl)($C_{1-6}$alkyl)N, and (5- to 10-membered heteroaryl)($C_{1-6}$alkyl)N.

In some embodiments, each $R^{6g}$ is independently chosen from H, CN, halo, hydroxy, oxo, $C_{1-6}$alkyl, halo$C_{1-6}$alkyl, $C_{3-7}$cycloalkyl, 4- to 11-membered heterocycloalkyl, $C_{6-10}$aryl, 5- to 10-membered heteroaryl, ($C_{3-7}$cycloalkyl)$C_{1-2}$alkyl, (4- to 11-membered heterocycloalkyl)$C_{1-2}$alkyl, ($C_{6-10}$aryl)$C_{1-2}$alkyl, (5- to 10-membered heteroaryl)$C_{1-2}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, (5- to 10-membered heteroaryl)NH, ($C_{1-6}$alkyl)($CH_3$)N, ($C_{3-7}$cycloalkyl)($CH_3$)N, (4- to 11-membered heterocycloalkyl)($CH_3$)N, ($C_{6-10}$aryl)($CH_3$)N, and (5- to 10-membered heteroaryl)($CH_3$)N.

In some embodiments, each $R^{6g}$ is independently chosen from H, CN, halo, hydroxy, oxo, $C_{1-6}$alkyl, halo$C_{1-6}$alkyl, $C_{3-7}$cycloalkyl, 4- to 11-membered heterocycloalkyl, $C_{6-10}$aryl, 5- to 10-membered heteroaryl, ($C_{3-7}$cycloalkyl)$C_{1-2}$alkyl, (4- to 11-membered heterocycloalkyl)$C_{1-2}$alkyl, ($C_{6-10}$aryl)$C_{1-2}$alkyl, (5- to 10-membered heteroaryl)$C_{1-2}$alkyl, ($C_{1-6}$alkyl)oxy, ($C_{3-7}$cycloalkyl)oxy, (4- to 11-membered heterocycloalkyl)oxy, ($C_{6-10}$aryl)oxy, (5- to 10-membered heteroaryl)oxy, ($C_{1-6}$alkyl)NH, ($C_{3-7}$cycloalkyl)NH, (4- to 11-membered heterocycloalkyl)NH, ($C_{6-10}$aryl)NH, and (5- to 10-membered heteroaryl)NH.

In some embodiments, each $R^{6g}$ is independently chosen from H, CN, halo, hydroxy, oxo, $C_{1-6}$alkyl, halo$C_{1-6}$alkyl, $C_{3-7}$cycloalkyl, 4- to 11-membered heterocycloalkyl, ($C_{3-7}$cycloalkyl)$C_{1-2}$alkyl, (4- to 11-membered heterocycloalkyl)$C_{1-2}$alkyl, ($C_{1-6}$alkyl)oxy, ($C_{3-7}$cycloalkyl)oxy, (4- to 11-membered heterocycloalkyl)oxy, ($C_{1-6}$alkyl)NH, ($C_{3-7}$cycloalkyl)NH, and (4- to 11-membered heterocycloalkyl)NH.

In some embodiments, each $R^{6g}$ is independently chosen from H, CN, halo, hydroxy, oxo, $C_{1-6}$alkyl, $C_{3-7}$cycloalkyl, 4- to 11-membered heterocycloalkyl, ($C_{3-7}$cycloalkyl)$C_{1-6}$alkyl, (4- to 11-membered heterocycloalkyl)$C_{1-6}$alkyl, $C_{6-10}$aryl, and 5- to 10-membered heteroaryl.

In some embodiments, at most one $R^{6g}$ is chosen from $C_{1-6}$alkyl, $C_{3-7}$cycloalkyl, 4- to 11-membered heterocycloalkyl, ($C_{3-7}$cycloalkyl)$C_{1-6}$alkyl, (4- to 11-membered heterocycloalkyl)$C_{1-6}$alkyl, $C_{6-10}$aryl, and 5- to 10-membered heteroaryl.

In some embodiments, each $R^{6g}$ is independently chosen from H, CN, halo, hydroxy, and oxo.

In some embodiments, each $R^{6g}$ is independently chosen from H, CN, halo, and hydroxy.

In some embodiments, each $R^{6g}$ is independently chosen from H, CN, and halo.

In some embodiments, each $R^{6g}$ is independently chosen from H, F, and Cl.

In some embodiments, at least one $R^{6g}$ is not H. In some embodiments, at least two $R^{6g}$ are not H. In some embodiments, at least three $R^{6g}$ are not H.

In some embodiments, at least one $R^{6g}$ is H. In some embodiments, at least two of $R^{6g}$ are H. In some embodiments, at least three of $R^{6g}$ are H. In some embodiments, at least four of $R^{6g}$ are H. In some embodiments, $R^{6g}$ is H.

In some embodiments, $R^{6h}$ is chosen from H, CN, halo, hydroxy, oxo, and alkyl.

In some embodiments, two $R^{6h}$ on adjacent atoms, together with the carbons to which they are attached, combine to form $C_{3-7}$cycloalkyl.

In some embodiments, two $R^{6h}$ on adjacent atoms, together with the carbons to which they are attached, combine to form cyclopropyl.

In some embodiments, neither of $R^{6a}$ and $R^{6b}$ is H.

In some embodiments, at most two of $R^{6a}$, $R^{6b}$, $R^{6c}$, $R^{6d}$, and $R^{6e}$ is H.

In some embodiments, at most one of $R^{6a}$, $R^{6b}$, $R^{6c}$, $R^{6d}$, and $R^{6e}$ is H. In some embodiments, at least one of $R^{6a}$, $R^{6b}$, $R^{6c}$, $R^{6d}$, and $R^{6e}$ is not H. In some embodiments, at least two of $R^{6a}$, $R^{6b}$, $R^{6c}$, $R^{6d}$, and $R^{6e}$ are not H.

In some embodiments, at least one of $R^{6a}$, $R^{6b}$, $R^{6d}$, $R^{6e}$, and $R^{6f}$ is not H. In some embodiments, at least two of $R^{6a}$, $R^{6b}$, $R^{6d}$, $R^{6e}$, and $R^{6f}$ are not H.

In some embodiments, none of $R^{6a}$, $R^{6b}$, $R^{6c}$, $R^{6d}$, and $R^{6e}$ is aryl or heteroaryl.

In some embodiments, none of $R^{6a}$, $R^{6b}$, $R^{6c}$, $R^{6d}$, and $R^{6e}$ is cycloalkyl or heterocycloalkyl.

In some embodiments, none of $R^{6a}$, $R^{6b}$, $R^{6c}$, $R^{6d}$, and $R^{6e}$ is alkyl.

In some embodiments, $R^{6a}$ and $R^{6e}$ combine to form $C_{2-3}$alkylene, which is optionally substituted with one or two $R^6$.

In some embodiments, $R^{6a}$ and $R^{6e}$ combine to form $C_2$alkylene, which is optionally substituted with one $R^6$.

In some embodiments, $R^{6a}$ and $R^{6e}$ combine to form —CH$_2$CH$_2$—.

In some embodiments, at most one of $R^{6a}$, $R^{6b}$, $R^{6c}$, $R^{6d}$, $R^{6e}$, and $R^{6f}$ is aryl or heteroaryl. In some embodiments, none of $R^{6a}$, $R^{6b}$, $R^{6c}$, $R^{6d}$, $R^{6e}$, and $R^{6f}$ is aryl or heteroaryl.

In some embodiments, at most one of $R^{6a}$, $R^{6b}$, $R^{6c}$, $R^{6d}$, $R^{6e}$, and $R^{6f}$ is alkyl, cycloalkyl, or heterocycloalkyl. In some embodiments, none of $R^{6a}$, $R^{6b}$, $R^{6c}$, $R^{6d}$, $R^{6e}$, and $R^{6f}$ is alkyl, cycloalkyl, or heterocycloalkyl.

In some embodiments, at most one of $R^{6a}$, $R^{6b}$, $R^{6c}$, $R^{6d}$, $R^{6e}$, and $R^{6f}$ is cyano or hydroxy. In some embodiments, none of $R^{6a}$, $R^{6b}$, $R^{6c}$, $R^{6d}$, $R^{6e}$ and $R^{6f}$ is cyano or hydroxy.

In some embodiments, at most two of $R^{6a}$, $R^{6b}$, $R^{6c}$, $R^{6d}$, $R^{6e}$, and $R^{6f}$ is halo. In some embodiments, at most one of $R^{6a}$, $R^{6b}$, $R^{6c}$, $R^{6d}$, $R^{6e}$, and $R^{6f}$ is halo. In some embodiments, none of $R^{6a}$, $R^{6b}$, $R^{6c}$, $R^{6d}$, $R^{6e}$, and $R^{6f}$ is halo.

In some embodiments, at most one of $R^{6a}$, $R^{6b}$, $R^{6c}$, $R^{6d}$, $R^{6e}$, and $R^{6f}$ is oxo. In some embodiments, none of $R^{6a}$, $R^{6b}$, $R^{6c}$, $R^{6d}$, $R^{6e}$, and $R^{6f}$ is oxo.

Also provided is a compound chosen from:

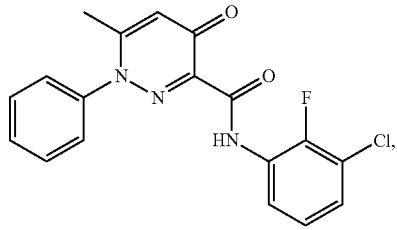

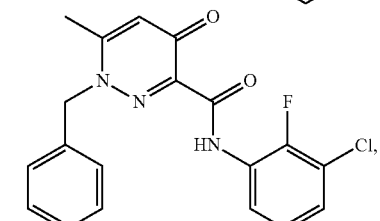

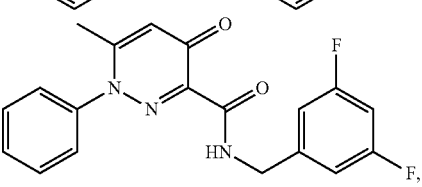

-continued

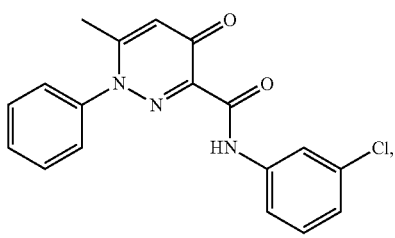

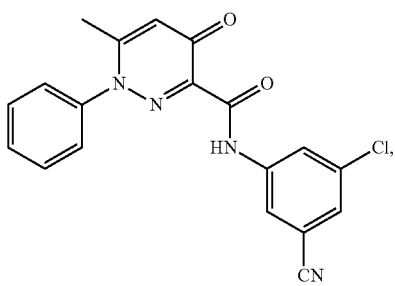

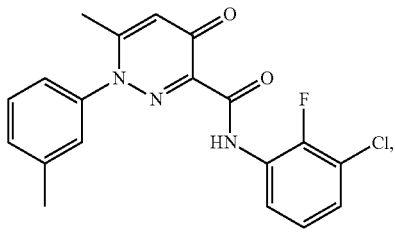

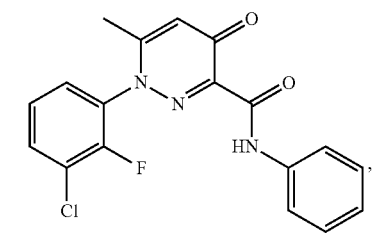

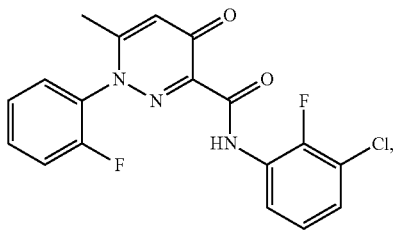

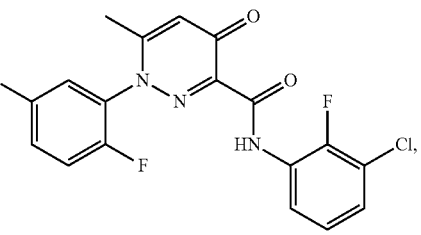

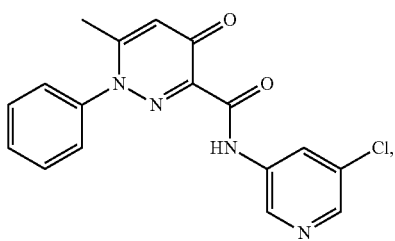

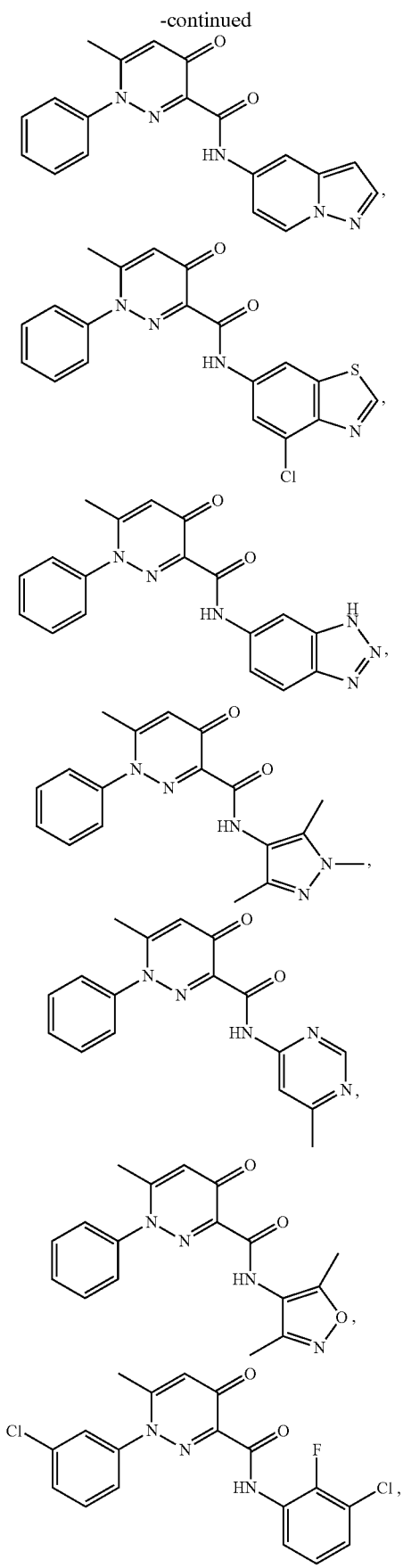
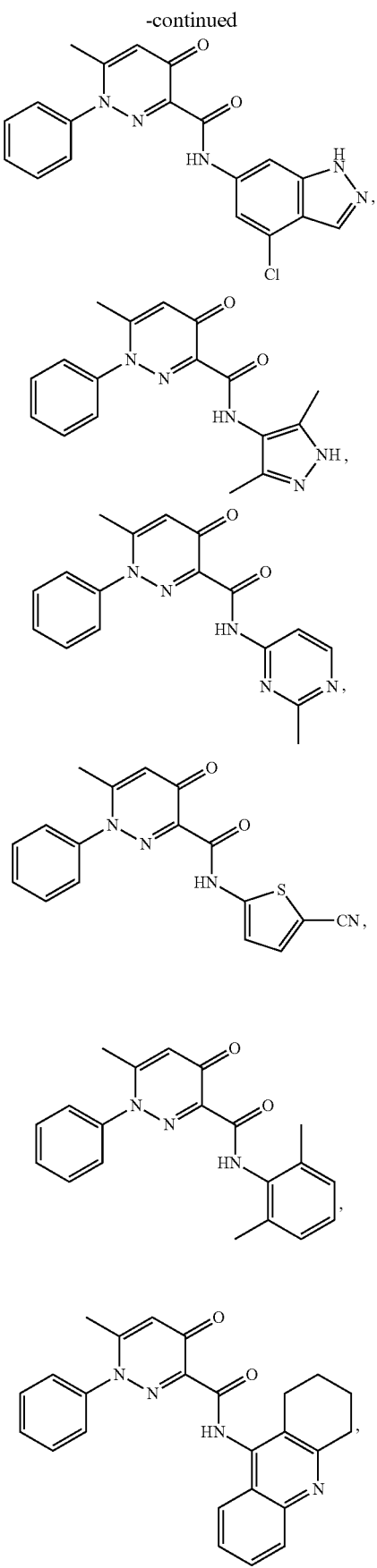

-continued
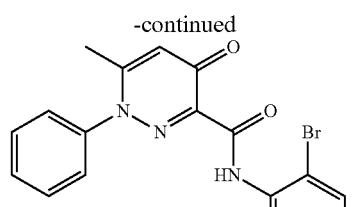
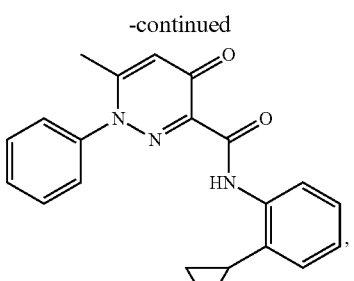
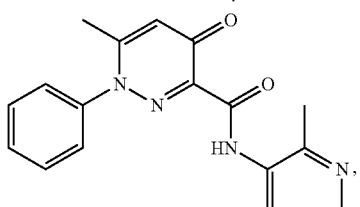
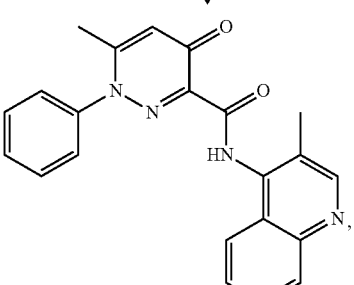
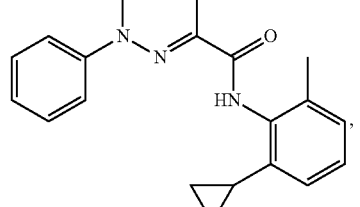
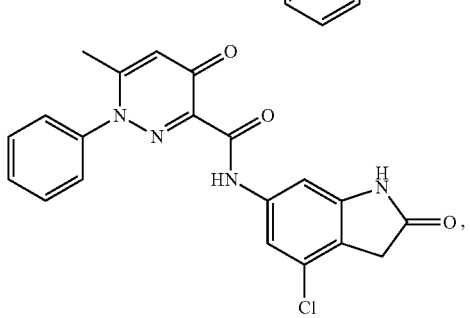
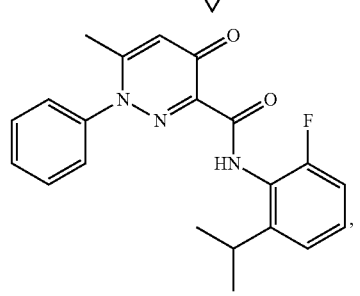
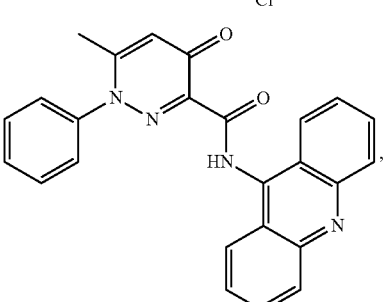
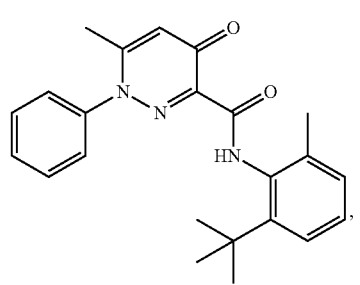
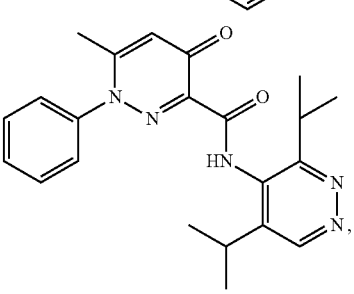
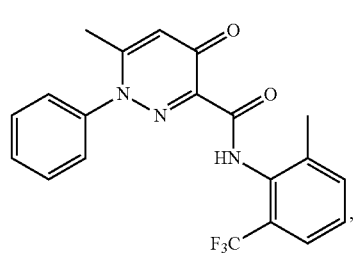

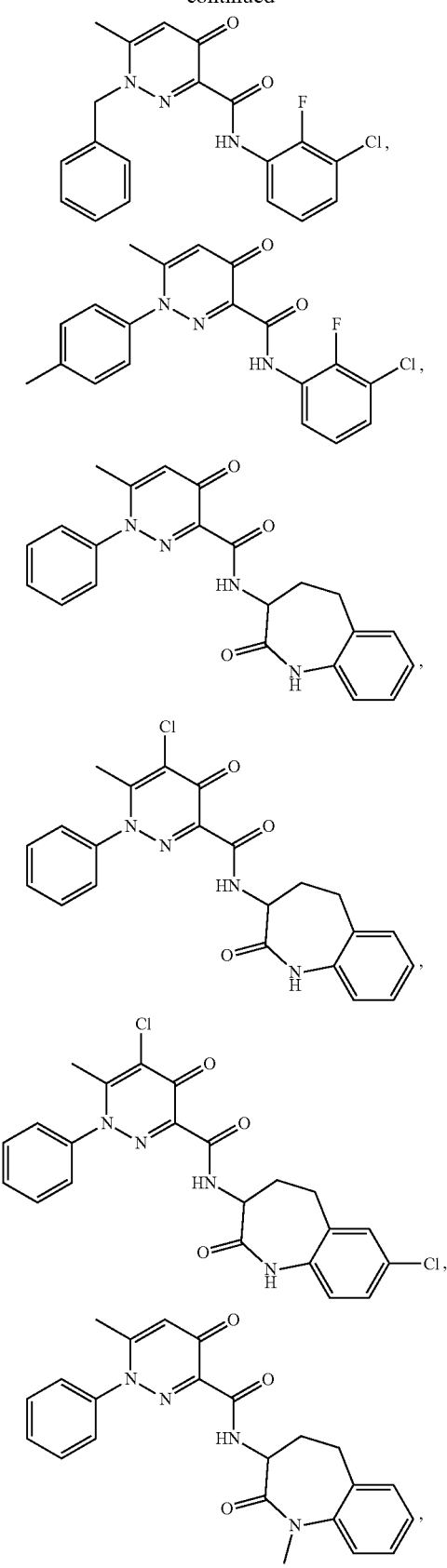
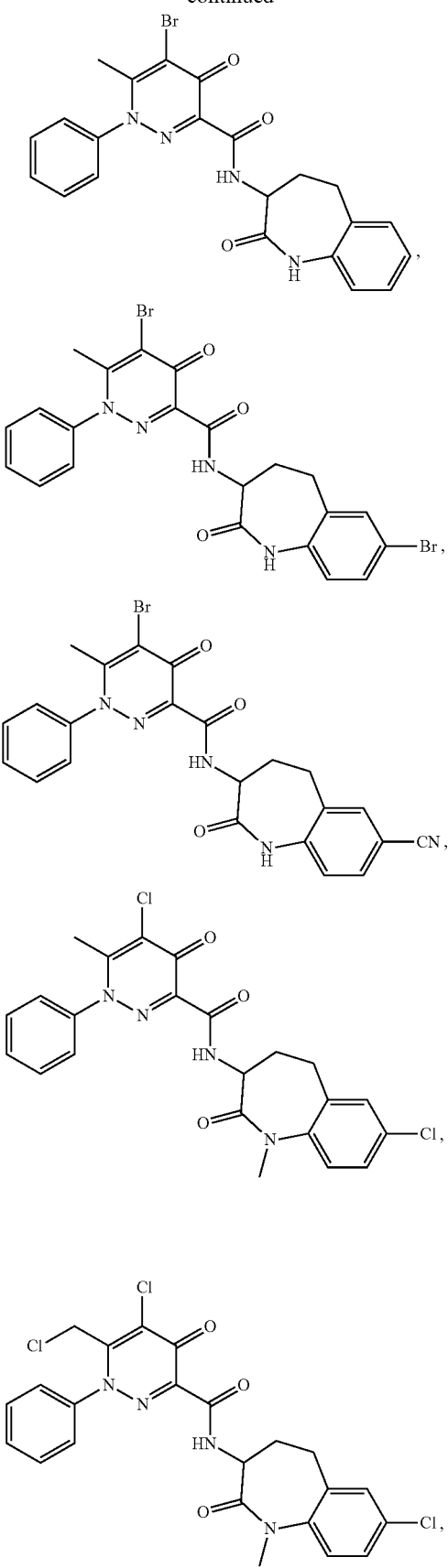

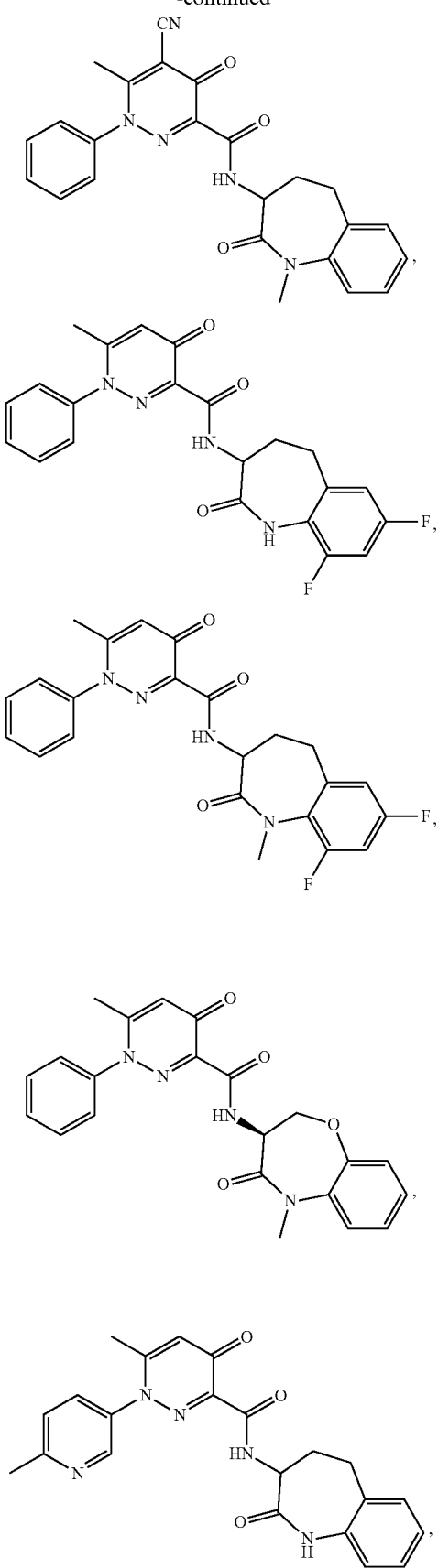
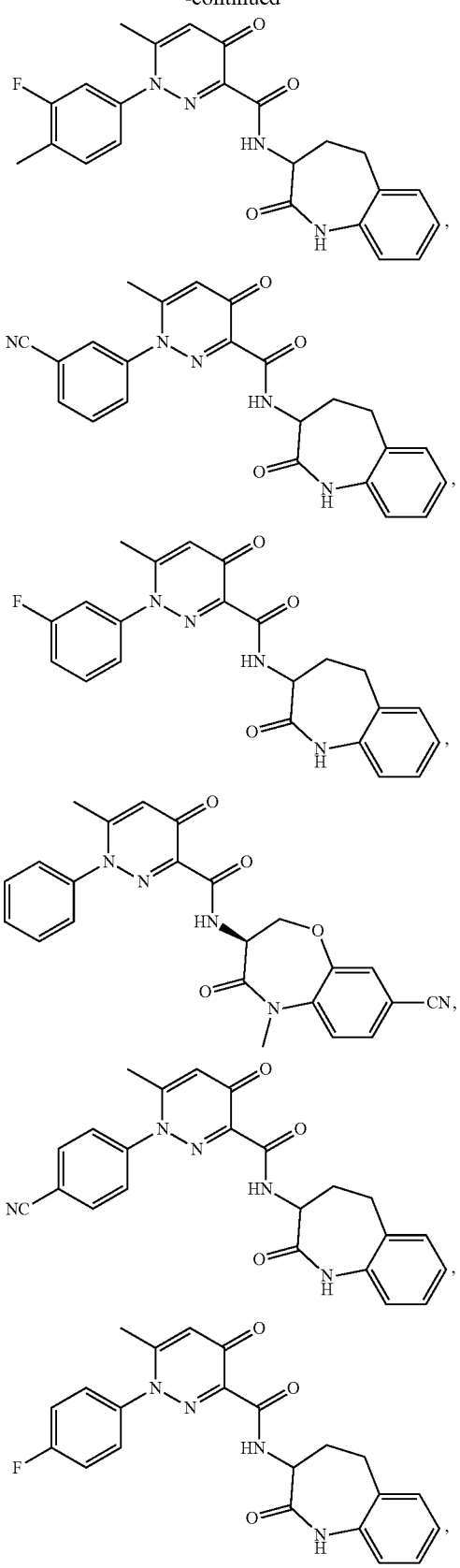

-continued
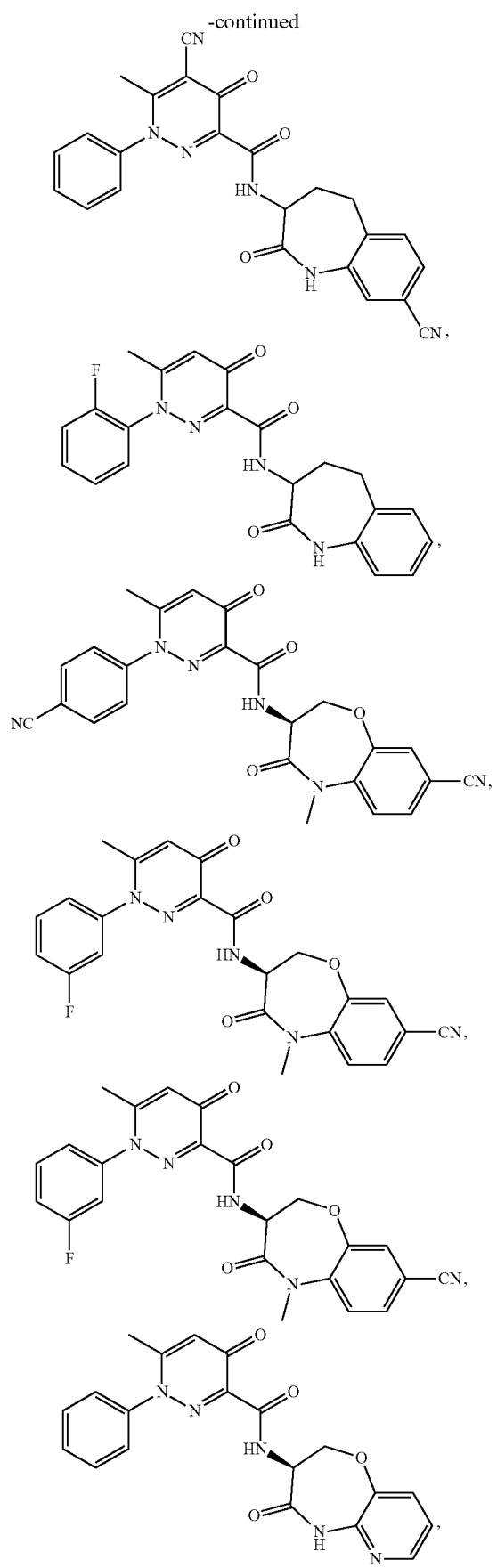
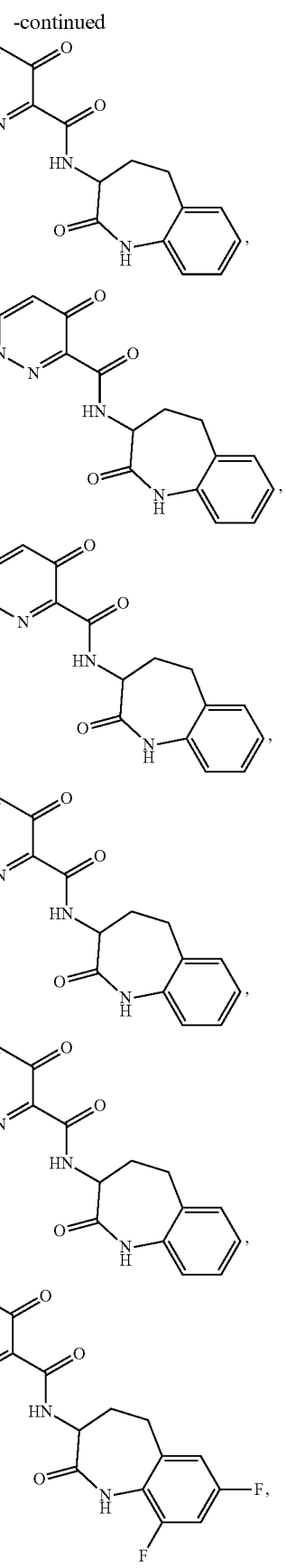

47
-continued
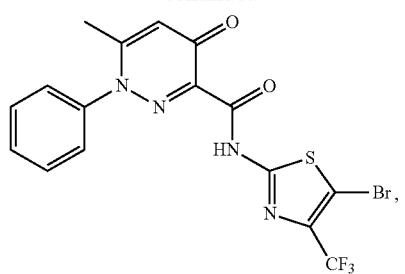
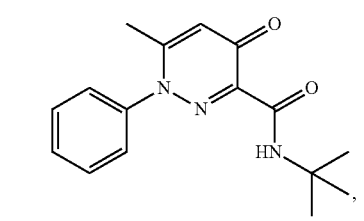
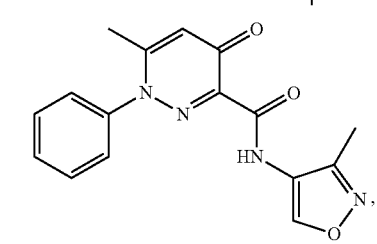
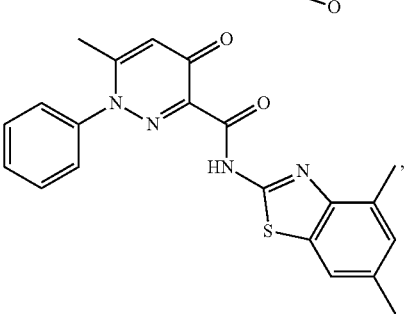
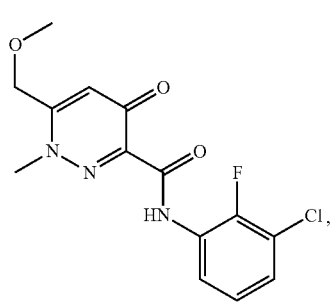
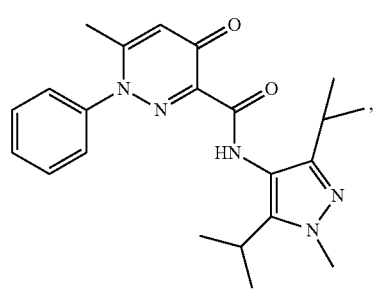
48
-continued
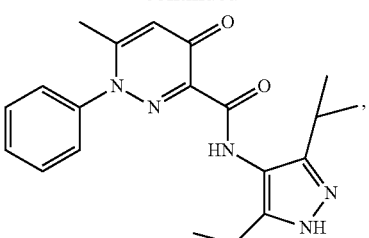
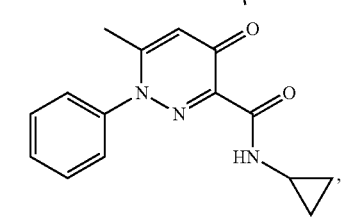
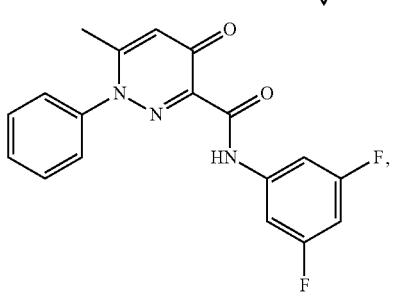
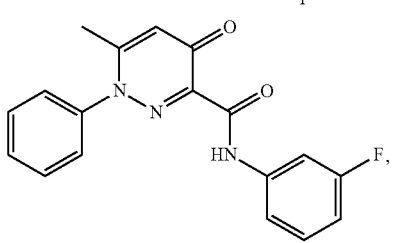
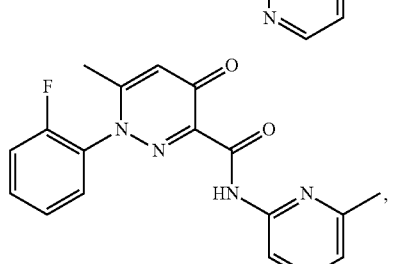
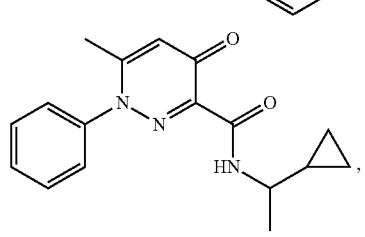

-continued
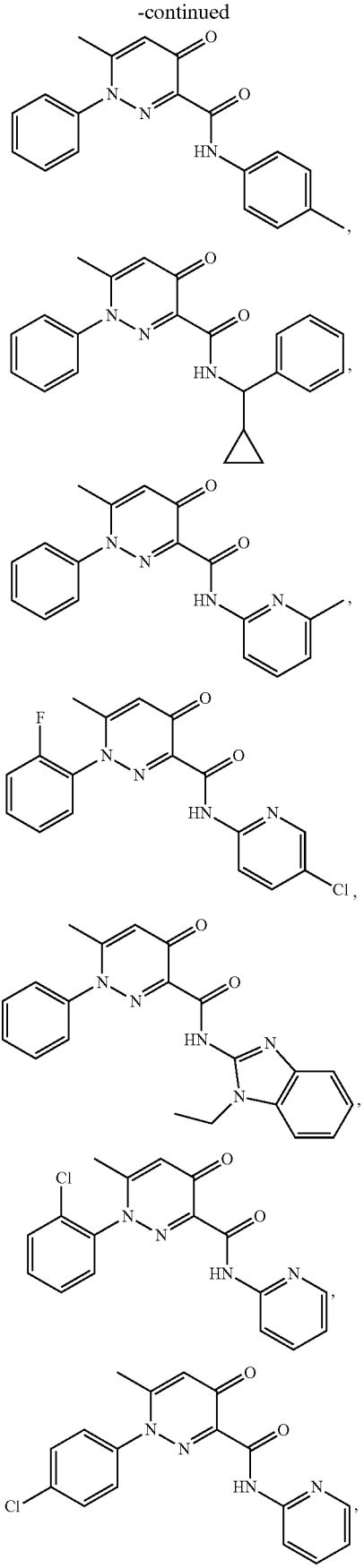
-continued
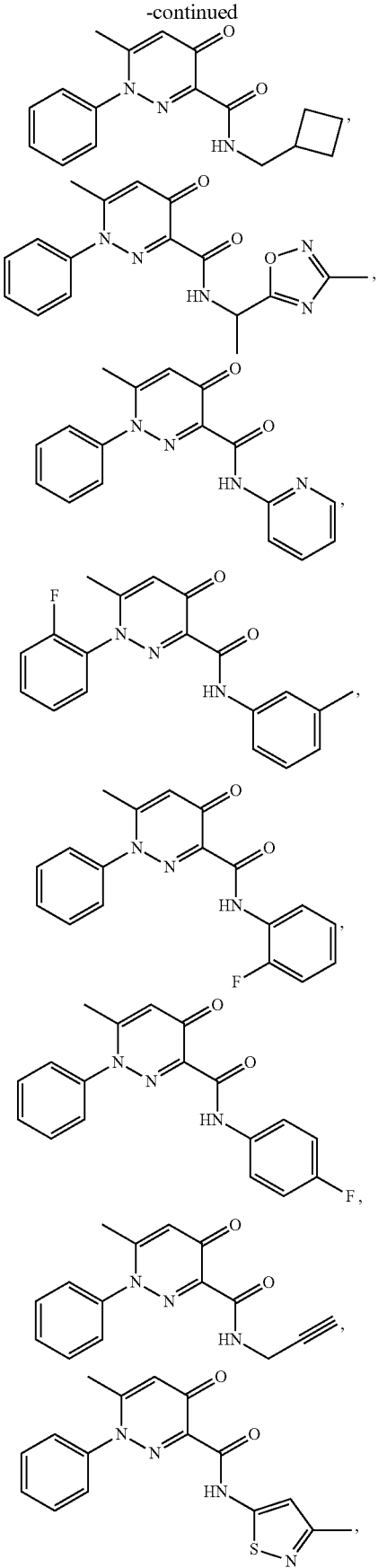

51
-continued
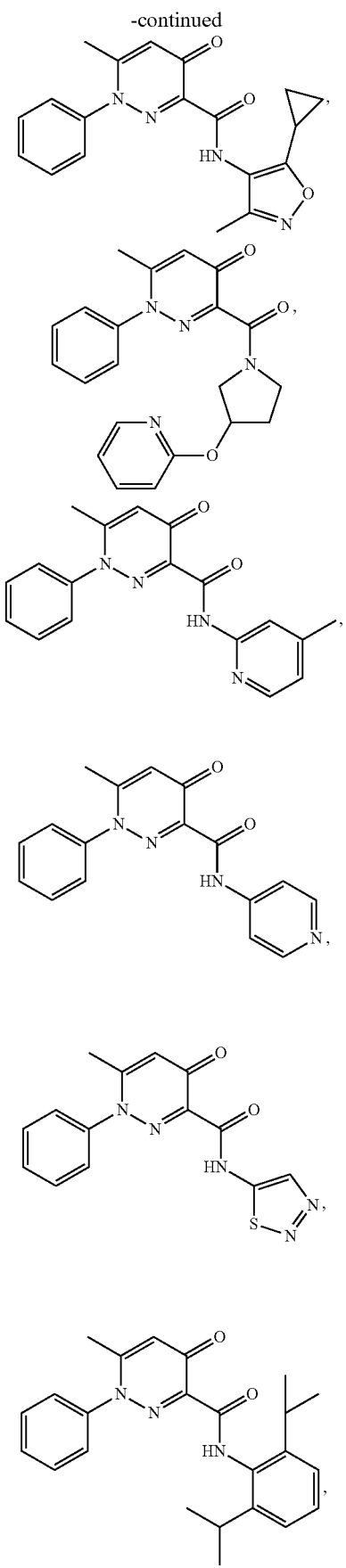
52
-continued
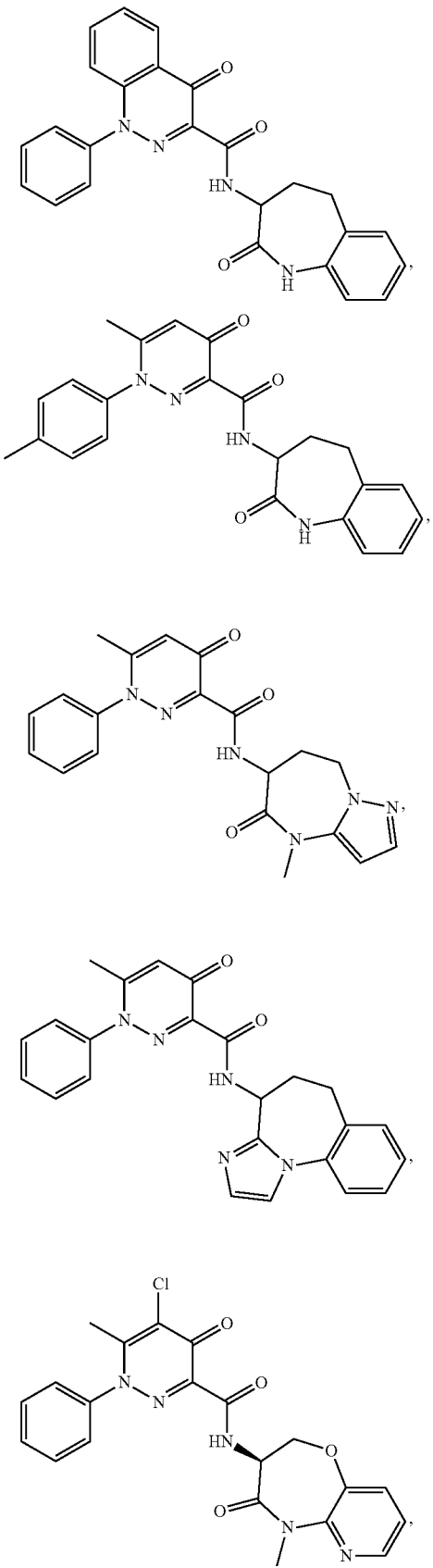

-continued

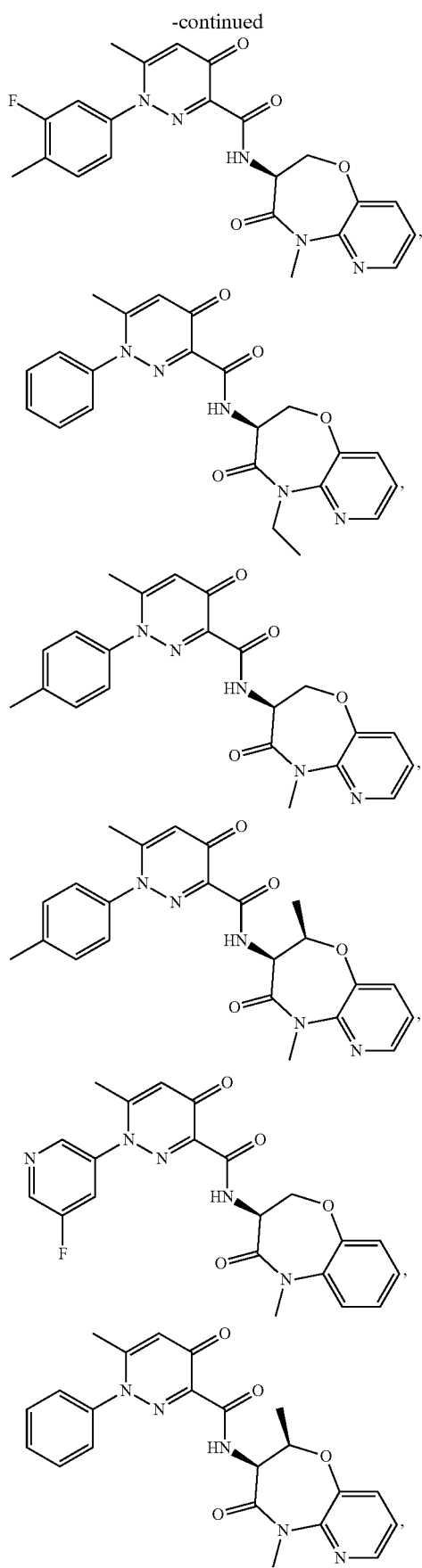

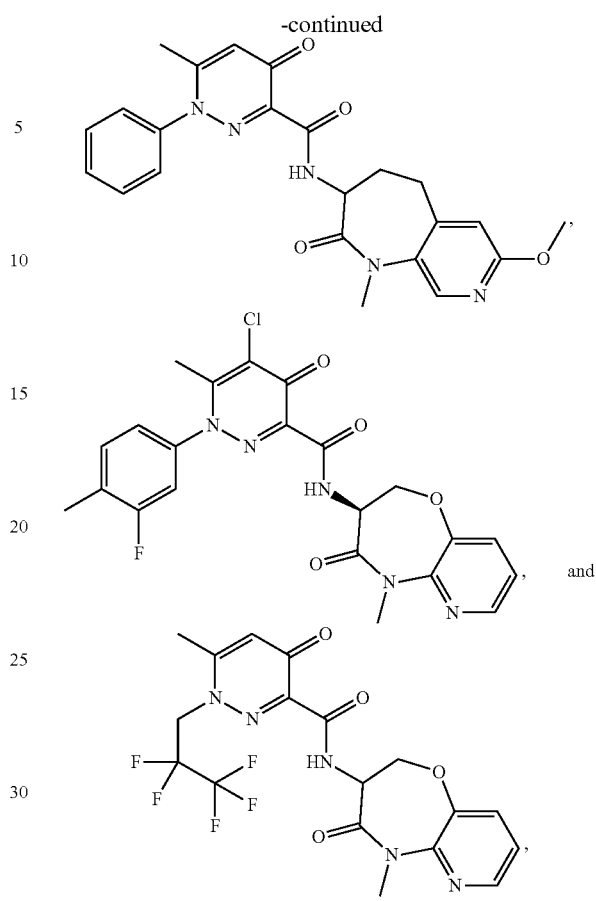

or a salt thereof.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

Also provided are methods of inhibiting at least one RIPK1 function comprising the step of contacting RIPK1 with a compound as described herein. The cell phenotype, cell proliferation, activity of RIPK1, change in biochemical output produced by active RIPK1, expression of RIPK1, or binding of RIPK1 with a natural binding partner may be monitored. Such methods may be modes of treatment of disease, biological assays, cellular assays, biochemical assays, or the like.

Also provided herein are methods of treatment of a RIPK1-mediated disease comprising the administration of a therapeutically effective amount of a compound as disclosed herein, or a salt thereof, to a patient in need thereof.

In certain embodiments, the disease is chosen from neurodegenerative disorders, inflammatory disorders, and cancer.

In certain embodiments, the disease is cancer. In certain embodiments, the cancer is treated by promoting an appropriate immune response to the tumor. In certain embodiments, the appropriate immune response to the tumor comprises, or results in, one or more of the following:

an increase in the number or activity, or degree of tumor infiltration, of cytotoxic T-lymphocytes and/or natural killer cells;

an increase in the number or activity of M1 macrophages in the tumor microenvironment and/or a decrease in the in the number or activity of M2 macrophages in the tumor microenvironment;

a decrease in the number or activity of regulatory T cells; and a decrease in the number or activity of myeloid-derived suppressor cells.

Also provided herein is a compound as disclosed herein for use as a medicament.

Also provided herein is a compound as disclosed herein for use as a medicament for the treatment of a RIPK1-mediated disease.

Also provided is the use of a compound as disclosed herein as a medicament.

Also provided is the use of a compound as disclosed herein as a medicament for the treatment of a RIPK1-mediated disease.

Also provided is a compound as disclosed herein for use in the manufacture of a medicament for the treatment of a RIPK1-mediated disease.

Also provided is the use of a compound as disclosed herein for the treatment of a RIPK1-mediated disease.

Also provided herein is a method of inhibition of RIPK1 comprising contacting RIPK1 with a compound as disclosed herein, or a salt thereof.

Also provided herein is a method for achieving an effect in a patient comprising the administration of a therapeutically effective amount of a compound as disclosed herein, or a salt thereof, to a patient wherein the effect is chosen from cognition enhancement.

Also provided is a method of modulation of a RIPK1-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain saturated hydrocarbon radical containing from 1 to 20 carbon atoms. In certain embodiments, said alkyl will comprise from 1 to 10 carbon atoms. In further embodiments, said alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylene," as used herein, alone or in combination, refers to a straight chain saturated or unsaturated hydrocarbon attached at two positions, such as methylene (—CH$_2$—), ethylene (—CH$_2$CH$_2$—), and propylene (—CH$_2$CH$_2$CH$_2$—). "Alkylene" thus consists of units chosen from —CH$_2$— and —CH=. Representative alkylenes include —CH$_2$—, —CH$_2$CH$_2$—, —CH=CH—, —CH$_2$CH$_2$CH$_2$—, —CH$_2$CH=CH—, and —CH=CH—CH=CH—. Alkylenes can be characterized by the count of atoms in the chain; thus, the representative alkylenes have 1, 2, 2, 3, 3, and 4 atoms, respectively.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, when alone, refer to an amino group as described below attached to the parent molecular moiety through a carbonyl group, or vice versa. The terms "amido" and "carbamoyl," as used herein, when in combination, refer to either of —C(O)NH— and —NHC(O)—. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH₃C(O)NH—).

The term "amino," as used herein, alone or in combination, refers to —NRR' wherein R and R' are independently chosen from hydrogen, alkyl, acyl, heteroalkyl, aryl, cycloalkyl, heteroaryl, and heterocycloalkyl, any one of which may themselves be optionally substituted. Additionally, R and R' may combine to form heterocycloalkyl, either of which is optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. The term embraces polycyclic ring systems which comprise at least one nonaromatic ring, such as 1,2,3,4-tetrahydronaphthalene, 9,10-dihydroanthracene, 9,10-dihydrophenanthrene, and 7,8,9,10-tetrahydrobenzo[α]pyrene (7,8,9,10-tetrahydrobenzo[pqr]tetraphene). The term does not embrace polycyclic aromatic ring systems such as naphthalene, anthracene, phenanthrene, and benzo[α]pyrene (benzo[pqr]tetraphene). In certain embodiments, said cycloalkyl will comprise from 5 to 7 carbon atoms. In certain embodiments, said cycloalkyl will comprise a spirocycle ring system. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and one, two, or three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroalkylene," as used herein, alone or in combination, refers to an alkylene in which either one or both of the following hold: (a) one or more —CH$_2$— groups is substituted with —NH— groups, and/or (b) one or more —CH= groups is substituted with —N=groups. Representative heteroalkylenes include —CH$_2$NH—, —CH=NH—, —NHCH$_2$CH$_2$—, —CH$_2$NHCH$_2$—, —NHCH=CH—, —NHCH$_2$CH$_2$CH$_2$—, —CH=CH—N=CH, and —CH=CH—CH=N—. As with alkylenes, heteroalkylenes can be characterized by the count of atoms in the chain; thus, the representative alkylenes have 2, 2, 3, 3, 3, 4, 4, and 4 atoms, respectively.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings wherein heteroaryl rings are fused with other heteroaryl rings wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridinyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member wherein each said heteroatom may be independently chosen from nitrogen, oxygen, and sulfur. The term embraces polycyclic ring systems which comprise at least one nonaromatic ring, such as indoline, 2,3-dihydrobenzofuran, 1,2-dihydroquinoline, 1,4-dihydroquinoline, and 9,10-dihydroacridine. The term does not embrace polycyclic aromatic ring systems such as indole, benzofuran, quinoline, and acridine. In certain embodiments, said heterocycloalkyl will comprise a spirocycle ring system. Examples of such spiro heterocycloalkyls include 2,6-dioxaspiro[3.3]heptane, 5,8-dioxa-2-azaspiro[3.4]octane, and 7-oxa-2-azaspiro[3.5]nonane. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups is optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which is optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR' wherein R and R' are independently chosen from hydrogen and lower alkyl, either of which is optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(=O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

For clarity, parentheses may be used to identify the connectivity of substituents. For example (alkyl)aryl refers to an aryl group which is substituted with an alkyl group. Likewise, ((aryl)alkyl)aryl refers to an aryl group which is substituted by an alkyl group, said alkyl group being substituted with an aryl group. In contrast, (aryl)(cycloalkyl) alkyl refers to an alkyl group which is substituted with both (a) an aryl group, and (b) a cycloalkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any one of which is optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

A "cognitive disorder," as used herein refers to a mental health disorder in which loss of cognitive function is the primary symptom, and which primarily affects learning, memory, perception, and/or problem solving. Cognitive disorders include amnesia, dementia, and delirium. Causes may include damage to the memory portions of the brain, whether from trauma or chemotherapy.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"RIPK1 binder" is used herein to refer to a compound that exhibits an $K_d$ with respect to RIPK1 of no more than about 100 µM and more typically not more than about 50 µM, as measured in the RIPK1 binding assay described generally herein. The RIPK1 binding assay measures the $K_d$ (dissociation constant) for the binding of a compound with the active site of RIPK1. Certain compounds disclosed herein have been discovered to bind to RIPK1. In certain embodiments, compounds will exhibit an $K_d$ with respect to RIPK1 of no more than about 10 µM; in further embodiments, compounds will exhibit a $K_d$ with respect to RIPK1 of no more than about 1 µM; in yet further embodiments, compounds will exhibit a $K_d$ with respect to RIPK1 of not more than about 0.1 µM; in yet further embodiments, compounds will exhibit a $K_d$ with respect to RIPK1 of not more than about 10 nM, as measured in the RIPK1 assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts and Polymorphs

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

Formulations

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Administration and Treatment

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with: donepezil, rivastigmine, galantamine, and memantine. Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-glycnacase inhibitors, and other medicines approved for the treatment of Alzheimer's disease. Further examples include metformin, minocycline, tissue plasminogen activator, and other therapies that improve neuronal survival.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating RIPK1-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of RIPK1-mediated disorders.

In a related aspect, certain embodiments provide methods for the treatment of cancer that comprise the coadministration of another therapeutic agent. In some embodiments, the other therapeutic agent is a checkpoint inhibitor. In some embodiments, the other therapeutic agent is chosen from an anti-PD1 inhibitor, an anti-PDL1 inhibitor, an anti-CTLA4 inhibitor, an anti-OX50 inhibitor, an anti-TIM3 inhibitor, and an anti-LAG3 inhibitor.

For use in cancer and neoplastic diseases a RIPK1 inhibitor may be optimally used together with one or more of the following non-limiting examples of anti-cancer agents:

1) inhibitors or modulators of a protein involved in one or more of the DNA damage repair (DDR) pathways such as:
    a. PARP1/2, including, but not limited to: olaparib, niraparib, rucaparib;
    b. checkpoint kinase 1 (CHK1), including, but not limited to: UCN-01, AZD7762, PF477736, SCH900776, MK-8776, LY2603618, V158411, and EXEL-9844;
    c. checkpoint kinase 2 (CHK2), including, but not limited to: PV1019, NSC 109555, and VRX0466617;
    d. dual CHK1/CHK2, including, but not limited to: XL-844, AZD7762, and PF-473336;
    e. WEE1, including, but not limited to: MK-1775 and PD0166285;
    f. ATM, including, but not limited to KU-55933,
    g. DNA-dependent protein kinase, including, but not limited to NU7441 and M3814; and
    h. Additional proteins involved in DDR;
2) Inhibitors or modulators of one or more immune checkpoints, including, but not limited to:
    a. PD-1 inhibitors such as nivolumab (OPDIVO), pembrolizumab (KEYTRUDA), pidilizumab (CT-011), and AMP-224 (AMPLIMMUNE);
    b. PD-L1 inhibitors such as Atezolizumab (TECENTRIQ), Avelumab (Bavencio), Durvalumab (Imfinzi), MPDL3280A (Tecentriq), BMS-936559, and MEDI4736;
    c. anti-CTLA-4 antibodies such as ipilimumab (YERVOY) and CP-675,206 (TREMELIMUMAB);
    d. inhibitors of T-cell immunoglobulin and mucin domain 3 (Tim-3);

e. inhibitors of V-domain Ig suppressor of T cell activation (Vista);
f. inhibitors of band T lymphocyte attenuator (BTLA);
g. inhibitors of lymphocyte activation gene 3 (LAG3); and
h. inhibitors of T cell immunoglobulin and immunoreceptor tyrosine-based inhibitory motif domain (TIGIT);

3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotic, which are often plant alkaloids and terpenoids, or derivatives thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);
8) topoisomerase inhibitors, including, but not limited to: amacrine, camptothecin (CTP), genistein, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;
11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin;
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);
15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide (NILANDRON);
17) tyrosine kinase inhibitors, including, but not limited to: imatinib (GLEEVEC), erlotinib (TARCEVA), lapatininb (TYKERB), sorafenib (NEXAVAR), and axitinib (INLYTA);
18) mTOR inhibitors, including, but not limited to: everolimus, temsirolimus (TORISEL), and sirolimus;
19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
    a. tetracyclines, including, but not limited to: doxycycline;
    b. erythromycins, including, but not limited to: azithromycin;
    c. glycylglycines, including, but not limited to: tigecycline;
    d. antiphrastic, including, but not limited to: pyrvinium pamoate;
    e. beta-lactams, including, but not limited to the penicillins and cephalosporins;
    f. anthracycline antibiotics, including, but not limited to: daunorubicin and doxorubicin;
    g. other antibiotics, including, but not limited to: chloramphenicol, mitomycin C, and actinomycin;
24) antibody therapeutic agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and
25) other agents, such as Bacillus Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In certain embodiments, the compounds, compositions, and methods disclosed herein may be useful for the treatment of a disorder associated with an inflammatory component of cellular stress. In certain embodiments, the disorder is chosen from multiple sclerosis, Neimanm-Pick disease, Alzheimers disease, Parkinson's disease, amyotrophic lateral sclerosis, Lewy body dementia, frontotemporal dementia, glutamine expansion diseases such as Huntington's disease, Kennedy's disease, and spinocerebellar ataxia In certain embodiments, the compounds, compositions, and methods disclosed herein may be useful for the treatment of neuropathy. In certain embodiments, the neuropathy is chosen from diabetic neuropathy and chemotherapy induced neuropathy.

In certain embodiments, the compounds, compositions, and methods disclosed herein may be useful for the treatment of a retinal disease. In certain embodiments, the retinal disease is chosen from macular degeneration and retinitis.

In certain embodiments, the compounds, compositions, and methods disclosed herein may be useful for the treatment of an injury to the CNS. In certain embodiments, the injury is chosen from a traumatic brain injury and stroke.

In certain embodiments, the compounds, compositions, and methods disclosed herein may be useful for the treatment of an autoimmune disorder. In certain embodiments, the autoimmune disorder is chosen from ulcerative colitis, rheumatoid arthritis, psoriasis, lupus, inflammatory bowel disease.

In certain embodiments, the compounds, compositions, and methods disclosed herein may be useful for the treatment of viral infections.

In certain embodiments, the compounds, compositions, and methods disclosed herein may be useful for the treatment of sepsis.

In certain embodiments, the compounds, compositions, and methods disclosed herein may be useful for the treatment of retinal degeneration.

In certain embodiments, the compounds, compositions, and methods disclosed herein may be useful for the treatment of ischemic stroke.

In certain embodiments, the compounds, compositions, and methods disclosed herein may be useful for the treatment of intracerebral hemorrhage.

In certain embodiments, the compounds, compositions, and methods disclosed herein may be useful for the treatment of amyotrophic lateral sclerosis.

In certain embodiments, the compounds, compositions, and methods disclosed herein may be useful for the treatment of an acute kidney injury.

In certain embodiments, the compounds, compositions, and methods disclosed herein may be useful for the treatment of a myocardial reperfusion injury.

In certain embodiments, the compounds, compositions, and methods disclosed herein may be useful for the treatment of Alzheimer's disease.

In certain embodiments, the compounds, compositions, and methods disclosed herein may be useful for the treatment of ulcerative colitis.

In certain embodiments, the compounds, compositions, and methods disclosed herein may be useful for the treatment of osteoarthritis.

In certain embodiments, the compounds, compositions, and methods disclosed herein may be coadministered with another therapeutic agent.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; Bu=butyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCM=dichloromethane; DEAD=diethyl azodicarboxylate; DtBAD=di-t-butyl azodicarboxylate; DIBAL-H=di-isobutyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; dppf=1,1'-bis(diphenylphosphino)ferrocene; EDC·HCl=EDCI·HCl=1-ethyl-3-(3-dimethylaminopropyl) carbodiimide hydrochloride; Et=ethyl; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; IBX=2-iodoxybenzoic acid; iPr=i-Pr=isopropyl=2-propyl; iPrOH=i-PrOH=isopropanol; LAH=lithium aluminiumhydride; LDA=lithium diisopropyl amide; LiHMDS=Lithium bis(trimethylsilyl)amide; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tert-butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; $Pd(Ph_3)_4$=tetrakis(triphenylphosphine)palladium(0); $Pd_2(dba)_3$=tris(dibenzylideneacetone)dipalladium(0); $PdCl_2(PPh_3)_2$=bis(triphenylphosphine)palladium(II) dichloride; PG=protecting group; Ph=phenyl; prep-HPLC=preparative high-performance liquid chromatography; PMBCl=para-methoxybenzyl; PMBCl=para-methoxybenzyl chloride; PMBOH=para-methoxybenzyl alcohol; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; tBuOH=tBuOH=tert-butanol; $T_3P$=Propylphosphonic Anhydride; TEA=$Et_3N$=triethylamine; TFA=trifluoroacetic acid; TFAA=trifluoroacetic anhydride; THF=tetrahydrofuran; TIPS=triisopropylsilyl; Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

The following schemes can be used to practice the present invention.

Scheme I

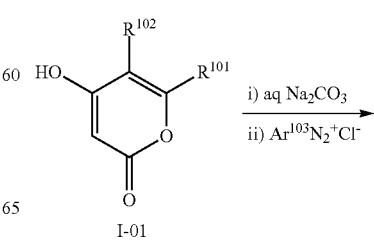

i) aq $Na_2CO_3$
ii) $Ar^{103}N_2^+Cl^-$

I-01

-continued

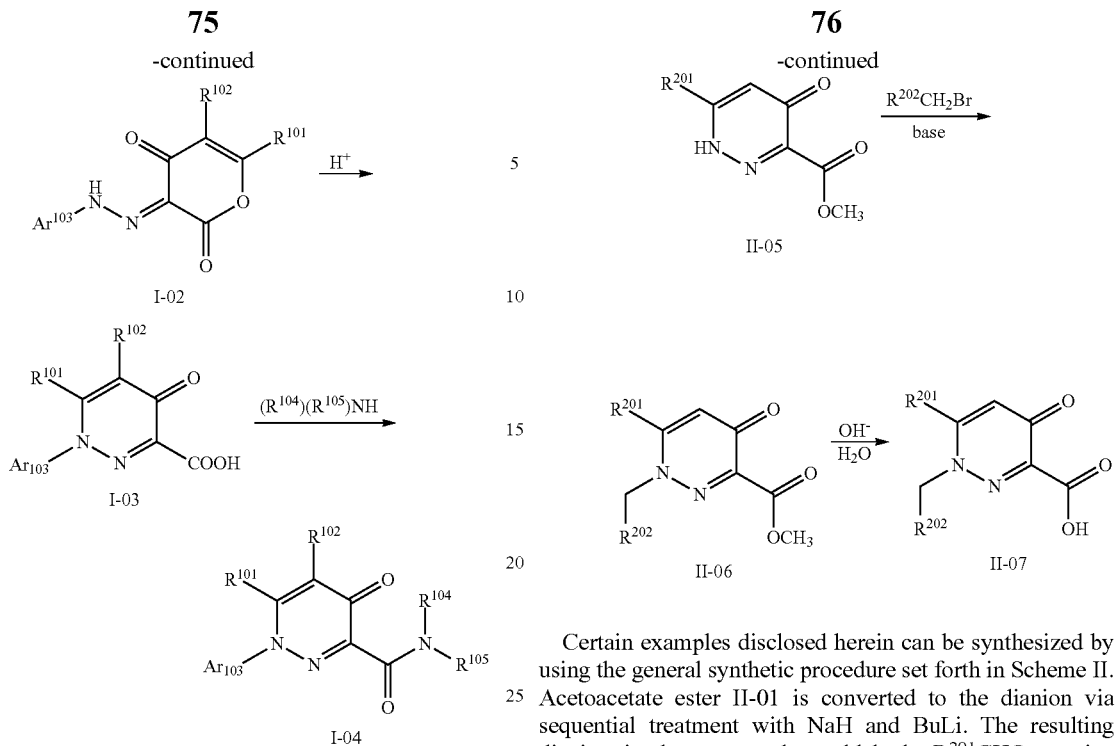

Certain examples disclosed herein can be synthesized by using the general synthetic procedure set forth in Scheme I. Pyranone I-01 can be reacted with a suitable aryldiazonium salt to provide hydrazone I-02. Acid-catalyzed ring cleavage/rearrangement leads to pyridazone I-03. Couping of amine $(R^{104})(R^{105})NH$ with the free carboxylic acid of I-03, in the presence of a suitable coupling agent, such as HATU, provides amide I-04.

Certain examples disclosed herein can be synthesized by using the general synthetic procedure set forth in Scheme II. Acetoacetate ester II-01 is converted to the dianion via sequential treatment with NaH and BuLi. The resulting dianion is then exposed to aldehyde $R^{201}CHO$ to give hydroxy compound II-02. The active methylene is converted to the diazo functionality of II-04 by reaction with arylsulfonyl azide II-03, or a similar reagent. Oxidation of the secondary alcohol to the ketone (not shown) is followed by ring-forming condensation to pyridazone II-05. Alkylation affords highly substituted compound II-06. The ester can then be hydrolyzed to provide carboxylic acid, which is carried forth by the steps disclosed in Scheme I.

Scheme II

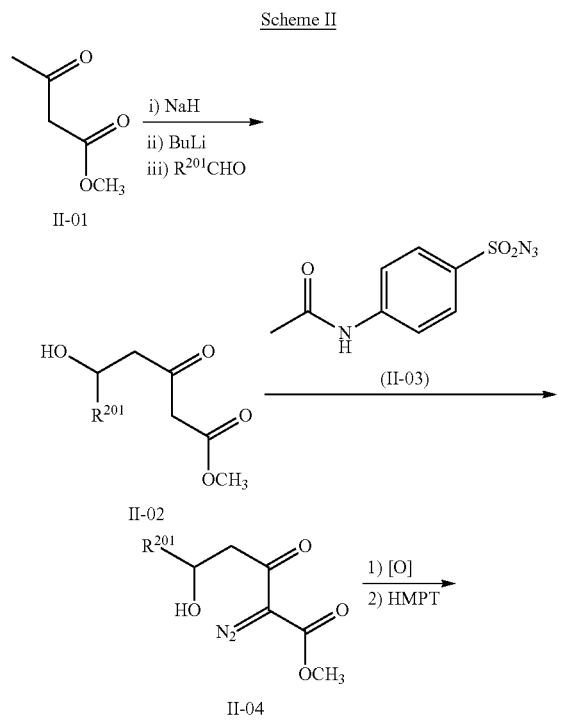

Scheme III

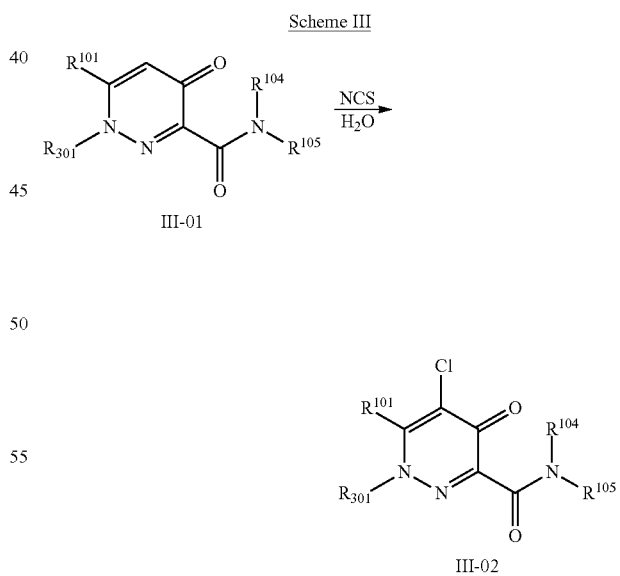

Certain examples disclosed herein can be synthesized by using the general synthetic procedure set forth in Scheme III. Enone III-01, as provided from Scheme I or Scheme II, or from another sequence apparent to a person skilled in the art, can be oxidatively chlorinated to provided chloro compound III-02.

Scheme IV

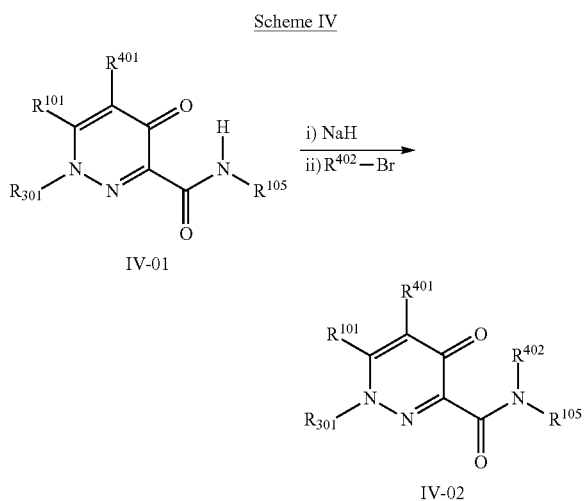

Certain examples disclosed herein can be synthesized by using the general synthetic procedure set forth in Scheme IV. Secondary amide IV-01, as provided from any one of Scheme I, II, or III, or from another sequence apparent to a person skilled in the art, can be deprotonated with NaH or a comparable base, followed by alkylation with $R^{402}$—Br, or a different suitable alkylating agent, to afford tertiary amide IV-02.

Scheme V

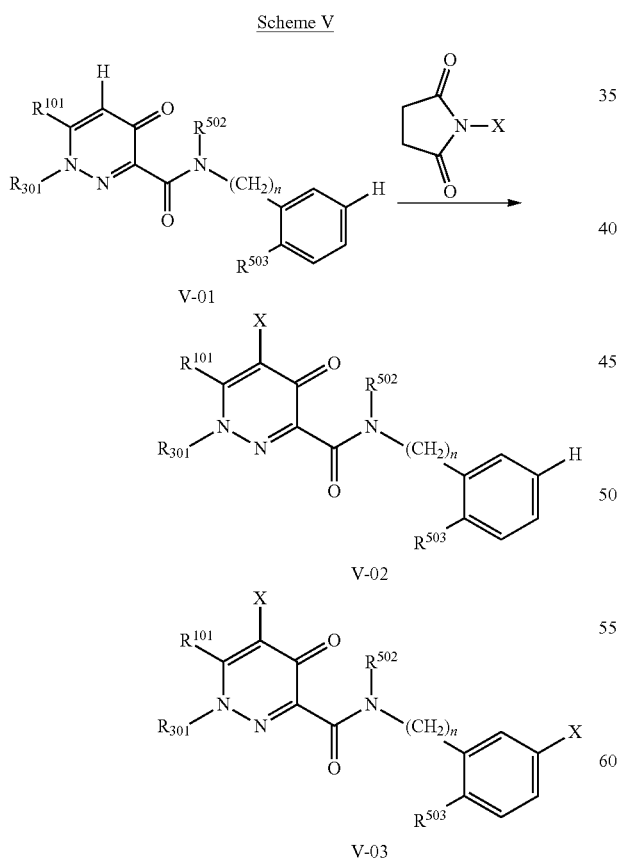

Certain examples disclosed herein can be synthesized by using the general synthetic procedure set forth in Scheme V.

Amide V-01, as provided from any one of Scheme I, II, and IV, or from another sequence apparent to a person skilled in the art, can be reacted with halo succinimide (X=Br, Cl) to give monohalogenated compound V-02 and/or dihalogenated compound V-03. In some embodiments. halogenation of the pendant phenyl group is promoted by an activating group $R^{503}$. In some embodiments, the activating group $R^{503}$ is an amine or amide. In some embodiments, group $R^{503}$ combines with $R^{502}$ to form a ring. It will be appreciated that other aryl groups, other than the phenyl group shown in V-01 above, can also be halogenation by use of this procedure. Procedures to separate the mono- and dihalogenated compounds V-02 and V-03 will be apparent to a person of skill.

The invention is further illustrated by the following examples.

Example 1

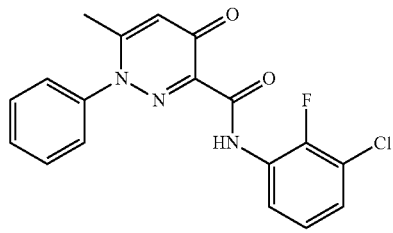 [SMILES: Cc1cc(=O)c(C(=O)Nc2cccc(Cl)c2F)nn1-c1ccccc1]

N-(3-chloro-2-fluorophenyl)-6-methyl-4-oxo-1-phenyl-1,4-dihydropyridazine-3-carboxamide

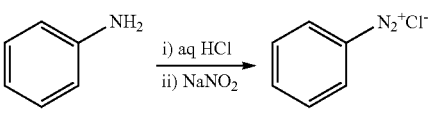

Benzenediazonium chloride To a solution of aniline (3.18 g, 32.49 mmol, 3.11 mL, 1 eq) in $H_2O$ (15 mL) was added HCl (12.75 g, 129.39 mmol, 12.50 mL, 37% purity, 3.98 eq), to the mixture was added a solution of $NaNO_2$ (2.38 g, 34.42 mmol, 1.06 eq) in $H_2O$ (8 mL) at 5° C., the mixture was stirred at 5° C. for 5 mins. Benzenediazonium chloride was obtained as a yellow solution and used for next step directly.

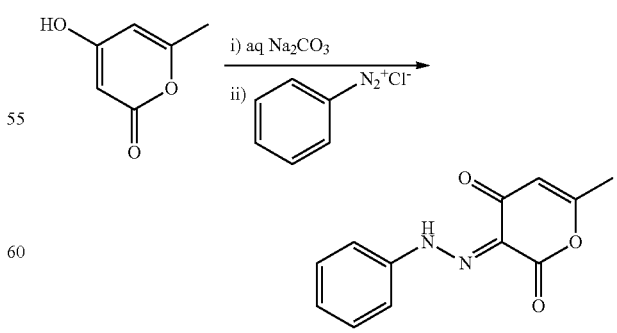

(E)-6-methyl-3-(2-phenylhydrazineylidene)-2H-pyran-2,4(3H)-dione To a solution of 4-hydroxy-6-methyl-2H-pyran-2-one (3.94 g, 31.24 mmol, 1 eq) in $H_2O$ (125 mL)

was added Na$_2$CO$_3$ (3.31 g, 31.24 mmol, 1 eq), the mixture was stirred at 0° C. for 5 mins, to the mixture was added the solution of benzenediazonium chloride prepared as indicated in the previous step, and the mixture was stirred at 5° C. for 5 mins. To the mixture was added NaOH (1 N, 20 mL) and the pH was adjusted to 9, the mixture was filtered and the filter cake was washed with water (20 mL×3) and then dried under reduced pressure to afford (3E)-6-methyl-3-(phenylhydrazono)pyran-2,4-dione (7 g, 30.41 mmol, 97% yield, 100% purity) as a yellow solid.

MS(ES+)C$_{12}$H$_{10}$N$_2$O$_3$ requires: 230, found 231 [M+H]$^+$.

$^1$H NMR (400 MHz, DMSO-d$_6$) δ=7.68 (d, J=7.9 Hz, 2H), 7.52 (t, J=7.9 Hz, 2H), 7.43-7.30 (m, 1H), 6.04 (s, 1H), 2.21 (s, 3H).

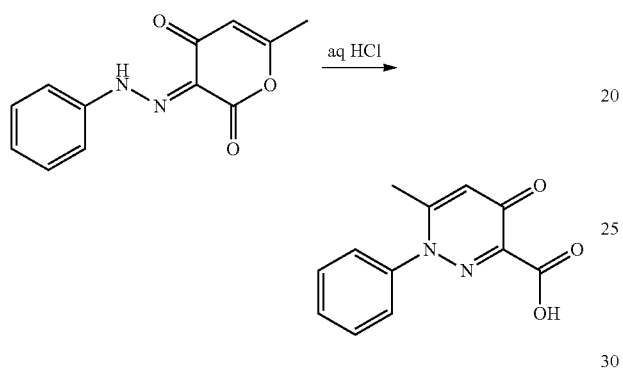

6-methyl-4-oxo-1-phenyl-1,4-dihydropyridazine-3-carboxylic acid (Intermediate I) To a flask was added the product from the previous step (7 g, 30.41 mmol, 1 eq) and HCl (250 mL), the mixture was stirred at 100° C. for 16 hours. The reaction mixture was filtered and the filter cake was washed with MTBE (30 mL×3) and dried under reduced pressure to afford the title compound (6.3 g, 27.37 mmol, 90% yield).

MS(ES+)C$_{12}$H$_{10}$N$_2$O$_3$ requires: 230, found 229 [M−H]$^-$.

$^1$H NMR (400 MHz, DMSO-d$_6$) δ=7.66-7.59 (m, 5H), 7.14 (s, 1H), 2.24 (s, 3H).

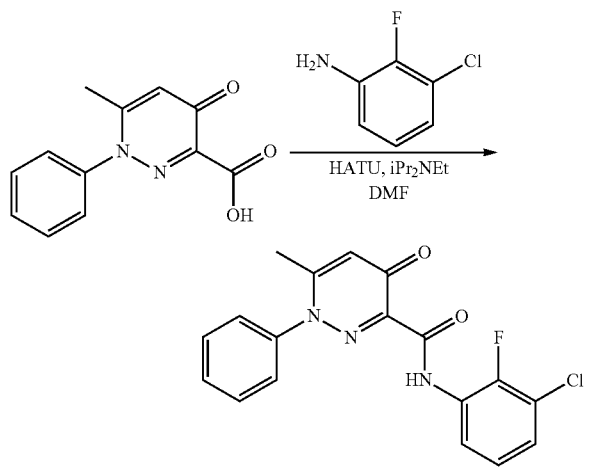

N-(3-chloro-2-fluorophenyl)-6-methyl-4-oxo-1-phenyl-1,4-dihydropyridazine-3-carboxamide (Example 1) To a solution of the product from the previous step (0.3 g, 1.30 mmol, 1 eq) in DMF (5 mL) was added HATU (741.45 mg, 1.95 mmol, 1.5 eq), DIPEA (504.04 mg, 3.90 mmol, 679.29 uL, 3 eq) and 3-chloro-2-fluoro-aniline (283.85 mg, 1.95 mmol, 1.5 eq), the mixture was stirred at 25° C. for 16 hours. To the mixture was added water (5 mL) and extracted with DCM (5 mL×3), the organic phase was washed with brine (10 mL×2), dried over Na$_2$SO$_4$, filtered and concentrated under reduced pressure to give a residue which was purified by prep-HPLC (column: Phenomenex Synergi C18 150*25 mm*10 um; mobile phase: [water (0.225% FA)-ACN]; B %: 45%-75%, 11 min), the eluent was concentrated to afford the title compound (29.5 mg, 79.16 umol, 6% yield) as a white solid.

MS(ES+)C$_{18}$H$_{13}$N$_3$O$_2$FCl requires: 357, found 358 [M+H]$^+$.

$^1$H NMR (400 MHz, CHLOROFORM-d) δ=12.80 (br s, 1H), 8.44-8.40 (m, 1H), 7.54-7.43 (m, 3H), 7.38-7.28 (m, 2H), 7.12-6.97 (m, 2H), 6.74 (s, 1H), 2.20 (s, 3H).

Example 2

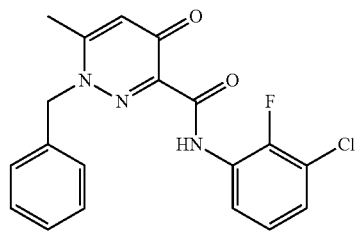 [SMILES: Cc1cc(=O)c(C(=O)Nc2cccc(Cl)c2F)nn1Cc1ccccc1]

1-Benzyl-N-(3-chloro-2-fluorophenyl)-6-methyl-4-oxo-1,4-dihydropyridazine-3-carboxamide

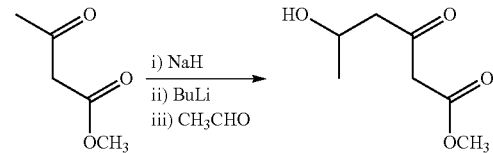

Methyl 5-hydroxy-3-oxohexanoate To a suspension of NaH (2.07 g, 51.67 mmol, 60% purity, 1.2 eq) in THF (100 mL) was added methyl 3-oxobutanoate (5, 43.06 mmol, 4.63 mL, 1 eq) at 0° C., and the mixture was stirred at 0° C. for 0.5 hour. To the mixture was then added n-BuLi (2.5 M, 20.67 mL, 1.2 eq) dropwise, the mixture was stirred at 0° C. for 0.5 hour. To the mixture was then added acetaldehyde (2.00 g, 43.06 mmol, 2.54 mL, 1 eq), and the mixture was stirred at 25° C. for 1 hour. To the mixture was added saturated aqueous NH$_4$Cl (100 mL) and extracted with EtOAc (100 mL×3), dried over Na$_2$SO$_4$, filtered and concentrated under reduced pressure. The residue was purified by column chromatography (SiO$_2$, Petroleum ether/Ethyl acetate=25/1 to 10/1) to afford the title compound (1.2 g, 7.49 mmol, 17% yield) as light yellow oil. $^1$H NMR (400 MHz, CDCl$_3$) δ=4.22-4.18 (m, 1H), 3.68 (s, 3H), 3.43 (s, 2H), 2.66-2.54 (m, 2H), 1.15 (d, J=6.4 Hz, 3H).

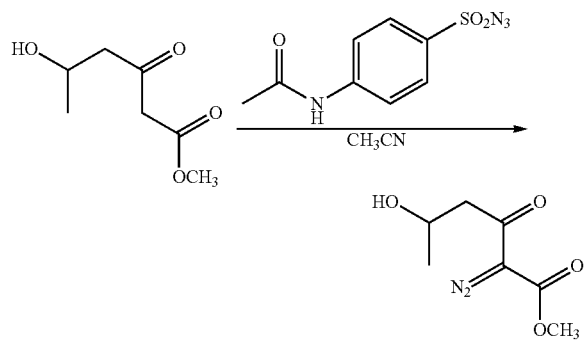

Methyl 2-diazo-5-hydroxy-3-oxohexanoate To a solution of the product from the previous step (1.2 g, 7.49 mmol, 1 eq) in MeCN (50 mL) was added Et$_3$N (985.57 mg, 9.74 mmol, 1.36 mL, 1.3 eq) and N-(4-azidosulfonylphenyl)acetamide (1.80 g, 7.49 mmol, 1 eq) at 0° C., the mixture was stirred at 0° C. for 2 hours. The mixture was filtered and concentrated under reduced pressure to give a residue which was purified by column chromatography (SiO$_2$, Petroleum ether/Ethyl acetate=15/1 to 5/1) to afford the title compound (0.733 g, 3.54 mmol, 47% yield) as a yellow oil.

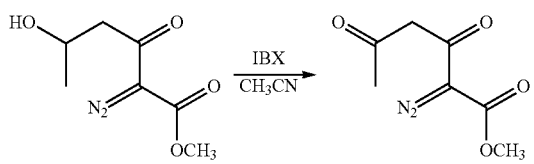

Methyl 2-diazo-3,5-dioxohexanoate To a solution of the product from the previous step (0.733 g, 3.54 mmol, 1 eq) in MeCN (10 mL) was added IBX (1.29 g, 4.61 mmol, 1.3 eq) at 0° C., the mixture was warmed to 82° C. and stirred for 2 hours. The mixture was filtered and the filtrate was concentrated under reduced pressure to afford the title compound (0.69 g, 3.37 mmol, 95% yield) as a yellow oil.

$^1$H NMR (400 MHz, CDCl$_3$) δ=3.90 (s, 2H), 3.75 (s, 3H), 2.21 (s, 3H).

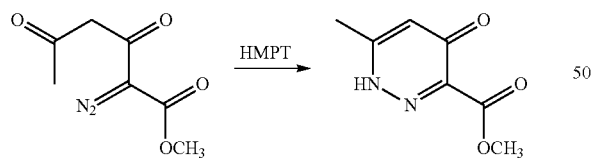

Methyl 6-methyl-4-oxo-1,4-dihydropyridazine-3-carboxylate To a solution of the product from the previous step (613.33 mg, 3.00 mmol, 1 eq) in DCM (30 mL) was added HMPT (489.20 mg, 3.00 mmol, 544.77 uL, 1 eq) at 0° C., the mixture was stirred at 25° C. for 16 hours. The reaction mixture was concentrated under reduced pressure to remove solvent then purified by prep-HPLC (column: Waters Xbridge C18 150*50 mm*10 um; mobile phase: [water (10 mM NH$_4$HCO$_3$)-ACN]; B %: 1%-8%, 11.5 min), the eluent was concentrated and freeze dried to afford the title compound (0.333 g, 1.80 mmol, 60% yield) as a yellow solid. MS(ES+) C$_7$H$_8$N$_2$O$_3$ requires: 168, found: 169 [M+H]$^+$.

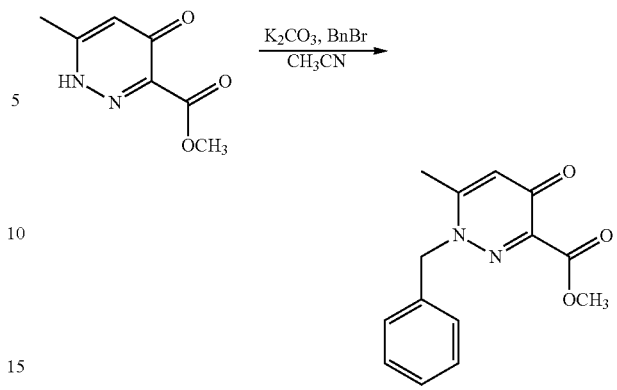

Methyl 1-benzyl-6-methyl-4-oxo-1,4-dihydropyridazine-3-carboxylate To a solution of benzyl bromide (338.20 mg, 1.98 mmol, 234.86 uL, 2.5 eq) in ACN (1 mL) was added K$_2$CO$_3$ (163.98 mg, 1.19 mmol, 1.5 eq) and the product from the previous step (0.133 g, 790.96 umol, 1 eq), the mixture was stirred at 80° C. for 5 hours. To the reaction mixture was added water (5 mL) and extracted with EtOAc (5 mL×3), dried over Na$_2$SO$_4$, filtered and concentrated under reduced pressure to give a residue which was purified by prep-TLC (SiO$_2$, Petroleum ether: Ethyl acetate=10:1) to afford the title compound (0.24 g) as yellow oil.

MS(ES+) C$_{14}$H$_{14}$N$_2$O$_3$ requires: 258, found 259 [M+H]$^+$.

$^1$H NMR (400 MHz, DMSO-d6) δ=7.43-7.38 (m, 2H), 7.37-7.33 (m, 1H), 7.23-7.16 (m, 2H), 6.55 (s, 1H), 5.41 (s, 2H), 3.82 (s, 3H), 2.33 (s, 3H). Note: HSQC spectral data shows benzylic carbon resonance <60 ppm, indicative of N-benzylation.

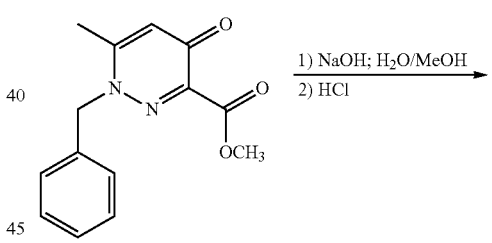

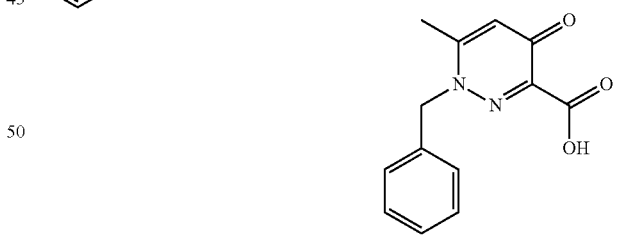

1-benzyl-6-methyl-4-oxo-1,4-dihydropyridazine-3-carboxylic acid To a solution of the product from the previous step (0.24 g, 929.25 umol, 1 eq) in MeOH (4.5 mL) and H$_2$O (1.5 mL) was added NaOH (44.60 mg, 1.12 mmol, 1.2 eq), the mixture was stirred at 25° C. for 16 hours. To the reaction mixture was added HCl (1N, 430 uL) and concentrated under reduced pressure to remove solvent and the residue was extracted with EtOAc (10 mL×3), filtered and filtrate was dried over Na$_2$SO$_4$, filtered and filtrate concentrated under reduced pressure to afford the title compound (0.085 g, 299.29 umol, 32% yield) as a white solid. MS(ES+) C$_{13}$H$_{12}$N$_2$O$_3$ requires: 244, found: 245 [M+H]$^+$.

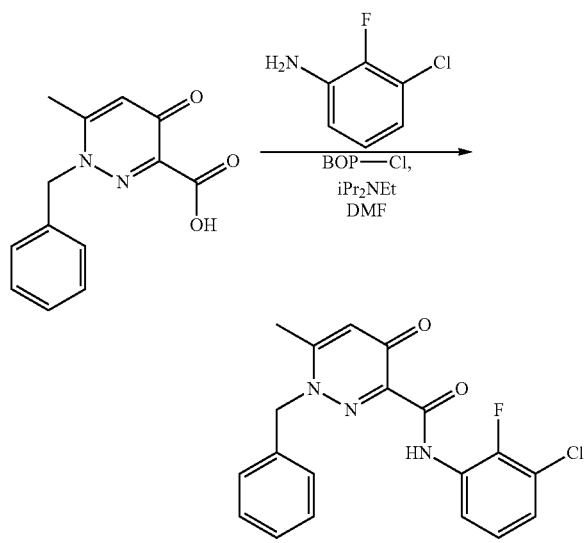

1-Benzyl-N-(3-chloro-2-fluoro-phenyl)-6-methyl-4-oxo-pyridazine-3-carboxamide To a solution of 3-chloro-2-fluoro-aniline (47.92 mg, 329.22 umol, 1.1 eq) in DCM (2 mL) was added the product from the previous step (0.085 g, 299.29 umol, 1 eq), BOP—Cl (114.29 mg, 448.93 umol, 1.5 eq) and DIPEA (116.04 mg, 897.87 umol, 156.39 uL, 3 eq), and the mixture was then stirred at 25° C. for 16 hours. To the mixture was added water (2 mL) and extracted with DCM (2 mL×3), the organic phase was washed with brine (5 mL×2), dried over $Na_2SO_4$, filtered and concentrated under reduced pressure. The residue was purified by prep-HPLC (column: Phenomenex Synergi C18 150*25*10 um; mobile phase: [water (0.1% TFA)-ACN]; B %: 50%-70%, 10 min), the eluent was concentrated and freeze dried to afford the title compound (8.7 mg, 22.70 umol, 7% yield) as a yellow solid.

MS(ES+) $C_{19}H_{15}N_3O_2FCl$ requires: 371, found: 372 $[M+H]^+$.

$^1$H NMR (400 MHz, $CDCl_3$) δ=12.88 (s, 1H), 8.56-8.36 (m, 1H), 7.34-7.26 (m, 3H), 7.17-7.12 (m, 2H), 7.11-6.99 (m, 2H), 6.64 (s, 1H), 5.48 (s, 2H), 2.32 (s, 3H).

TABLE 1

Examples 3-37

| Ex | Structure | Name | Calc/Obs'd mass (ES+) $[M + H]^+$ |
|---|---|---|---|
| 3 | 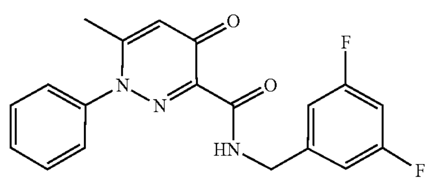 [SMILES: Cc1cc(=O)c(C(=O)NCc2cc(F)cc(F)c2)nn1-c1ccccc1] | N-(3,5-difluorobenzyl)-6-methyl-4-oxo-1-phenyl-1,4-dihydropyridazine-3-carboxamide | 355/356 |
| 4 | 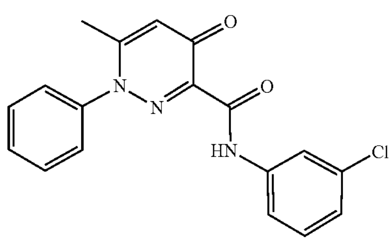 [SMILES: Cc1cc(=O)c(C(=O)Nc2cccc(Cl)c2)nn1-c1ccccc1] | N-(3-chlorophenyl)-6-methyl-4-oxo-1-phenyl-1,4-dihydropyridazine-3-carboxamide | 339/340 |
| 5 | 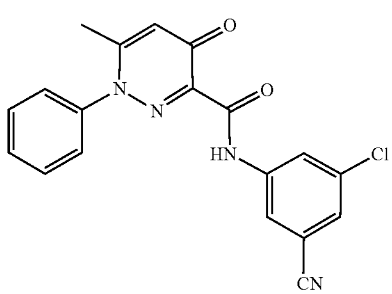 [SMILES: Cc1cc(=O)c(C(=O)Nc2cc(Cl)cc(C#N)c2)nn1-c1ccccc1] | N-(3-chloro-5-cyanophenyl)-6-methyl-4-oxo-1-phenyl-1,4-dihydropyridazine-3-carboxamide | 364/365 |

TABLE 1-continued

Examples 3-37

| Ex | Structure | Name | Calc/Obs'd mass (ES+) [M + H]+ |
|---|---|---|---|
| 6 | 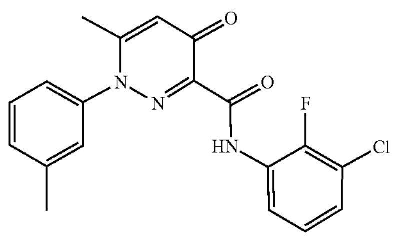 [SMILES: Cc1cccc(-n2nc(C(=O)Nc3cccc(Cl)c3F)c(=O)cc2C)c1] | N-(3-chloro-2-fluorophenyl)-6-methyl-4-oxo-1-(m-tolyl)-1,4-dihydropyridazine-3-carboxamide | 371/372 |
| 7 | 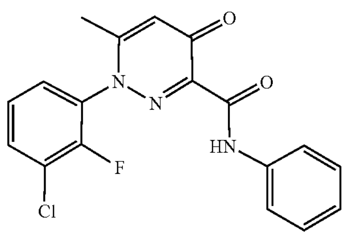 [SMILES: Cc1cc(=O)c(C(=O)Nc2ccccc2)nn1-c1cccc(Cl)c1F] | 1-(3-chloro-2-fluorophenyl)-6-methyl-4-oxo-N-phenyl-1,4-dihydropyridazine-3-carboxamide | 357/358 |
| 8 | 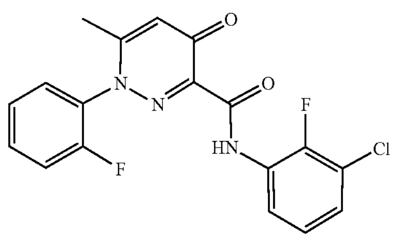 [SMILES: Cc1cc(=O)c(C(=O)Nc2cccc(Cl)c2F)nn1-c1ccccc1F] | N-(3-chloro-2-fluorophenyl)-1-(2-fluorophenyl)-6-methyl-4-oxo-1,4-dihydropyridazine-3-carboxamide | 375/376 |
| 9 | 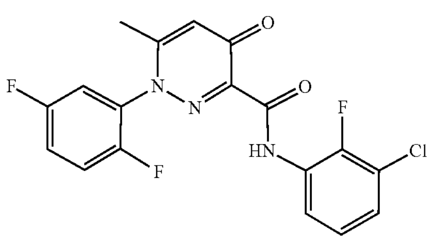 [SMILES: Cc1cc(=O)c(C(=O)Nc2cccc(Cl)c2F)nn1-c1cc(F)ccc1F] | N-(3-chloro-2-fluorophenyl)-1-(2,5-difluorophenyl)-6-methyl-4-oxo-1,4-dihydropyridazine-3-carboxamide | 393/394 |
| 10 | 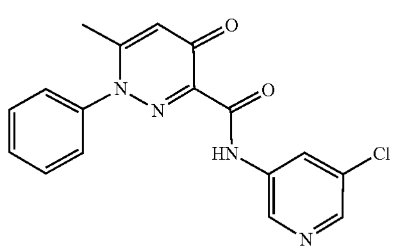 [SMILES: Cc1cc(=O)c(C(=O)Nc2cncc(Cl)c2)nn1-c1ccccc1] | N-(5-chloropyridin-3-yl)-6-methyl-4-oxo-1-phenyl-1,4-dihydropyridazine-3-carboxamide | 340/341 |
| 11 | 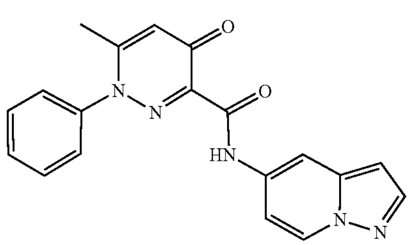 [SMILES: Cc1cc(=O)c(C(=O)Nc2ccn3nccc3c2)nn1-c1ccccc1] | 6-methyl-4-oxo-1-phenyl-N-(pyrazolo[1,5-a]pyridin-5-yl)-1,4-dihydropyridazine-3-carboxamide | 345/346 |

TABLE 1-continued

Examples 3-37

| Ex | Structure | Name | Calc/Obs'd mass (ES+) [M + H]+ |
|---|---|---|---|
| 12 | 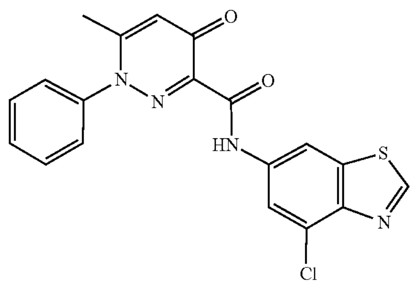 [SMILES: Cc1cc(=O)c(C(=O)Nc2cc(Cl)c3ncsc3c2)nn1-c1ccccc1] | N-(4-chlorobenzo[d]thiazol-6-yl)-6-methyl-4-oxo-1-phenyl-1,4-dihydropyridazine-3-carboxamide | 396/397 |
| 13 | 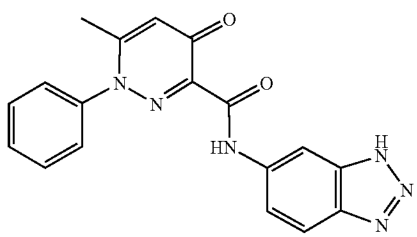 | N-(1H-benzo[d][1,2,3]triazol-6-yl)-6-methyl-4-oxo-1-phenyl-1,4-dihydropyridazine-3-carboxamide | 346/347 |
| 14 | 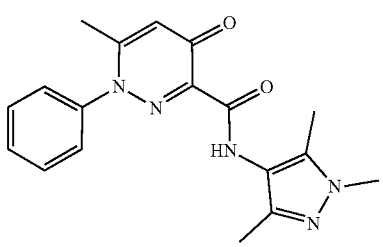 [SMILES: Cc1nn(C)c(C)c1NC(=O)c1nn(-c2ccccc2)c(C)cc1=O] | 6-methyl-4-oxo-1-phenyl-N-(1,3,5-trimethyl-1H-pyrazol-4-yl)-1,4-dihydropyridazine-3-carboxamide | 337/338 |
| 15 | 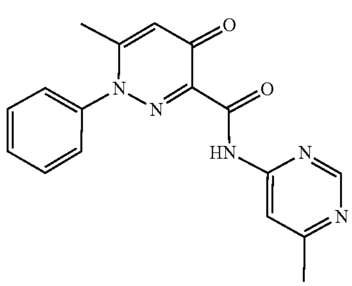 [SMILES: Cc1cc(NC(=O)c2nn(-c3ccccc3)c(C)cc2=O)ncn1] | 6-methyl-N-(6-methylpyrimidin-4-yl)-4-oxo-1-phenyl-1,4-dihydropyridazine-3-carboxamide | 321/322 |
| 16 | 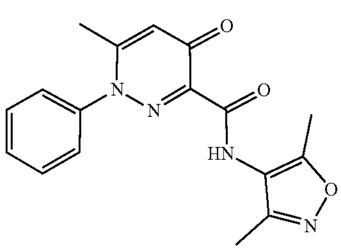 [SMILES: Cc1noc(C)c1NC(=O)c1nn(-c2ccccc2)c(C)cc1=O] | N-(3,5-dimethylisoxazol-4-yl)-6-methyl-4-oxo-1-phenyl-1,4-dihydropyridazine-3-carboxamide | 324/325 |

TABLE 1-continued

Examples 3-37

| Ex | Structure | Name | Calc/Obs'd mass (ES+) [M + H]+ |
|---|---|---|---|
| 17 | 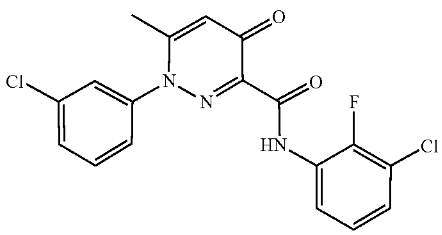 [SMILES: Cc1cc(=O)c(C(=O)Nc2cccc(Cl)c2F)nn1-c1cccc(Cl)c1] | N-(3-chloro-2-fluorophenyl)-1-(3-chlorophenyl)-6-methyl-4-oxo-1,4-dihydropyridazine-3-carboxamide | 391/392 |
| 18 | 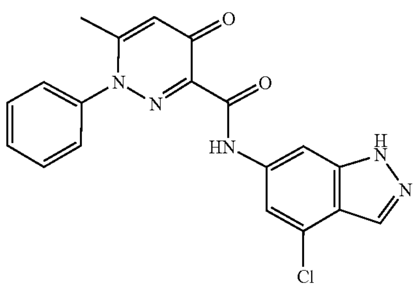 | N-(4-chloro-1H-indazol-6-yl)-6-methyl-4-oxo-1-phenyl-1,4-dihydropyridazine-3-carboxamide | 379/380 |
| 19 | 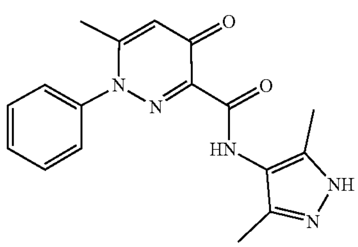 [SMILES: Cc1n[nH]c(C)c1NC(=O)c1nn(-c2ccccc2)c(C)cc1=O] | N-(3,5-dimethyl-1H-pyrazol-4-yl)-6-methyl-4-oxo-1-phenyl-1,4-dihydropyridazine-3-carboxamide | 323/324 |
| 20 | 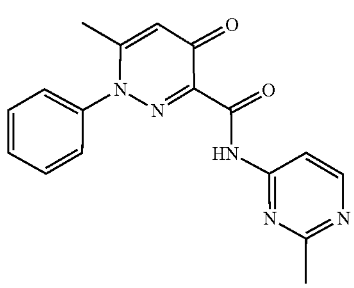 [SMILES: Cc1nccc(NC(=O)c2nn(-c3ccccc3)c(C)cc2=O)n1] | 6-methyl-N-(2-methylpyrimidin-4-yl)-4-oxo-1-phenyl-1,4-dihydropyridazine-3-carboxamide | 321/322 |
| 21 | 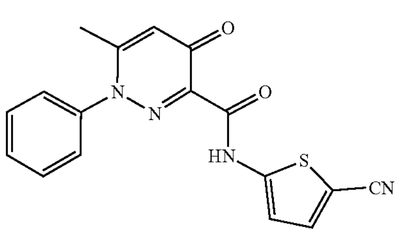 [SMILES: Cc1cc(=O)c(C(=O)Nc2ccc(C#N)s2)nn1-c1ccccc1] | N-(5-cyanothiophen-2-yl)-6-methyl-4-oxo-1-phenyl-1,4-dihydropyridazine-3-carboxamide | 336/337 |

TABLE 1-continued

Examples 3-37

| Ex | Structure | Name | Calc/Obs'd mass (ES+) [M + H]+ |
|---|---|---|---|
| 22 | 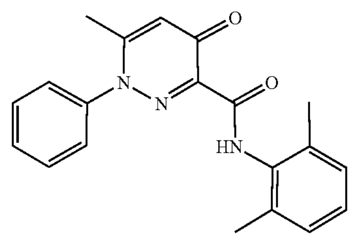 [SMILES: Cc1cccc(C)c1NC(=O)c1nn(-c2ccccc2)c(C)cc1=O] | N-(2,6-dimethylphenyl)-6-methyl-4-oxo-1-phenyl-1,4-dihydropyridazine-3-carboxamide | 333/334 |
| 23 | 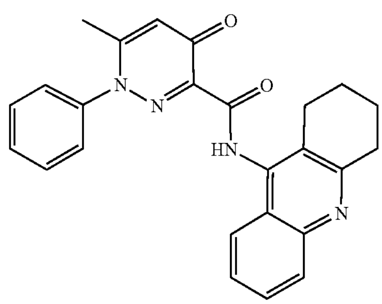 [SMILES: Cc1cc(=O)c(C(=O)Nc2c3c(nc4ccccc24)CCCC3)nn1-c1ccccc1] | 6-methyl-4-oxo-1-phenyl-N-(1,2,3,4-tetrahydroacridin-9-yl)-1,4-dihydropyridazine-3-carboxamide | 410/411 |
| 24 | 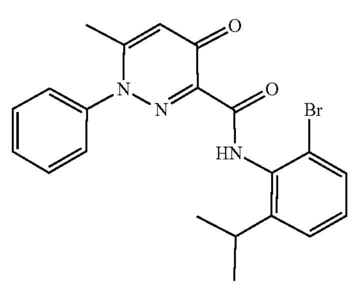 [SMILES: Cc1cc(=O)c(C(=O)Nc2c(Br)cccc2C(C)C)nn1-c1ccccc1] | N-(2-bromo-6-isopropylphenyl)-6-methyl-4-oxo-1-phenyl-1,4-dihydropyridazine-3-carboxamide | 425, 427/426, 428 |
| 25 | 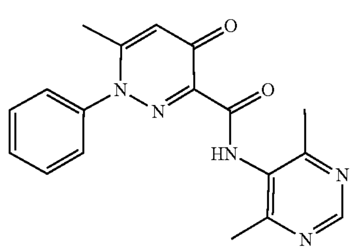 [SMILES: Cc1ncnc(C)c1NC(=O)c1nn(-c2ccccc2)c(C)cc1=O] | N-(4,6-dimethylpyrimidin-5-yl)-6-methyl-4-oxo-1-phenyl-1,4-dihydropyridazine-3-carboxamide | 335/336 |
| 26 | 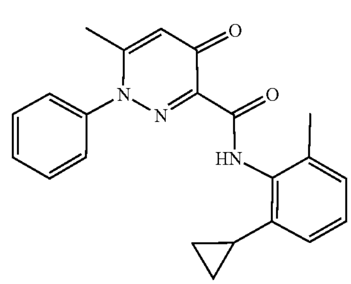 [SMILES: Cc1cccc(C2CC2)c1NC(=O)c1nn(-c2ccccc2)c(C)cc1=O] | N-(2-cyclopropyl-6-methylphenyl)-6-methyl-4-oxo-1-phenyl-1,4-dihydropyridazine-3-carboxamide | 359/360 |

TABLE 1-continued

Examples 3-37

| Ex | Structure | Name | Calc/Obs'd mass (ES+) [M + H]+ |
|---|---|---|---|
| 27 | 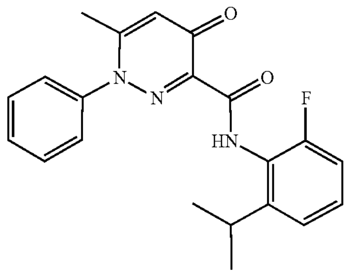 | N-(2-fluoro-6-isopropylphenyl)-6-methyl-4-oxo-1-phenyl-1,4-dihydropyridazine-3-carboxamide | 365/366 |
| 28 | 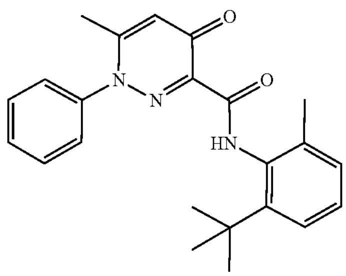 [SMILES: Cc1cccc(C(C)(C)C)c1NC(=O)c1nn(-c2ccccc2)c(C)cc1=O] | N-(2-(tert-butyl)-6-methylphenyl)-6-methyl-4-oxo-1-phenyl-1,4-dihydropyridazine-3-carboxamide | 375/376 |
| 29 | 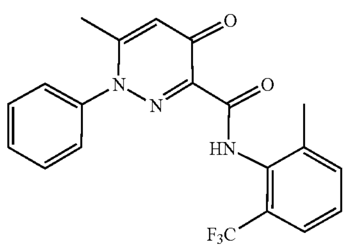 [SMILES: Cc1cccc(C(F)(F)F)c1NC(=O)c1nn(-c2ccccc2)c(C)cc1=O] | 6-methyl-N-(2-methyl-6-(trifluoromethyl)phenyl)-4-oxo-1-phenyl-1,4-dihydropyridazine-3-carboxamide | 387/388 |
| 30 | 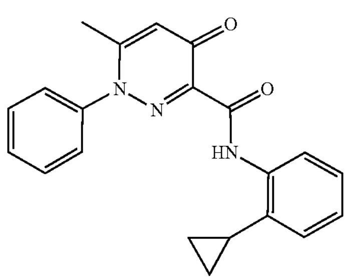 [SMILES: Cc1cc(=O)c(C(=O)Nc2ccccc2C2CC2)nn1-c1ccccc1] | N-(2-cyclopropylphenyl)-6-methyl-4-oxo-1-phenyl-1,4-dihydropyridazine-3-carboxamide | 345/346 |
| 31 | 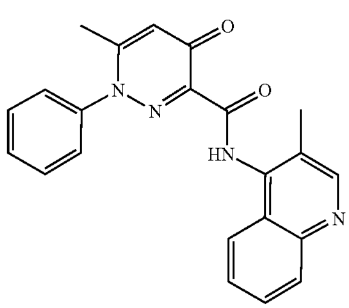 [SMILES: Cc1cnc2ccccc2c1NC(=O)c1nn(-c2ccccc2)c(C)cc1=O] | 6-methyl-N-(3-methylquinolin-4-yl)-4-oxo-1-phenyl-1,4-dihydropyridazine-3-carboxamide | 370/371 |

TABLE 1-continued

Examples 3-37

| Ex | Structure | Name | Calc/Obs'd mass (ES+) [M + H]⁺ |
|---|---|---|---|
| 32 | 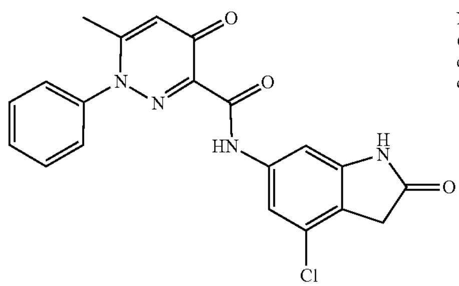 | N-(4-chloro-2-oxoindolin-6-yl)-6-methyl-4-oxo-1-phenyl-1,4-dihydropyridazine-3-carboxamide | 394/395 |
| 33 | 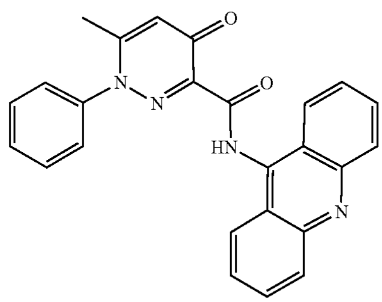 [SMILES: Cc1cc(=O)c(C(=O)Nc2c3ccccc3nc3ccccc23)nn1-c1ccccc1] | N-(acridin-9-yl)-6-methyl-4-oxo-1-phenyl-1,4-dihydropyridazine-3-carboxamide | 406/407 |
| 34 | 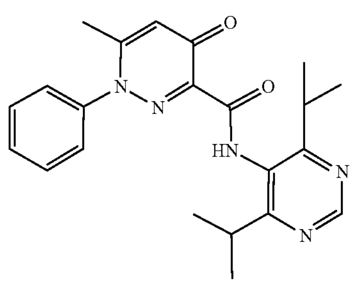 [SMILES: Cc1cc(=O)c(C(=O)Nc2c(C(C)C)ncnc2C(C)C)nn1-c1ccccc1] | N-(4,6-diisopropylpyrimidin-5-yl)-6-methyl-4-oxo-1-phenyl-1,4-dihydropyridazine-3-carboxamide | 391/392 |
| 35 | 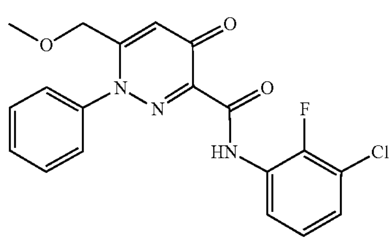 [SMILES: COCc1cc(=O)c(C(=O)Nc2cccc(Cl)c2F)nn1-c1ccccc1] | N-(3-chloro-2-fluorophenyl)-6-(methoxymethyl)-4-oxo-1-phenyl-1,4-dihydropyridazine-3-carboxamide | 387/388 |
| 36 | 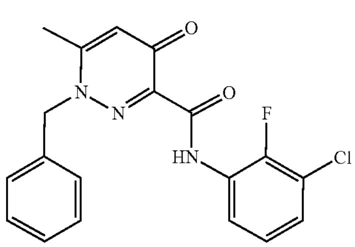 [SMILES: Cc1cc(=O)c(C(=O)Nc2cccc(Cl)c2F)nn1Cc1ccccc1] | | 371/372 |

TABLE 1-continued

Examples 3-37

| Ex | Structure | Name | Calc/Obs'd mass (ES+) [M + H]+ |
|---|---|---|---|
| 37 | 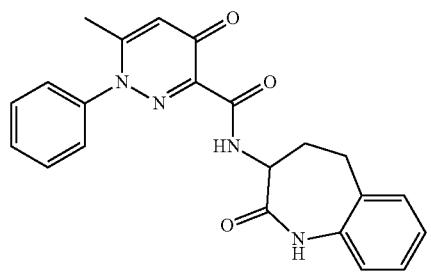 [SMILES: Cc1cc(=O)c(C(=O)NC2CCc3ccccc3NC2=O)nn1-c1ccccc1] | N-(3-chloro-2-fluorophenyl)-6-methyl-4-oxo-1-(p-tolyl)-1,4-dihydropyridazine-3-carboxamide | 371/372 |

Example 38

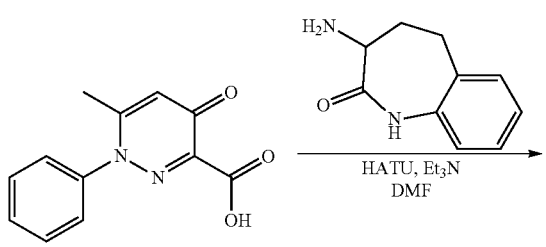

6-Methyl-4-oxo-N-(2-oxo-2,3,4,5-tetrahydro-1H-benzo[b]azepin-3-yl)-1-phenyl-1,4-dihydro-pyridazine-3-carboxamide To a solution of Intermediate I (72 mg, 0.31 mmol) in DMF (1.5 ml) were added HATU (120 mg, 0.31 mmol), 3-amino-1,3,4,5-tetrahydro-2H-benzo[b]azepin-2-one (50 mg, 0.28 mmol), and TEA (0.100 ml, 0.71 mmol) and the resulting mixture was stirred at room temperature for 2 hr. Sat NaHCO₃ was added, and the aqueous phase was extracted with EtOAc (3×), the combined organic layers were washed with sat NaCl, dried over Na₂SO₄, filtered and concentrated under reduced pressure. The residue was purified by mass-triggered preparative HPLC (Mobile phase: A=0.1% TFA/H₂O, B=0.1% TFA/MeCN; Gradient: B=10-50%; 12 min; Column: C18) to give the title compound (4.1 mg, 10 mol, 4% yield) as an off-white solid.

MS (ES+) $C_{22}H_{20}N_4O_3$ requires: 388, found: 389 [M+H]+.

¹H NMR (600 MHz, DMSO-d6) δ 10.66 (d, J=7.5 Hz, 1H), 10.00 (s, 1H), 7.62-7.53 (m, 5H), 7.33 (d, J=7.5 Hz, 1H), 7.30-7.25 (m, 1H), 7.17-7.12 (m, 1H), 7.03 (d, J=7.5 Hz, 1H), 6.85 (s, 1H), 4.44-4.37 (m, 1H), 2.85-2.77 (m, 1H), 2.74-2.67 (m, 1H), 2.62-2.53 (m, 1H), 2.15 (s, 3H), 2.04-1.95 (m, 1H).

Example 39

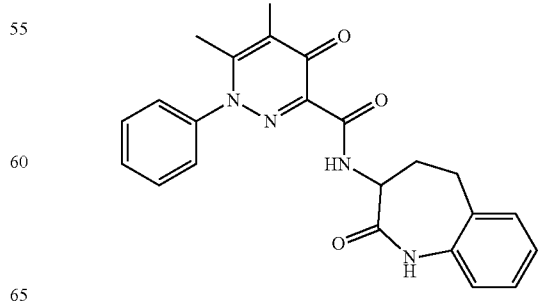

5-Chloro-6-methyl-4-oxo-N-(2-oxo-2,3,4,5-tetra-hydro-1H-benzo[b]azepin-3-yl)-1-phenyl-1,4-dihydropyridazine-3-carboxamide and Example 40

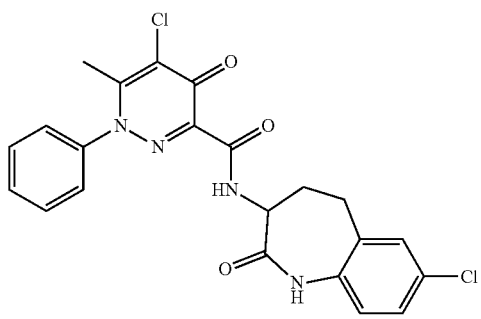 [SMILES: Cc1c(Cl)c(=O)c(C(=O)NC2CCc3cc(Cl)ccc3NC2=O)nn1-c1ccccc1]

5-Chloro-N-(7-chloro-2-oxo-2,3,4,5-tetrahydro-1H-benzo[b]azepin-3-yl)-6-methyl-4-oxo-1-phenyl-1,4-dihydropyridazine-3-carboxamide

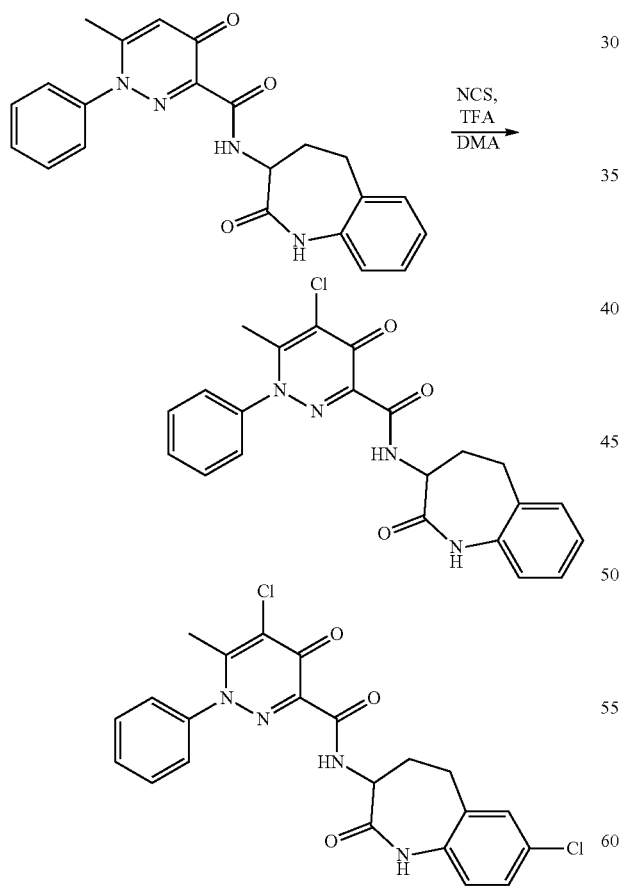

5-Chloro-6-methyl-4-oxo-N-(2-oxo-2,3,4,5-tetrahydro-1H-benzo[b]azepin-3-yl)-1-phenyl-1,4-dihydropyridazine-3-carboxamide (Example 39) and 5-chloro-N-(7-chloro-2-oxo-2,3,4,5-tetrahydro-1H-benzo[b]azepin-3-yl)-6-methyl-4-oxo-1-phenyl-1,4-dihydropyridazine-3-carboxamide (Example 40) To a solution of the Example 38 compound (20 mg, 0.051 mmol) in DMA (0.3 ml) at 0° C. were added NCS (8.3 mg, 0.062 mmol) and a drop of TFA and the resulting mixture was stirred at 0° C. for 30 mins. Water was added, and the aqueous phase was extracted with EtOAc (3×), the combined organic layers were washed with sat NaCl, dried over $Na_2SO_4$, filtered and concentrated under reduced pressure. The residue was purified by mass-triggered preparative HPLC (Mobile phase: A=0.1% TFA/$H_2O$, B=0.1% TFA/MeCN; Gradient: B=30-70%; 20 min; Column: C18) to afford two compounds.

Example 39: white solid (1.3 mg, 3.1 mol, 6% yield).

MS (ES$^+$) $C_{22}H_{19}ClN_4O_3$ requires: 422, found: 423 [M+H]$^+$.

$^1$H NMR (600 MHz, DMSO) δ 10.40 (d, J=7.2 Hz, 1H), 10.04 (s, 1H), 7.65-7.57 (m, 5H), 7.33 (d, J=7.5 Hz, 1H), 7.28 (t, J=7.6 Hz, 1H), 7.15 (t, J=7.5 Hz, 1H), 7.03 (d, J=7.8 Hz, 1H), 4.43-4.36 (m, 1H), 2.86-2.77 (m, 1H), 2.74-2.68 (m, 1H), 2.64-2.54 (m, 1H), 2.32 (s, 3H), 2.05-1.96 (m, 1H).

Example 40: white solid (1.2 mg, 2.6 mol, 5% yield).

MS (ES$^+$) $C_{22}H_{18}Cl_2N_4O_3$ requires: 457, found: 458 [M+H]$^+$.

$^1$H NMR (600 MHz, DMSO-d6) δ 10.39 (d, J=7.1 Hz, 1H), 10.10 (s, 1H), 7.69-7.55 (m, 5H), 7.45 (d, J=2.6 Hz, 1H), 7.33 (dd, J=8.4, 2.5 Hz, 1H), 7.04 (d, J=8.5 Hz, 1H), 4.42-4.36 (m, 1H), 2.85-2.72 (m, 2H), 2.64-2.57 (m, 1H), 2.32 (s, 3H), 2.06-1.97 (m, 1H).

Example 41

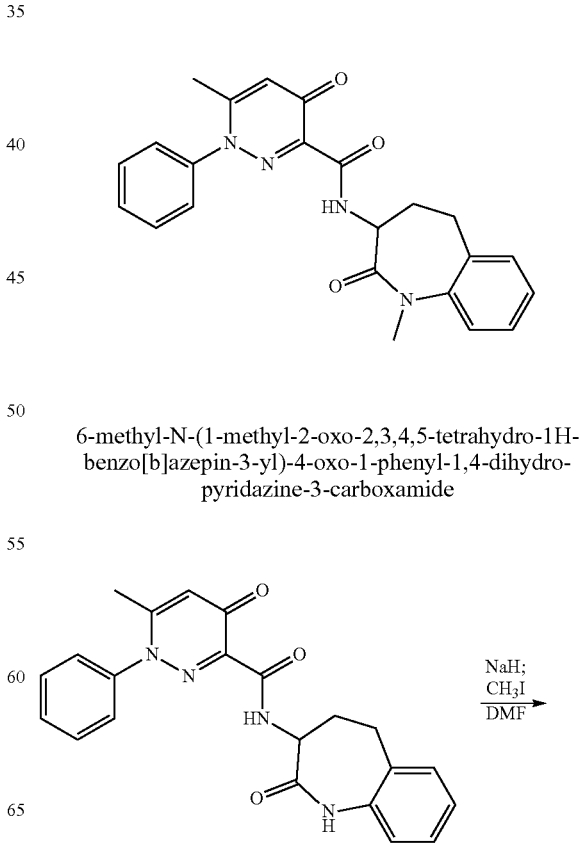

6-methyl-N-(1-methyl-2-oxo-2,3,4,5-tetrahydro-1H-benzo[b]azepin-3-yl)-4-oxo-1-phenyl-1,4-dihydropyridazine-3-carboxamide -continued

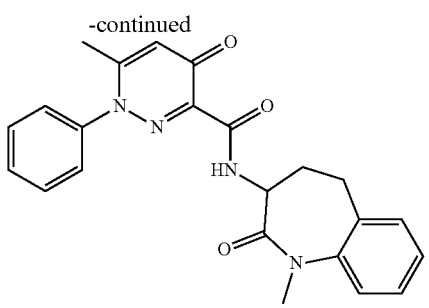

To a solution of the Example 38 compound (50 mg, 0.13 mmol) in DMF (0.5 ml) at 0° C. was added NaH (10 mg of a 60% dispersion in mineral oil, 0.26 mmol) and MeI (8.0 µl, 0.13 mmol) and the resulting mixture was stirred at 0° C. for 1 hr. At 0° C. the reaction mixture was quenched with 1M HCl added dropwise, and the mixture was purified by mass-triggered preparative HPLC (Mobile phase: A=0.1% TFA/H$_2$O, B=0.1% TFA/MeCN; Gradient: B=20-60%; 12 min; Column: C18) to give the title compound (3.8 mg, 9.4 mol, 7% yield) as an off-white solid.

MS (ES$^+$) C$_{23}$H$_{22}$N$_4$O$_3$ requires: 402, found: 403 [M+H]$^+$.

$^1$H NMR (600 MHz, DMSO-d6) δ 10.66 (d, J=7.2 Hz, 1H), 7.62-7.53 (m, 5H), 7.41-7.32 (m, 3H), 7.27-7.22 (m, 1H), 6.85 (s, 1H), 4.44-4.37 (m, 1H), 3.32 (s, 3H), 2.82-2.74 (m, 1H), 2.71-2.65 (m, 1H), 2.49-2.44 (m, 1H), 2.15 (s, 3H), 2.00-1.91 (m, 1H).

Example 42

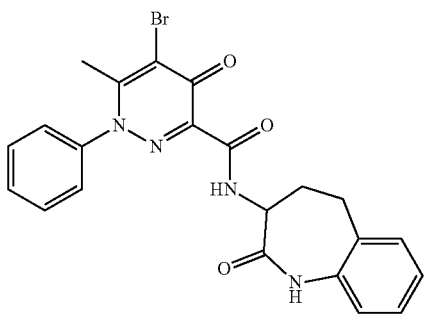 [SMILES: Cc1c(Br)c(=O)c(C(=O)NC2CCc3ccccc3NC2=O)nn1-c1ccccc1]

5-Bromo-6-methyl-4-oxo-N-(2-oxo-2,3,4,5-tetra-hydro-1H-benzo[b]azepin-3-yl)-1-phenyl-1,4-dihydropyridazine-3-carboxamide and Example 43

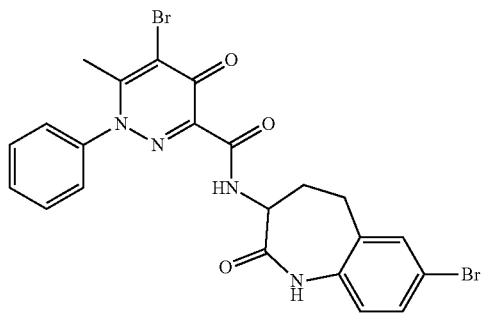 [SMILES: Cc1c(Br)c(=O)c(C(=O)NC2CCc3cc(Br)ccc3NC2=O)nn1-c1ccccc1]

5-Bromo-N-(7-bromo-2-oxo-2,3,4,5-tetrahydro-1H-benzo[b]azepin-3-yl)-6-methyl-4-oxo-1-phenyl-1,4-dihydropyridazine-3-carboxamide

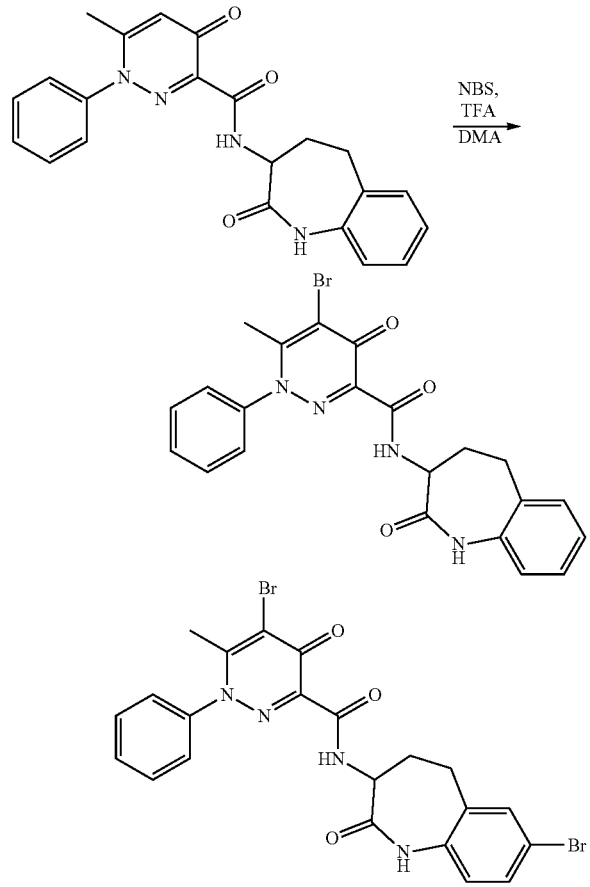

5-Bromo-6-methyl-4-oxo-N-(2-oxo-2,3,4,5-tetrahydro-1H-benzo[b]azepin-3-yl)-1-phenyl-1,4-dihydropyridazine-3-carboxamide (Example 42) and 5-Bromo-N-(7-bromo-2-oxo-2,3,4,5-tetrahydro-1H-benzo[b]azepin-3-yl)-6-methyl-4-oxo-1-phenyl-1,4-dihydropyridazine-3-carboxamide (Example 43) To a solution of the Example 38 compound (20 mg, 0.051 mmol) in DMA (0.3 ml) at 0° C. was added NBS (11.0 mg, 0.062 mmol) and a drop of TFA and the resulting mixture was stirred at 0° C. for 30 mins then allowed to reach room temperature and stirred for 1 hr. Water was added, and the aqueous phase was extracted with EtOAc (3×), the combined organic layers were washed with sat NaCl, dried over Na$_2$SO$_4$, filtered and concentrated under reduced pressure. The residue was purified by mass-triggered preparative HPLC (Mobile phase: A=0.1% TFA/H$_2$O, B=0.1% TFA/MeCN; Gradient: B=30-70%; 20 min; Column: C18) to afford two compounds.

Example 42: off-white solid (5.0 mg, 10.7 mol, 21% yield).

MS (ES$^+$) C$_{22}$H$_{19}$BrN$_4$O$_3$ requires: 467, found: 468 [M+H]$^+$.

$^1$H NMR (600 MHz, DMSO-d6) δ 10.41 (d, J=7.2 Hz, 1H), 10.03 (s, 1H), 7.64-7.55 (m, 5H), 7.33 (d, J=7.5 Hz, 1H), 7.28 (t, J=7.6 Hz, 1H), 7.15 (t, J=7.4 Hz, 1H), 7.03 (d, J=7.8 Hz, 1H), 4.43-4.36 (m, 1H), 2.86-2.77 (m, 1H), 2.74-2.67 (m, 1H), 2.64-2.54 (m, 1H), 2.37 (s, 3H), 2.04-1.96 (m, 1H).

Example 43: off-white solid (5.7 mg, 10.4 mol, 20% yield).

MS (ES⁺) $C_{22}H_{18}Br_2N_4O_3$ requires: 546, found: 547[M+H]⁺.

¹H NMR (600 MHz, DMSO-d6) δ 10.41 (d, J=7.2 Hz, 1H), 10.09 (s, 1H), 7.65-7.54 (m, 6H), 7.46 (d, J=8.4 Hz, 1H), 6.98 (d, J=8.4 Hz, 1H), 4.42-4.35 (m, 1H), 2.82-2.71 (m, 2H), 2.63-2.55 (m, 1H), 2.37 (s, 3H), 2.05-1.97 (m, 1H).

Example 44

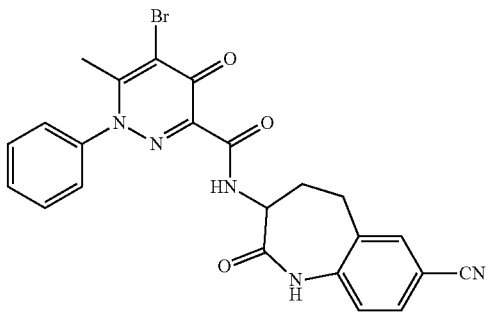 [SMILES: Cc1c(Br)c(=O)c(C(=O)NC2CCc3cc(C#N)ccc3NC2=O)nn1-c1ccccc1]

5-Bromo-N-(7-cyano-2-oxo-2,3,4,5-tetrahydro-1H-benzo[b]azepin-3-yl)-6-methyl-4-oxo-1-phenyl-1,4-dihydropyridazine-3-carboxamide

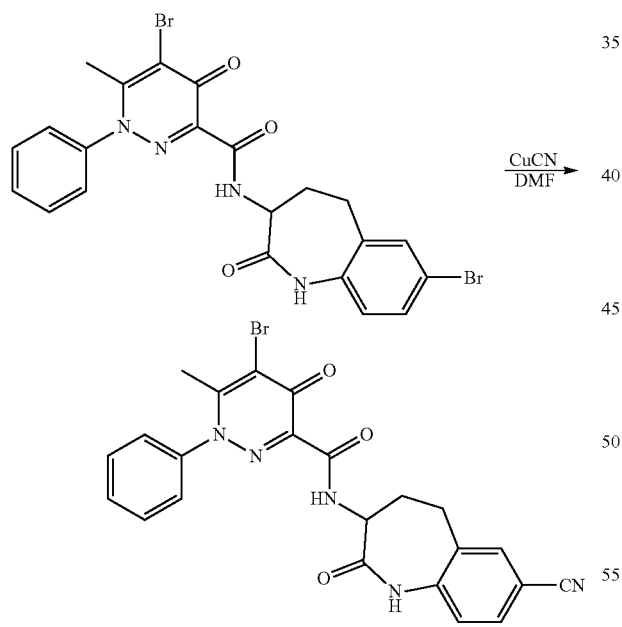

To a solution of the Example 43 compound (20 mg, 0.037 mmol) in DMF (0.2 ml) was added copper(I) cyanide (6.6 mg, 0.073 mmol) The mixture was degassed for 15 min then the resulting mixture was stirred at 120° C. for 18 hrs. The reaction mixture was diluted with methanol, filtered through celite. The filter cake was washed with methanol and the combined filtrates were concentrated under reduced pressure. The residue was purified by mass-triggered preparative HPLC (Mobile phase: A=0.1% TFA/H₂O, B=0.1% TFA/MeCN; Gradient: B=30-70%; 20 min; Column: C18) to give the title compound (1.2 mg, 2.4 mol, 7% yield) as an off-white solid.

MS (ES⁺) $C_{23}H_{18}BrN_5O_3$ requires: 492, found: 493 [M+H]⁺.

¹H NMR (600 MHz, DMSO-d6) δ 10.11 (s, 1H), 9.90 (d, J=7.3 Hz, 1H), 7.65-7.56 (m, 5H), 7.46 (dd, J=8.4, 2.3 Hz, 1H), 6.98 (d, J=8.4 Hz, 1H), 4.40-4.32 (m, 1H), 2.80-2.72 (m, 2H), 2.6-2.54 (m, 2H), 2.36 (s, 3H), 2.06-1.97 (m, 1H).

Example 45

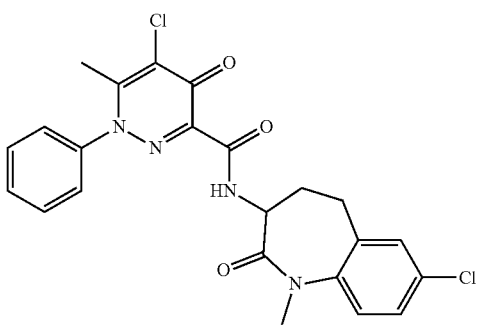 [SMILES: Cc1c(Cl)c(=O)c(C(=O)NC2CCc3cc(Cl)ccc3N(C)C2=O)nn1-c1ccccc1]

5-Chloro-N-(7-chloro-1-methyl-2-oxo-2,3,4,5-tetrahydro-1H-benzo[b]azepin-3-yl)-6-methyl-4-oxo-1-phenyl-1,4-dihydropyridazine-3-carboxamide and

Example 46

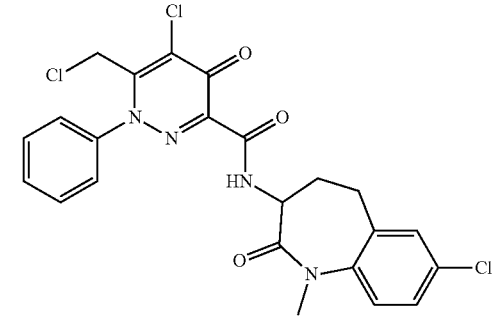 [SMILES: CN1C(=O)C(NC(=O)c2nn(-c3ccccc3)c(CCl)c(Cl)c2=O)CCc2cc(Cl)ccc21]

5-chloro-N-(7-chloro-1-methyl-2-oxo-2,3,4,5-tetrahydro-1H-benzo[b]azepin-3-yl)-6-(chloromethyl)-4-oxo-1-phenyl-1,4-dihydropyridazine-3-carboxamide

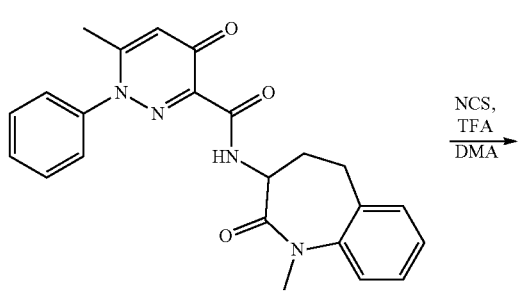

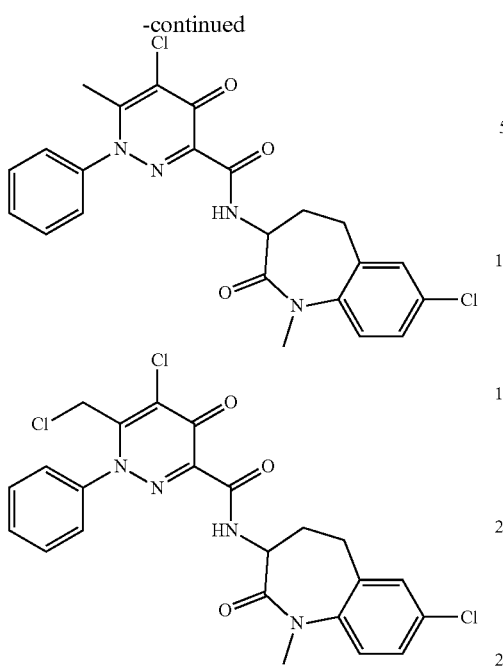

The title compounds were prepared from Example 41 using the method of Example 39/40 to afford two compounds.

Example 45: white solid (2.4 mg, 5.1 mol, 10% yield).

MS (ES+) $C_{23}H_{20}Cl_2N_4O_3$ requires: 471, found: 472 [M+H]+.

$^1$H NMR (600 MHz, DMSO-d6) δ 10.37 (d, J=7.3 Hz, 1H), 7.66-7.56 (m, 5H), 7.51-7.39 (m, 3H), 4.42-4.35 (m, 1H), 3.30 (s, 3H), 2.78-2.69 (m, 2H), 2.53-2.48 (m, 1H), 1.31 (s, 3H), 2.02-1.94 (m, 1H).

Example 46: Obtained as a byproduct from the example 45 synthesis.

MS (ES+) $C_{23}H_{19}Cl_3N_4O_3$ requires: 505, found: 506 [M+H]+.

$^1$H NMR (600 MHz, CDCl3) δ 10.67 (d, J=7.0 Hz, 1H), 7.62-7.53 (m, 3H), 7.50-7.45 (m, 2H), 7.32-7.27 (m, 1H), 7.26-7.23 (m, 1H), 7.15-7.11 (m, 1H), 4.69-4.62 (m, 1H), 4.51-4.41 (m, 2H), 3.41 (s, 3H), 2.93-2.84 (m, 1H), 2.79-2.69 (m, 1H), 2.65-2.59 (m, 1H), 2.16-2.05 (m, 1H).

Example 47

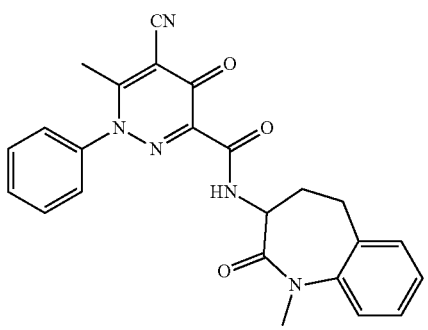 [SMILES: Cc1c(C#N)c(=O)c(C(=O)NC2CCc3ccccc3N(C)C2=O)nn1-c1ccccc1]

5-Cyano-6-methyl-N-(1-methyl-2-oxo-2,3,4,5-tetrahydro-1H-benzo[b]azepin-3-yl)-4-oxo-1-phenyl-1,4-dihydropyridazine-3-carboxamide

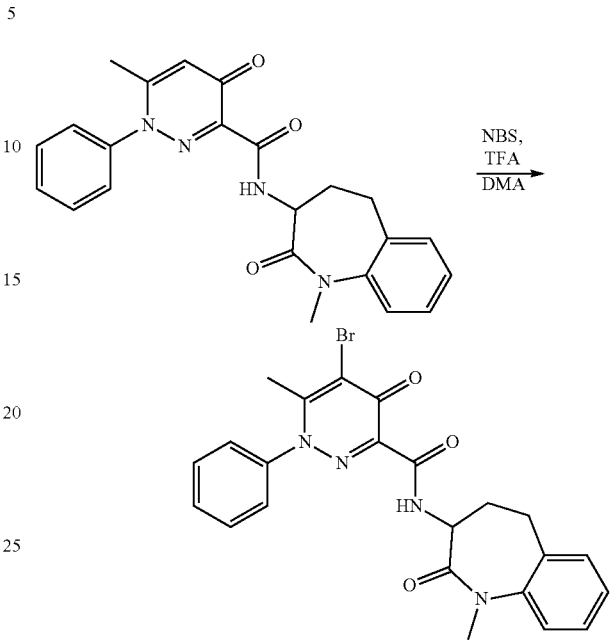

5-Bromo-6-methyl-N-(1-methyl-2-oxo-2,3,4,5-tetrahydro-1H-benzo[b]azepin-3-yl)-4-oxo-1-phenyl-1,4-dihydropyridazine-3-carboxamide The method to obtain 42 was applied to the Example 41 compound to obtain the title compound MS (ES+) $C_{23}H_{21}BrN_4O_3$ requires: 481, found: 482 [M+H]+.

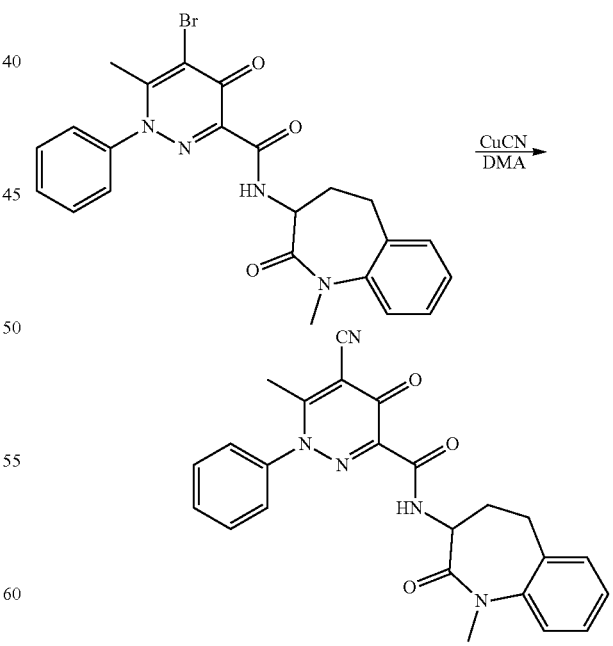

5-Cyano-6-methyl-N-(1-methyl-2-oxo-2,3,4,5-tetrahydro-1H-benzo[b]azepin-3-yl)-4-oxo-1-phenyl-1,4-dihydropyridazine-3-carboxamide To a solution of the product from the previous step (50 mg, 0.10 mmol) in DMA (1 ml)

under nitrogen, were added copper(I) cyanide (12 mg, 0.14 mmol) and sodium iodide (20 mg, 0.14 mmol) and the resulting mixture was stirred at 150° C. overnight. The reaction mixture was diluted with methanol, filtered through celite, the filter cake was washed with methanol, and the combined filtrates were concentrated under reduced pressure. The residue was purified by mass-triggered preparative HPLC (Mobile phase: A=0.1% TFA/H$_2$O, B=0.1% TFA/MeCN; Gradient: B=30-70%; 12 min; Column: C18) to give the title compound (4.5 mg, 10 mol, 10% yield) as an off-white solid. MS (ES$^+$) C$_{24}$H$_{21}$N$_5$O$_3$ requires: 427, found: 428 [M+H]$^+$. $^1$H NMR (600 MHz, DMSO-d6) δ 9.87 (d, J=7.2 Hz, 1H), 7.67-7.54 (m, 5H), 7.44-7.29 (m, 3H), 7.28-7.20 (m, 1H), 4.40-4.33 (m, 1H), 3.4 (s, 3H), 2.82-2.73 (m, 1H), 2.72-2.65 (m, 1H), 2.49-2.42 (m, 1H), 2.35 (s, 3H), 2.02-1.94 (m, 1H).

Example 48

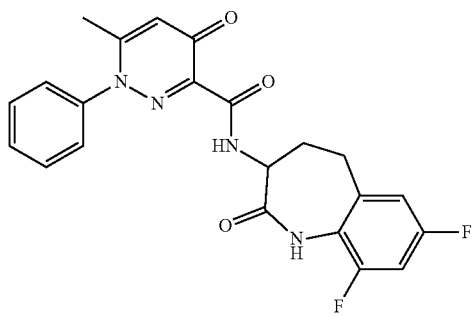 [SMILES: Cc1cc(=O)c(C(=O)NC2CCc3cc(F)cc(F)c3NC2=O)nn1-c1ccccc1]

N-(7,9-difluoro-2-oxo-2,3,4,5-tetrahydro-1H-benzo[b]azepin-3-yl)-6-methyl-4-oxo-1-phenyl-1,4-dihydropyridazine-3-carboxamide

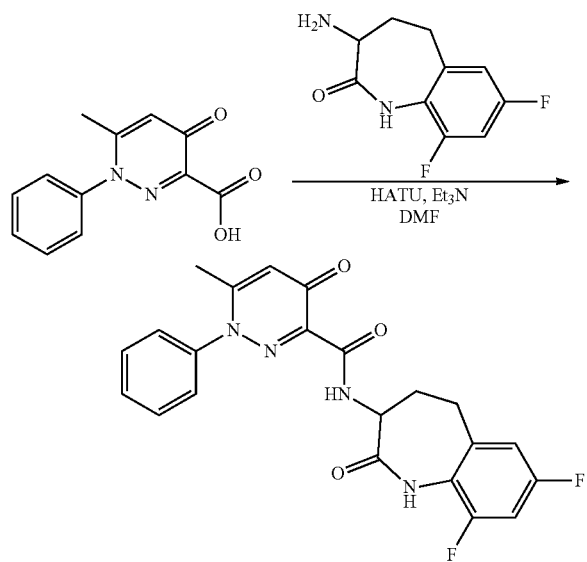

Reaction of Intermediate I with 3-amino-7,9-difluoro-1,3,4,5-tetrahydro-2H-benzo[b]azepin-2-one, according to the method used to obtain the Example 38 compound, afforded the title compound as a white solid.

MS (ES$^+$) C$_{22}$H$_{18}$F$_2$N$_4$O$_3$ requires: 424, found: 425 [M+H]$^+$.
$^1$H NMR (600 MHz, DMSO-d6) δ 10.67 (d, J=7.1 Hz, 1H), 9.97 (s, 1H), 7.66-7.52 (m, 5H), 7.32-23 (m, 1H), 7.21-7.11 (m, 1H), 6.86 (s, 1H), 4.50-4.36 (m, 1H), 2.89-2.75 (m, 2H), 2.66-2.54 (m, 1H), 2.16 (s, 3H), 2.07-1.95 (m, 1H).

Example 49

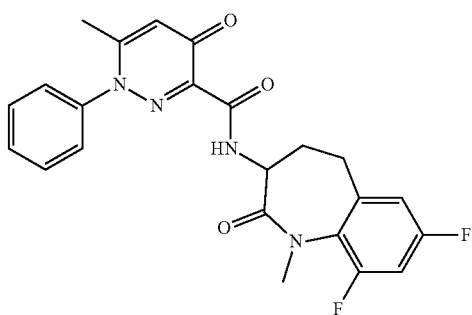 [SMILES: Cc1cc(=O)c(C(=O)NC2CCc3cc(F)cc(F)c3N(C)C2=O)nn1-c1ccccc1]

N-(7,9-difluoro-1-methyl-2-oxo-2,3,4,5-tetrahydro-1H-benzo[b]azepin-3-yl)-6-methyl-4-oxo-1-phenyl-1,4-dihydropyridazine-3-carboxamide

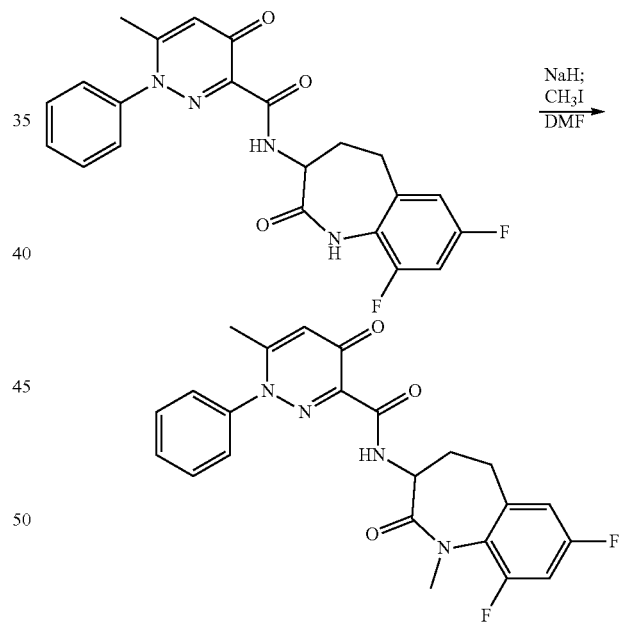

Reaction of the Example 48 compound, under the conditions used to afford the Example 41 compound, provided the title compound (10 mg, 0.023 mmol, 50% yield) as a white solid.

MS (ES$^+$) C$_{23}$H$_{20}$F$_2$N$_4$O$_3$ requires: 438, found: 439 [M+H]$^+$.
$^1$H NMR (600 MHz, DMSO) δ 10.67 (d, J=7.2 Hz, 1H), 7.64-7.52 (m, 5H), 7.40-7.33 (m, 1H), 7.22-7.17 (m, 1H), 6.85 (s, 1H), 4.47-4.38 (m, 1H), 3.21 (s, 3H), 2.85-2.76 (m, 2H), 2.48-2.42 (m, 1H), 2.15 (s, 3H), 2.02-1.93 (m, 1H).

Unless otherwise noted, the compounds listed in Table 2 were prepared using the method of Example 38.

TABLE 2

Examples 50-83

| Ex | Structure | Spectral Data |
|---|---|---|
| 50 | (S)-6-methyl-N-(5-methyl-4-oxo-2,3,4,5-tetrahydropyrido[3,2-b][1,4]oxazepin-3-yl)-4-oxo-1-phenyl-1,4-dihydropyridazine-3-carboxamide | $C_{21}H_{19}N_5O_4$ requires: 405, found: 406 [M + H]$^+$. $^1$H NMR (600 MHz, DMSO) δ 10.80 (d, J = 6.9 Hz, 1H), 8.37-8.33 (m, 1H), 7.75-7.70 (m, 1H), 7.62-7.54 (m, 5H), 7.36-7.30 (m, 1H), 6.89 (s, 1H), 4.97-4.90 (m, 1H), 4.69-4.63 (m, 1H), 4.43-4.36 (m, 1H), 3.38 (s, 3H), 2.16 (s, 3H). |
| 51 | 6-methyl-1-(6-methylpyridin-3-yl)-4-oxo-N-(2-oxo-2,3,4,5-tetrahydro-1H-benzo[b]azepin-3-yl)-1,4-dihydropyridazine-3-carboxamide | $C_{22}H_{21}N_5O_3$ requires: 403, found: 404 [M + H]$^+$. $^1$H NMR (600 MHz, DMSO) δ 10.59 (d, J = 7.3 Hz, 1H), 10.00 (s, 1H), 8.66 (d, J = 2.7 Hz, 1H), 7.97 (dd, J = 8.3, 2.6 Hz, 1H), 7.51 (d, J = 8.4 Hz, 1H), 7.33 (d, J = 7.5 Hz, 1H), 7.30-7.25 (m, 1H), 7.18-7.12 (m, 1H), 7.02 (d, J = 7.8 Hz, 1H), 6.86 (s, 1H), 4.44-4.36 (m, 1H), 2.85-2.70 (m, 1H), 2.73-2.67 (m, 1H), 2.61-2.54 (m, 4H), 2.17 (s, 3H), 2.03-1.95 (m, 1H). |
| 52 | 1-(3-fluoro-4-methylphenyl)-6-methyl-4-oxo-N-(2-oxo-2,3,4,5-tetrahydro-1H-benzo[b]azepin-3-yl)-1,4-dihydropyridazine-3-carboxamide | $C_{23}H_{21}FN_4O_3$ requires: 420, found: 421 [M + H]$^+$. $^1$H NMR (500 MHz, DMSO) δ 10.62 (d, J = 7.3 Hz, 1H), 10.01 (s, 1H), 7.55-7.47 (m, 2H), 7.36-7.30 (m, 2H), 7.30-7.24 (m, 1H), 7.20-7.11 (m, 1H), 7.05-7.00 (m, 1H), 6.84 (s, 1H), 4.44-4.35 (m, 1H), 2.86-2.75 (m, 1H), 2.74-2.67 (m, 1H), 2.63-2.55 (m, 1H), 2.31 (s, 3H), 2.16 (s, 3H), 2.04-1.94 (m, 1H). |
| 53 | 1-(3-cyanophenyl)-6-methyl-4-oxo-N-(2-oxo-2,3,4,5-tetrahydro-1H-benzo[b]azepin-3-yl)-1,4-dihydropyridazine-3-carboxamide | $C_{23}H_{19}N_5O_3$ requires: 413, found: 414 [M + H]$^+$. $^1$H NMR (600 MHz, DMSO) δ 10.58 (d, J = 7.2 Hz, 1H), 10.01 (s, 1H), 8.21-8.18 (m, 1H), 8.07 (d, J = 7.4 Hz, 1H), 7.99-7.94 (m, 1H), 7.84-7.78 (m, 1H), 7.33 (d, J = 7.4 Hz, 1H), 7.30-7.25 (m, 1H), 7.18-7.12 (m, 1H), 7.03 (d, J = 7.9 Hz, 1H), 6.86 (s, 1H), 4.44-4.36 (m, 1H), 2.85-2.76 (m, 1H), 2.74-2.67 (m, 1H), 2.62-2.53 (m, 1H), 2.17 (s, 3H), 2.04-1.95 (m, 1H). |

TABLE 2-continued

Examples 50-83

| Ex | Structure | Spectral Data |
|---|---|---|
| 54 | 1-(3-fluorophenyl)-6-methyl-4-oxo-N-(2-oxo-2,3,4,5-tetrahydro-1H-benzo[b]-azepin-3-yl)-1,4-dihydropyridazine-3-carboxamide | $C_{22}H_{19}FN_4O_3$ requires: 406, found: 407 $[M + H]^+$. $^1$H NMR (600 MHz, DMSO) δ 10.61 (d, J = 7.3 Hz, 1H), 10.01 (s, 1H), 7.68-7.62 (m, 1H), 7.62-7.57 (m, 1H), 7.49-7.43 (m, 2H), 7.33 (d, J = 7.4 Hz, 1H), 7.30-7.25 (m, 1H), 7.18-7.12 (m, 1H), 7.03 (d, J = 7.8 Hz, 1H), 6.85 (s, 1H), 4.44-4.37 (m, 1H), 2.85-2.76 (m, 1H), 2.74-2.67 (m, 1H), 2.63-2.53 (m, 1H), 2.17 (s, 3H), 2.03-1.95 (m, 1H). |
| 55 | (S)-N-(8-cyano-5-methyl-4-oxo-2,3,4,5-tetrahydrobenzo[b][1,4]oxazepin-3-yl)-6-methyl-4-oxo-1-phenyl-1,4-dihydropyridazine-3-carboxamide | $C_{23}H_{19}N_5O_4$ requires: 429, found: 430 $[M + H]^+$. $^1$H NMR (600 MHz, DMSO) δ 10.78 (d, J = 7.1 Hz, 1H), 7.82-7.77 (m, 2H), 7.69-7.65 (m, 1H), 7.62-7.52 (m, 5H), 6.88 (s, 1H), 4.96-4.89 (m, 1H), 4.65-4.59 (m, 1H), 4.41-4.34 (m, 1H), 3.36 (s, 3H), 2.16 (s, 3H). |
| 56 | 1-(4-cyanophenyl)-6-methyl-4-oxo-N-(2-oxo-2,3,4,5-tetrahydro-1H-benzo[b]-azepin-3-yl)-1,4-dihydropyridazine-3-carboxamide | $C_{23}H_{19}N_5O_3$ requires: 413, found: 414 $[M + H]^+$. $^1$H NMR (600 MHz, DMSO) δ 10.54 (d, J = 7.2 Hz, 1H), 9.98 (s, 1H), 8.10 (d, J = 8.4 Hz, 2H), 7.82 (d, J = 8.5 Hz, 2H), 7.32 (d, J = 7.4 Hz, 1H), 7.30-7.24 (m, 1H), 7.18-7.12 (m, 1H), 7.03 (d, J = 7.7 Hz, 1H), 6.85 (s, 1H), 4.44-4.37 (m, 1H), 2.85-2.76 (m, 1H), 2.74-2.67 (m, 1H), 2.61-2.52 (m, 1H), 2.18 (s, 3H), 2.03-1.95 (m, 1H). |
| 57 | 1-(4-fluorophenyl)-6-methyl-4-oxo-N-(2-oxo-2,3,4,5-tetrahydro-1H-benzo[b]-azepin-3-yl)-1,4-dihydropyridazine-3-carboxamide | $C_{22}H_{19}FN_4O_3$ requires: 406, found: 407 $[M + H]^+$. $^1$H NMR (600 MHz, DMSO) δ 10.65 (d, J = 7.4 Hz, 1H), 10.01 (s, 1H), 7.68-7.63 (m, 2H), 7.47-7.41 (m, 2H), 7.33 (d, J = 7.5 Hz, 1H), 7.30-7.25 (m, 1H), 7.18-7.12 (m, 1H), 7.03 (d, J = 7.8 Hz, 1H), 6.84 (s, 1H), 4.44-4.36 (m, 1H), 2.85-2.76 (m, 1H), 2.76-2.67 (m, 1H), 2.61-2.52 (m, 1H), 2.15 (s, 3H), 2.03-1.95 (m, 1H). |

TABLE 2-continued

Examples 50-83

| Ex | Structure | Spectral Data |
|---|---|---|
| 58 | 5-cyano-N-(8-cyano-2-oxo-2,3,4,5-tetrahydro-1H-benzo[b]azepin-3-yl)-6-methyl-4-oxo-1-phenyl-1,4-dihydro-pyridazine-3-carboxamide (a) | $C_{24}H_{18}N_6O_3$ requires: 438, found: 439 [M + H]$^+$. $^1$H NMR (600 MHz, DMSO) δ 10.44 (s, 1H), 9.90 (d, J = 7.2 Hz, 1H), 7.87-7.83 (m, 1H), 7.79-7.72 (m, 1H), 7.66-7.57 (m, 5H), 7.20-7.15 (m, 1H), 4.41-4.33 (m, 1H), 2.87-2.76 (m, 2H), 2.61-2.54 (m, 1H), 2.36 (s, 3H), 2.13-2.00 (m, 1H). |
| 59 | 1-(2-fluorophenyl)-6-methyl-4-oxo-N-(2-oxo-2,3,4,5-tetrahydro-1H-benzo[b]-azepin-3-yl)-1,4-dihydropyridazine-3-carboxamide | $C_{22}H_{19}FN_4O_3$ requires: 406, found: 407 [M + H]$^+$. $^1$H NMR (600 MHz, DMSO) δ 10.56-10.50 (m, 1H), 10.03-9.99 (m, 1H), 7.77-7.71 (m, 1H), 7.71-7.65 (m, 1H), 7.59-7.53 (m, 1H), 7.48-7.42 (m, 1H), 7.35-7.31 (m, 1H), 7.30-7.24 (m, 1H), 7.18-7.12 (m, 1H), 7.05-7.00 (m, 1H), 6.89 (s, 1H), 4.43-4.36 (m, 1H), 2.85-2.76 (m, 1H), 2.74-2.67 (m, 1H), 2.63-2.52 (m, 1H), 2.15 (s, 3H), 2.04-1.96 (m, 1H). |
| 60 | (S)-N-(8-cyano-5-methyl-4-oxo-2,3,4,5-tetrahydrobenzo[b][1,4]oxazepin-3-yl)-1-(4-cyanophenyl)-6-methyl-4-oxo-1,4-dihydropyridazine-3-carboxamide | $C_{24}H_{18}N_6O_4$ requires: 454, found: 455 [M + H]$^+$. $^1$H NMR (600 MHz, DMSO) δ 10.67 (d, J = 7.1 Hz, 1H), 8.13-8.09 (m, 2H), 7.85-7.77 (m, 4H), 7.69-7.64 (m, 1H) 6.89 (s, 1H) 4.96-4.88 (m, 1H), 4.62 (d, J = 7.5 Hz, 1H), 4.41-4.34 (m, 1H), 3.36 (s, 3H), 2.18 (s, 3H). |

TABLE 2-continued

Examples 50-83

| Ex | Structure | Spectral Data |
|---|---|---|
| 61 | (S)-N-(8-cyano-5-methyl-4-oxo-2,3,4,5-tetrahydrobenzo[b][1,4]oxazepin-3-yl)-1-(3-fluorophenyl)-6-methyl-4-oxo-1,4-dihydropyridazine-3-carboxamide | $C_{23}H_{18}FN_5O_4$ requires: 447, found: 448 $[M + H]^+$. $^1$H NMR (600 MHz, DMSO) δ 10.72 (d, J = 7.0 Hz, 1H), 7.82-7.77 (m, 2H), 7.69-7.63 (m, 2H), 7.62-7.57 (m, 1H), 7.50-7.43 (m, 2H), 6.88 (s, 1H), 4.96-4.89 (m, 1H), 4.65-4.59 (m, 1H), 4.41-4.34 (m, 1H), 3.36 (s, 3H), 2.18 (s, 3H). |
| 62 | (S)-N-(8-cyano-5-methyl-4-oxo-2,3,4,5-tetrahydrobenzo[b][1,4]oxazepin-3-yl)-1-(3-fluoro-4-methylphenyl)-6-methyl-4-oxo-1,4-dihydropyridazine-3-carboxamide | $C_{24}H_{20}FN_5O_4$ requires: 461, found: 462 $[M + H]^+$. $^1$H NMR (600 MHz, DMSO) δ 10.73 (d, J = 7.0 Hz, 1H), 7.82-7.77 (m, 2H), 7.67 (d, J = 9.0 Hz, 1H), 7.54-7.48 (m, 2H), 7.36-7.31 (m, 1H), 6.87 (s, 1H), 4.96-4.89 (m, 1H), 4.65-4.59 (m, 1H), 4.41-4.34 (m, 1H), 3.36 (s, 3H), 2.33-2.30 (m, 3H), 2.17 (s, 3H). |
| 63 | (S)-6-methyl-4-oxo-N-(4-oxo-2,3,4,5-tetrahydropyrido[3,2-b][1,4]oxazepin-3-yl)-1-phenyl-1,4-dihydropyridazine-3-carboxamide | $C_{20}H_{17}N_5O_4$ requires: 391, found: 392 $[M + H]^+$. $^1$H NMR (600 MHz, DMSO) δ 10.79 (d, J = 6.5 Hz, 1H), 10.60 (s, 1H), 8.15-8.11 (m, 1H), 7.64-7.54 (m, 6H), 7.20-7.14 (m, 1H), 6.88 (s, 1H), 4.93-4.86 (m, 1H), 4.57-4.52 (m, 1H), 4.38-4.32 (m, 1H), 2.17 (s, 3H). |
| 64 | 6-methyl-4-oxo-N-(2-oxo-2,3,4,5-tetrahydro-1H-benzo[b]azepin-3-yl)-1-(m-tolyl)-1,4-dihydropyridazine-3-carboxamide | $C_{23}H_{22}N_4O_3$ requires: 402, found: 403 $[M + H]^+$. $^1$H NMR (600 MHz, DMSO) δ 10.66 (d, J = 7.3 Hz, 1H), 10.00 (s, 1H), 7.49-7.44 (m, 1H), 7.41-7.31 (m, 4H), 7.30-7.25 (m, 1H), 7.18-7.12 (m, 1H), 7.03 (d, J = 7.9 Hz, 1H), 6.84 (s, 1H), 4.44-4.37 (m, 1H), 2.85-2.76 (m, 1H), 2.74-2.67 (m, 1H), 2.62-2.53 (m, 1H), 2.38 (s, 3H), 2.16 (s, 3H), 2.03-1.95 (m, 1H). |

TABLE 2-continued

Examples 50-83

| Ex | Structure | Spectral Data |
|---|---|---|
| 65 | 1-(4-methoxyphenyl)-6-methyl-4-oxo-N-(2-oxo-2,3,4,5-tetrahydro-1H-benzo[b]azepin-3-yl)-1,4-dihydropyridazine-3-carboxamide | $C_{23}H_{22}N_4O_4$ requires: 418, found: 419 [M + H]$^+$. $^1$H NMR (600 MHz, DMSO) δ 10.69-10.64 (m, 1H), 9.99 (s, 1H), 7.51-7.45 (m, 2H), 7.35-7.30 (m, 1H), 7.30-7.24 (m, 1H), 7.18-7.12 (m, 1H), 7.12-7.07 (m, 2H), 7.05-7.00 (m, 1H), 6.82 (s, 1H), 4.44-4.37 (m, 1H), 3.83 (s, 3H), 2.85-2.76 (m, 1H), 2.74-2.67 (m, 1H), 2.62-2.52 (m, 1H), 2.14 (s, 3H), 2.03-1.95 (m, 1H). |
| 66 | 1-(4-chlorophenyl)-6-methyl-4-oxo-N-(2-oxo-2,3,4,5-tetrahydro-1H-benzo[b]azepin-3-yl)-1,4-dihydro-pyridazine-3-carboxamide | $C_{22}H_{19}ClN_4O_3$ requires: 422, found: 423 [M + H]$^+$. $^1$H NMR (600 MHz, DMSO) δ 10.62 (d, J = 7.2 Hz, 1H), 10.00 (s, 1H), 7.69-7.59 (m, 4H), 7.35-7.32 (m, 1H), 7.30-7.24 (m, 1H), 7.18-7.12 (m, 1H), 7.05-7.00 (m, 1H), 6.84 (s, 1H), 4.44-4.36 (m, 1H), 2.85-2.76 (m, 1H), 2.73-2.67 (m, 1H), 2.61-2.52 (m, 1H), 2.16 (s, 3H), 2.03-1.95 (m, 1H). |
| 67 | 1-(3-methoxyphenyl)-6-methyl-4-oxo-N-(2-oxo-2,3,4,5-tetrahydro-1H-benzo[b]-azepin-3-yl)-1,4-dihydropyridazine-3-carboxamide | $C_{23}H_{22}N_4O_4$ requires: 418, found: 419 [M + H]$^+$. $^1$H NMR (600 MHz, DMSO) δ 10.66 (d, J = 7.3 Hz, 1H), 10.00 (s, 1H), 7.51-7.46 (m, 1H), 7.33 (d, J = 7.5 Hz, 1H), 7.30-7.24 (m, 1H), 7.20-7.17 (m, 1H), 7.16-7.09 (m, 3H), 7.02 (d, J = 7.7 Hz, 1H), 6.84 (s, 1H), 4.44-4.37 (m, 1H), 3.80 (s, 3H), 2.85-2.76 (m, 1H), 2.70 (dd, J = 13.6, 7.1 Hz, 1H), 2.61-2.54 (m, 1H), 2.17 (s, 3H), 2.03-1.95 (m, 1H). |
| 68 | 1-(3-chlorophenyl)-6-methyl-4-oxo-N-(2-oxo-2,3,4,5-tetrahydro-1H-benzo[b]-azepin-3-yl)-1,4-dihydropyridazine-3-carboxamide | $C_{22}H_{19}ClN_4O_3$ requires: 422, found: 423 [M + H]$^+$. $^1$H NMR (600 MHz, DMSO) δ 10.61 (d, J = 7.2 Hz, 1H), 10.00 (s, 1H), 7.81-7.77 (m, 1H), 7.70-7.65 (m, 1H), 7.65-7.57 (m, 2H), 7.33 (d, J = 7.4 Hz, 1H), 7.30-7.24 (m, 1H), 7.18-7.12 (m, 1H), 7.03 (d, J = 7.8 Hz, 1H), 6.84 (s, 1H), 4.44-4.36 (m, 1H), 2.85-2.76 (m, 1H), 2.74-2.67 (m, 1H), 2.61-2.53 (m, 1H), 2.17 (s, 3H), 2.03-1.95 (m, 1H). |

TABLE 2-continued

Examples 50-83

| Ex | Structure | Spectral Data |
|---|---|---|
| 69 | N-(7,9-difluoro-2,3,4,5-tetrahydro-1H-benzo[b]azepin-3-yl)-6-methyl-4-oxo-1-phenyl-1,4-dihydropyridazine-3-carboxamide | $C_{22}H_{20}F_2N_4O_2$ requires: 410, found: 411 [M + H]$^+$. $^1$H NMR (600 MHz, DMSO) δ 10.47 (d, J = 7.9 Hz, 1H), 7.68-7.52 (m, 5H), 7.04-6.97 (m, 1H), 6.89-6.84 (m, 1H), 6.82 (s, 1H), 5.12 (s, 1H), 4.17 (s, 1H), 3.12-3.06 (m, 1H), 3.05-2.99 (m, 1H), 2.87-2.80 (m, 1H), 2.72-2.65 (m, 1H), 2.16 (s, 3H), 1.84-1.71 (m, 2H). |
| 70 | 4-oxo-N-(2-oxo-2,3,4,5-tetrahydro-1H-benzo[b]azepin-3-yl)-1-phenyl-1,4-dihydrocinnoline-3-carboxamide | $C_{25}H_{20}N_4O_3$ requires: 424, found: 425 [M + H]$^+$. $^1$H NMR (600 MHz, DMSO) δ 10.30 (d, J = 7.2 Hz, 1H), 10.05 (s, 1H), 8.38 8.34 1H), 7.89-7.81 (m, 1H), 7.68-7.65 (m, 6H), 7.37-7.32 (m, 1H), 7.31-7.26 (m, 1H), 7.25-7.20 (m, 1H), 7.20-7.13 (m, 1H), 7.04 (d, J = 7.8 Hz, 1H), 4.50-4.42 (m, 1H), 2.88-2.79 (m, 1H), 2.76-2.70 (m, 1H), 2.69-2.61 (m, 1H), 2.08-1.99 (m, 1H). |
| 71 | 6-methyl-4-oxo-N-(2-oxo-2,3,4,5-tetrahydro-1H-benzo[b]azepin-3-yl)-1-(p-tolyl)-1,4-dihydropyridazine-3-carboxamide | $C_{23}H_{22}N_4O_3$ requires: 402, found: 403 [M + H]$^+$. $^1$H NMR (600 MHz, DMSO) δ 10.66 (d, J = 7.3 Hz, 1H), 9.99 (s, 1H), 7.43 (d, J = 8.2 Hz, 2H), 7.38 (d, J = 8.1 Hz, 2H), 7.33 (d, J = 7.5 Hz, 1H), 7.30-7.24 (m, 1H), 7.17-7.12 (m, 1H), 7.02 (d, J = 7.9 Hz, 1H), 6.83 (s, 1H), 4.44-4.36 (m, 1H), 2.85-2.76 (m, 1H), 2.73-2.67 (m, 1H), 2.62-2.52 (m, 1H), 2.39 (s, 3H), 2.14 (s, 3H), 2.03-1.95 (m, 1H). |

TABLE 2-continued

Examples 50-83

| Ex | Structure | Spectral Data |
|---|---|---|
| 72 | 6-methyl-N-(4-methyl-5-oxo-5,6,7,8-tetrahydro-4H-pyrazolo[1,5-a][1,3]diazepin-6-yl)-4-oxo-1-phenyl-1,4-dihydropyridazine-3-carboxamide | $C_{20}H_{20}N_6O_3$ requires: 392, found: 393 [M + H]$^+$. $^1$H NMR (600 MHz, DMSO) δ 10.72 (d, J = 7.2 Hz, 1H), 7.65-7.54 (m, 5H), 7.49 (d, J = 2.0 Hz, 1H), 6.87 (s, 1H), 6.33 (d, J = 2.1 Hz, 1H), 4.40-4.33 (m, 2H), 4.29-4.20 (m, 1H), 3.26 (s, 3H), 2.83-2.73 (m, 1H), 2.16 (s, 3H), 2.10-2.01 (m, 1H). |
| 73 | N-(5,6-dihydro-4H-benzo[f]imidazo[1,2-a]azepin-4-yl)-6-methyl-4-oxo-1-phenyl-1,4-dihydropyridazine-3-carboxamide | $C_{24}H_{21}N_5O_2$ requires: 411, found: 412 [M + H]$^+$. 1H NMR (600 MHz, DMSO) δ 10.88 (d, J = 6.4 Hz, 1H), 8.03 (s, 1H), 7.74 (s, 1H), 7.66-7.48 (m, 9H), 6.92 (s, 1H), 5.07-5.00 (m, 1H), 2.90-2.75 (m, 2H), 2.70-2.61 (m, 1H), 2.43-2.36 (m, 1H), 2.19 (s, 3H). |
| 74 | (S)-5-chloro-6-methyl-N-(5-methyl-4-oxo-2,3,4,5-tetrahydropyrido[3,2-b][1,4]oxazepin-3-yl)-4-oxo-1-phenyl-1,4-dihydropyridazine-3-carboxamide | $C_{21}H_{18}ClN_5O_4$ requires: 439, found: 440 [M + H]$^+$. $^1$H NMR (600 MHz, DMSO) δ 10.48 (d, J = 7.1 Hz, 1H), 8.38-8.34 (m, 1H), 7.75-7.71 (m, 1H), 7.65-7.57 (m, 5H), 7.36-7.31 (m, 1H), 4.97-4.90 (m, 1H), 4.69-4.63 (m, 1H), 4.45-4.38 (m, 1H), 3.39 (s, 3H), 2.32 (s, 3H). |

TABLE 2-continued

Examples 50-83

| Ex | Structure | Spectral Data |
|---|---|---|
| 75 | (S)-1-(3-fluoro-4-methylphenyl)-6-methyl-N-(5-methyl-4-oxo-2,3,4,5-tetrahydro-pyrido[3,2-b][1,4]oxazepin-3-yl)-4-oxo-1,4-dihydropyridazine-3-carboxamide | $C_{22}H_{20}FN_5O_4$ requires: 437, found: 438 $[M + H]^+$. $^1$H NMR (600 MHz, DMSO) δ 10.75 (d, J = 7.0 Hz, 1H), 8.37-8.33 (m, 1H), 7.75-7.70 (m, 1H), 7.55-7.46 (m, 2H), 7.36-7.28 (m, 2H), 6.87 (s, 1H), 4.97-4.90 (m, 1H), 4.68-4.62 (m, 1H), 4.43-4.36 (m, 1H), 3.38 (s, 3H), 2.32 (s, 3H), 2.17 (s, 3H). |
| 76 | (S)-N-(5-ethyl-4-oxo-2,3,4,5-tetrahydro-pyrido[3,2-b][1,4]oxazepin-3-yl)-6-methyl-4-oxo-1-phenyl-1,4-dihydro-pyridazine-3-carboxamide (b) | $C_{22}H_{21}N_5O_4$ requires: 419, found: 420 $[M + H]^+$. $^1$H NMR (600 MHz, DMSO) δ 10.79 (d, J = 7.1 Hz, 1H), 8.39-8.35 (m, 1H), 7.75-7.71 (m, 1H), 7.65-7.54 (m, 5H), 7.36-7.31 (m, 1H), 6.89 (s, 1H), 4.93-4.86 (m, 1H), 4.67-4.61 (m, 1H), 4.42-4.35 (m, 1H), 4.09-4.01 (m, 1H), 3.98-3.90 (m, 1H), 2.16 (s, 3H), 1.13 (t, J = 7.0 Hz, 3H). |
| 77 | (S)-6-methyl-N-(5-methyl-4-oxo-2,3,4,5-tetrahydropyrido[3,2-b][1,4]oxazepin-3-yl)-4-oxo-1-(p-tolyl)-1,4-dihydro-pyridazine-3-carboxamide | $C_{22}H_{21}N_5O_4$ requires: 419, found: 420 $[M + H]^+$. $^1$H NMR (600 MHz, DMSO) δ 10.80 (d, J = 6.9 Hz, 1H), 8.37-8.33 (m, 1H), 7.75-7.70 (m, 1H), 7.45-7.41 (m, 2H), 7.40-7.37 (m, 2H), 7.36-7.30 (m, 1H), 6.87 (s, 1H), 4.97-4.90 (m, 1H), 4.68-4.62 (m, 1H), 4.46-4.34 (m, 1H), 3.38 (s, 3H), 2.39 (s, 3H), 2.15 (s, 3H). |

TABLE 2-continued

Examples 50-83

| Ex | Structure | Spectral Data |
|---|---|---|
| 78 | N-((2R,3S)-2,5-dimethyl-4-oxo-2,3,4,5-tetrahydropyrido[3,2-b]-[1,4]oxazepin-3-yl)-6-methyl-4-oxo-1-phenyl-1,4-dihydropyridazine-3-carboxamide | $C_{22}H_{21}N_5O_4$ requires: 419, found: 420 [M + H]$^+$. $^1$H NMR (600 MHz, DMSO) δ 10.98 (d, J = 7.2 Hz, 1H), 8.37-8.32 (m, 1H), 7.75-7.71 (m, 1H), 7.63-7.54 (m, 5H), 7.36-7.30 (m, 1H), 6.90 (s, 1H), 5.00 (t, J = 6.8 Hz, 1H), 4.96-4.89 (m, 1H), 3.38 (s, 3H), 2.16 (s, 3H), 1.36 (d, J = 6.3 Hz, 3H) |
| 79 | 1-(5-fluoropyridin-3-yl)-6-methyl-4-oxo-N-(2-oxo-2,3,4,5-tetrahydro-1H-benzo[b]azepin-3-yl)-1,4-dihydropyridazine-3-carboxamide | $C_{21}H_{18}FN_5O_3$ requires: 407, found: 408 [M + H]$^+$. $^1$H NMR (600 MHz, DMSO) δ 10.52 (d, J = 7.4 Hz, 1H), 10.01 (s, 1H), 8.86-8.83 (m, 1H), 8.77-8.73 (m, 1H), 8.26-8.21 (m, 1H), 7.33 (d, J = 7.4 Hz, 1H), 7.30-7.25 (m, 1H), 7.15 (t, J = 7.4 Hz, 1H), 7.03 (d, J = 7.7 Hz, 1H), 6.87 (s, 1H), 4.44-4.36 (m, 1H), 2.85-2.76 (m, 1H), 2.74-2.67 (m, 1H), 2.61-2.53 (m, 1H), 2.21 (s, 3H), 2.04-1.95 (m, 1H). |
| 80 | 6-methyl-N-((2R,3S)-2-methyl-4-oxo-2,3,4,5-tetrahydropyrido[3,2-b]-[1,4]oxazepin-3-yl)-4-oxo-1-phenyl-1,4-dihydropyridazine-3-carboxamide | $C_{21}H_{19}N_5O_4$ requires: 405, found: 406 [M + H]$^+$. $^1$H NMR (600 MHz, DMSO) δ 10.93 (d, J = 7.2 Hz, 1H), 10.72 (s, 1H), 8.20-8.16 (m, 1H), 7.66-7.54 (m, 6H), 7.24-7.19 (m, 1H), 6.89 (s, 1H), 4.99-4.95 (m, 1H), 4.95-4.88 (m, 1H), 2.17 (s, 3H), 1.34 (d, J = 6.3 Hz, 3H). |
| 81 | N-(7-methoxy-1-methyl-2-oxo-2,3,4,5-tetrahydro-1H-pyrido[3,4-b]azepin-3-yl)-6-methyl-4-oxo-1-phenyl-1,4-dihydropyridazine-3-carboxamide | $C_{23}H_{23}N_5O_4$ requires: 433, found: 434 [M + H]$^+$. $^1$H NMR (600 MHz, DMSO-d$_6$) δ 10.72-10.68 (m, 1H), 7.79-7.76 (m, 1H), 7.62-7.55 (m, 5H), 6.87-6.82 (m, 2H), 4.49-4.42 (m, 1H), 3.89 (s, 3H), 3.27 (s, 3H), 3.05-2.96 (m, 1H), 2.70-2.57 (m, 2H), 2.16 (s, 3H), 2.07-1.98 (m, 1H). |

TABLE 2-continued

Examples 50-83

| Ex | Structure | Spectral Data |
|---|---|---|
| 82 | (S)-5-chloro-1-(3-fluoro-4-methyl-phenyl)-6-methyl-N-(5-methyl-4-oxo-2,3,4,5-tetrahydropyrido[3,2-b]-[1,4]oxazepin-3-yl)-4-oxo-1,4-dihydropyridazine-3-carboxamide (c) | $C_{22}H_{19}ClFN_5O_4$ requires: 471, found: 472 [M + H]$^+$. $^1$H NMR (600 MHz, DMSO-d$_6$) δ 10.43 (d, J = 7.0 Hz, 1H), 8.38-8.34 (m, 1H), 7.75-7.71 (m, 1H), 7.56-7.51 (m, 2H), 7.40-7.36 (m, 1H), 7.36-7.31 (m, 1H), 4.97-4.90 (m, 1H), 4.68-4.63 (m, 1H), 4.45-4.38 (m, 1H), 3.39 (s, 3H), 2.33 (d, J = 6.0 Hz, 6H) |
| 83 | (S)-6-methyl-4-oxo-N-(2-oxo-2,3,4,5-tetrahydro-1H-benzo[b]azepin-3-yl)-1-(2,2,2-trifluoroethyl)-1,4-dihydro-pyridazine-3-carboxamide | $C_{18}H_{17}F_3N_4O_3$ requires: 394, found: 395 [M + H]$^+$. $^1$H NMR (600 MHz, DMSO) δ 10.44 (d, J = 7.4 Hz, 1H), 10.00 (s, 1H), 7.33 (d, J = 7.4 Hz, 1H), 7.31-7.25 (m, 1H), 7.19-7.13 (m, 1H), 7.03 (d, J = 7.8 Hz, 1H), 6.75 (s, 1H), 5.29-5.21 (m, 2H), 4.44-4.37 (m, 1H), 2.85-2.76 (m, 1H), 2.74-2.67 (m, 1H), 2.60-2.54 (m, 1H), 2.46 (s, 3H), 2.03-1.95 (m, 1H). |

(a) Prepared with the method of Example 44.
(b) Prepared with the method of Example 41.
(c) Prepared with the method of Example 39.

TABLE 3

Examples 84-117

| Ex | Structure | Name | Calc/Obs'd mass (ES+) [M + H]$^+$ |
|---|---|---|---|
| 84 | 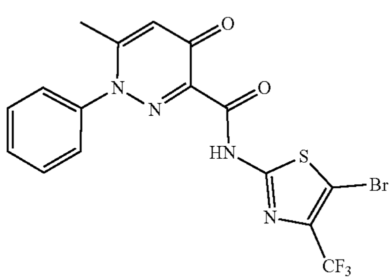 [SMILES: Cc1cc(=O)c(C(=O)Nc2nc(C(F)(F)F)c(Br)s2)nn1-c1ccccc1] | N-(5-bromo-4-(trifluoromethyl)thiazol-2-yl)-6-methyl-4-oxo-1-phenyl-1,4-dihydropyridazine-3-carboxamide | 458/ |

TABLE 3-continued

Examples 84-117

| Ex | Structure | Name | Calc/Obs'd mass (ES+) [M + H]+ |
|---|---|---|---|
| 85 | 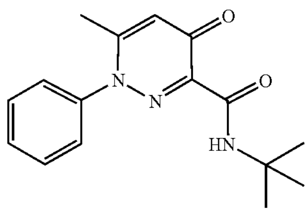 [SMILES: Cc1cc(=O)c(C(=O)NC(C)(C)C)nn1-c1ccccc1] | N-(tert-butyl)-6-methyl-4-oxo-1-phenyl-1,4-dihydropyridazine-3-carboxamide | 285/ |
| 86 | 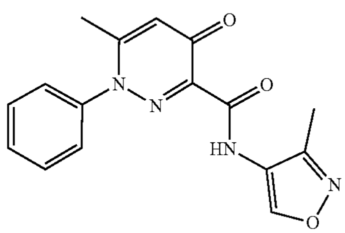 [SMILES: Cc1nocc1NC(=O)c1nn(-c2ccccc2)c(C)cc1=O] | 6-methyl-N-(3-methylisoxazol-4-yl)-4-oxo-1-phenyl-1,4-dihydropyridazine-3-carboxamide | 310/ |
| 87 | 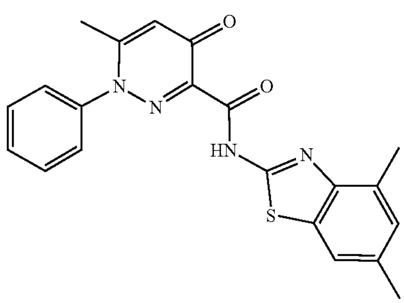 [SMILES: Cc1cc(C)c2nc(NC(=O)c3nn(-c4ccccc4)c(C)cc3=O)sc2c1] | N-(4,6-dimethylbenzo[d]thiazol-2-yl)-6-methyl-4-oxo-1-phenyl-1,4-dihydropyridazine-3-carboxamide | 390/ |
| 88 | 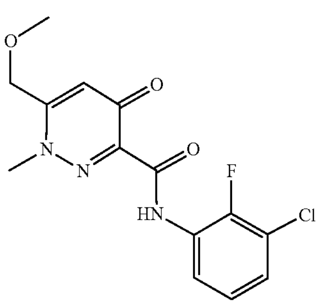 [SMILES: COCc1cc(=O)c(C(=O)Nc2cccc(Cl)c2F)nn1C] | N-(3-chloro-2-fluorophenyl)-6-(methoxymethyl)-1-methyl-4-oxo-1,4-dihydropyridazine-3-carboxamide | 325/ |
| 89 | 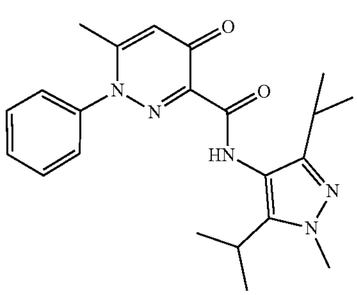 [SMILES: Cc1cc(=O)c(C(=O)Nc2c(C(C)C)nn(C)c2C(C)C)nn1-c1ccccc1] | N-(3,5-diisopropyl-1-methyl-1H-pyrazol-4-yl)-6-methyl-4-oxo-1-phenyl-1,4-dihydropyridazine-3-carboxamide | 393/ |

TABLE 3-continued

Examples 84-117

| Ex | Structure | Name | Calc/Obs'd mass (ES+) [M + H]+ |
|---|---|---|---|
| 90 | 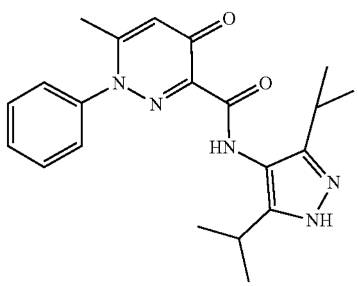 [SMILES: Cc1cc(=O)c(C(=O)Nc2c(C(C)C)n[nH]c2C(C)C)nn1-c1ccccc1] | N-(3,5-diisopropyl-1H-pyrazol-4-yl)-6-methyl-4-oxo-1-phenyl-1,4-dihydropyridazine-3-carboxamide | 379/ |
| 91 | 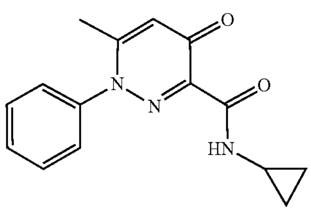 [SMILES: Cc1cc(=O)c(C(=O)NC2CC2)nn1-c1ccccc1] | N-cyclopropyl-6-methyl-4-oxo-1-phenyl-1,4-dihydropyridazine-3-carboxamide | 269/ |
| 92 | 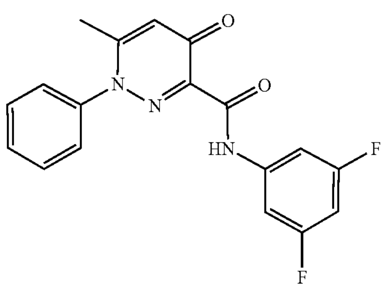 [SMILES: Cc1cc(=O)c(C(=O)Nc2cc(F)cc(F)c2)nn1-c1ccccc1] | N-(3,5-difluorophenyl)-6-methyl-4-oxo-1-phenyl-1,4-dihydropyridazine-3-carboxamide | 341/ |
| 93 | 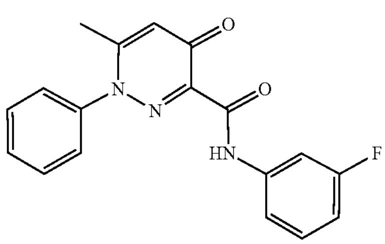 [SMILES: Cc1cc(=O)c(C(=O)Nc2cccc(F)c2)nn1-c1ccccc1] | N-(3-fluorophenyl)-6-methyl-4-oxo-1-phenyl-1,4-dihydropyridazine-3-carboxamide | 323/ |
| 94 | 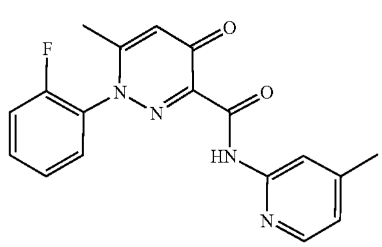 [SMILES: Cc1ccnc(NC(=O)c2nn(-c3ccccc3F)c(C)cc2=O)c1] | 1-(2-fluorophenyl)-6-methyl-N-(4-methylpyridin-2-yl)-4-oxo-1,4-dihydropyridazine-3-carboxamide | 338/ |

TABLE 3-continued

Examples 84-117

| Ex | Structure | Name | Calc/Obs'd mass (ES+) [M + H]+ |
|---|---|---|---|
| 95 | 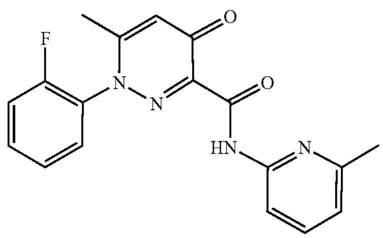 [SMILES: Cc1cccc(NC(=O)c2nn(-c3ccccc3F)c(C)cc2=O)n1] | 1-(2-fluorophenyl)-6-methyl-N-(6-methylpyridin-2-yl)-4-oxo-1,4-dihydropyridazine-3-carboxamide | 338/ |
| 96 | 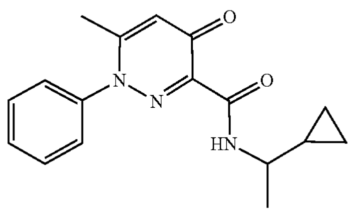 [SMILES: Cc1cc(=O)c(C(=O)NC(C)C2CC2)nn1-c1ccccc1] | N-(1-cyclopropylethyl)-6-methyl-4-oxo-1-phenyl-1,4-dihydropyridazine-3-carboxamide | 297/ |
| 97 | 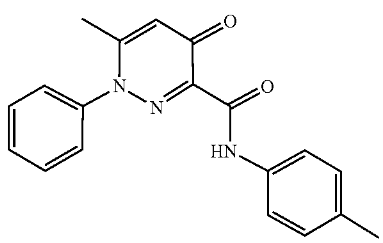 [SMILES: Cc1ccc(NC(=O)c2nn(-c3ccccc3)c(C)cc2=O)cc1] | 6-methyl-4-oxo-1-phenyl-N-(p-tolyl)-1,4-dihydropyridazine-3-carboxamide | 319/ |
| 98 | 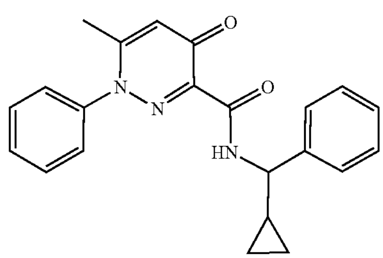 [SMILES: Cc1cc(=O)c(C(=O)NC(c2ccccc2)C2CC2)nn1-c1ccccc1] | N-(cyclopropyl(phenyl)methyl)-6-methyl-4-oxo-1-phenyl-1,4-dihydropyridazine-3-carboxamide | 359/ |
| 99 | 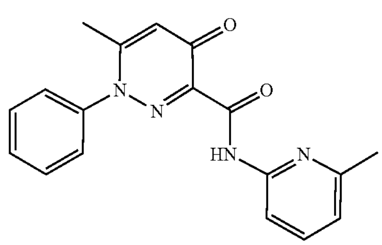 [SMILES: Cc1cccc(NC(=O)c2nn(-c3ccccc3)c(C)cc2=O)n1] | 6-methyl-N-(6-methylpyridin-2-yl)-4-oxo-1-phenyl-1,4-dihydropyridazine-3-carboxamide | 320/ |
| 100 | 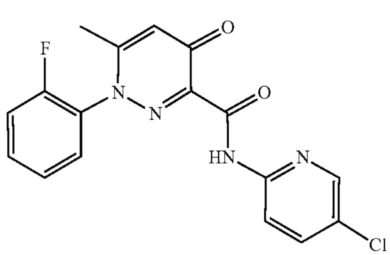 [SMILES: Cc1cc(=O)c(C(=O)Nc2ccc(Cl)cn2)nn1-c1ccccc1F] | N-(5-chloropyridin-2-yl)-1-(2-fluorophenyl)-6-methyl-4-oxo-1,4-dihydropyridazine-3-carboxamide | 358/ |

TABLE 3-continued

Examples 84-117

| Ex | Structure | Name | Calc/Obs'd mass (ES+) [M + H]+ |
|---|---|---|---|
| 101 | 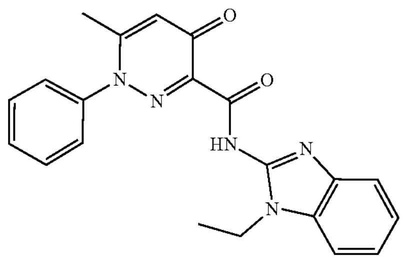 [SMILES: CCn1c(NC(=O)c2nn(-c3ccccc3)c(C)cc2=O)nc2ccccc21] | N-(1-ethyl-1H-benzo[d]imidazol-2-yl)-6-methyl-4-oxo-1-phenyl-1,4-dihydropyridazine-3-carboxamide | 373/ |
| 102 | 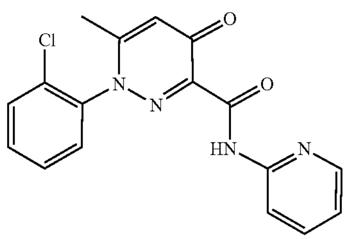 [SMILES: Cc1cc(=O)c(C(=O)Nc2ccccn2)nn1-c1ccccc1Cl] | 1-(2-chlorophenyl)-6-methyl-4-oxo-N-(pyridin-2-yl)-1,4-dihydropyridazine-3-carboxamide | 340/ |
| 103 | 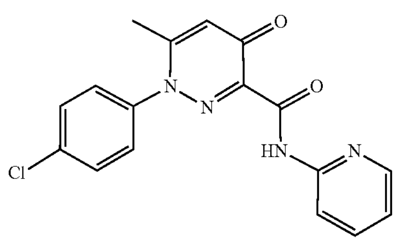 [SMILES: Cc1cc(=O)c(C(=O)Nc2ccccn2)nn1-c1ccc(Cl)cc1] | 1-(4-chlorophenyl)-6-methyl-4-oxo-N-(pyridin-2-yl)-1,4-dihydropyridazine-3-carboxamide | 340/ |
| 104 | 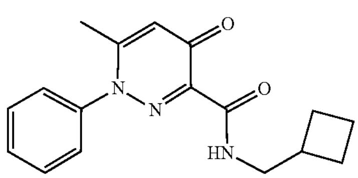 [SMILES: Cc1cc(=O)c(C(=O)NCC2CCC2)nn1-c1ccccc1] | N-(cyclobutylmethyl)-6-methyl-4-oxo-1-phenyl-1,4-dihydropyridazine-3-carboxamide | 297/ |
| 105 | 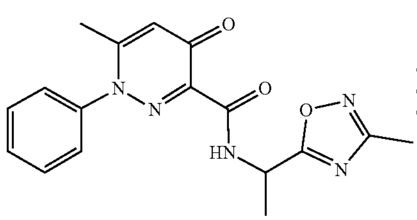 [SMILES: Cc1noc(C(C)NC(=O)c2nn(-c3ccccc3)c(C)cc2=O)n1] | 6-methyl-N-(1-(3-methyl-1,2,4-oxadiazol-5-yl)ethyl)-4-oxo-1-phenyl-1,4-dihydropyridazine-3-carboxamide | 339/ |
| 106 | 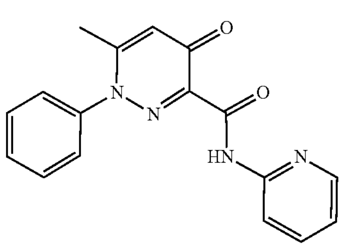 [SMILES: Cc1cc(=O)c(C(=O)Nc2ccccn2)nn1-c1ccccc1] | 6-methyl-4-oxo-1-phenyl-N-(pyridin-2-yl)-1,4-dihydropyridazine-3-carboxamide | 306/ |

TABLE 3-continued

Examples 84-117

| Ex | Structure | Name | Calc/Obs'd mass (ES+) [M + H]+ |
|---|---|---|---|
| 107 | 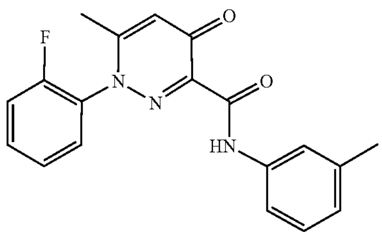 [SMILES: Cc1cccc(NC(=O)c2nn(-c3ccccc3F)c(C)cc2=O)c1] | 1-(2-fluorophenyl)-6-methyl-4-oxo-N-(m-tolyl)-1,4-dihydropyridazine-3-carboxamide | 337/ |
| 108 | 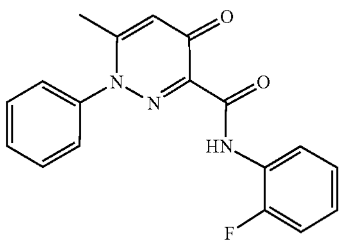 [SMILES: Cc1cc(=O)c(C(=O)Nc2ccccc2F)nn1-c1ccccc1] | N-(2-fluorophenyl)-6-methyl-4-oxo-1-phenyl-1,4-dihydropyridazine-3-carboxamide | 323/ |
| 109 | 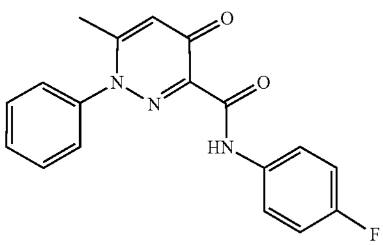 [SMILES: Cc1cc(=O)c(C(=O)Nc2ccc(F)cc2)nn1-c1ccccc1] | N-(4-fluorophenyl)-6-methyl-4-oxo-1-phenyl-1,4-dihydropyridazine-3-carboxamide | 323/ |
| 110 | 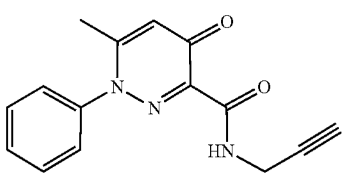 [SMILES: C#CCNC(=O)c1nn(-c2ccccc2)c(C)cc1=O] | 6-methyl-4-oxo-1-phenyl-N-(prop-2-yn-1-yl)-1,4-dihydropyridazine-3-carboxamide | 267/ |
| 111 | 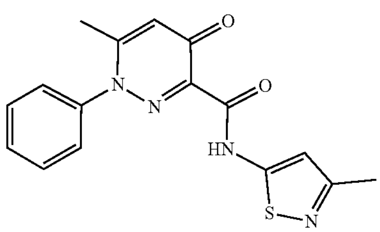 [SMILES: Cc1cc(NC(=O)c2nn(-c3ccccc3)c(C)cc2=O)sn1] | 6-methyl-N-(3-methylisothiazol-5-yl)-4-oxo-1-phenyl-1,4-dihydropyridazine-3-carboxamide | 326/ |
| 112 | 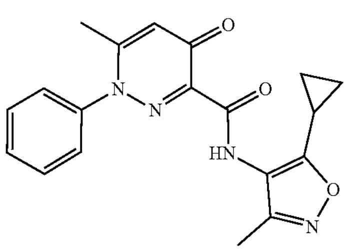 [SMILES: Cc1noc(C2CC2)c1NC(=O)c1nn(-c2ccccc2)c(C)cc1=O] | N-(5-cyclopropyl-3-methylisoxazol-4-yl)-6-methyl-4-oxo-1-phenyl-1,4-dihydropyridazine-3-carboxamide | 350/ |

TABLE 3-continued

Examples 84-117

| Ex | Structure | Name | Calc/Obs'd mass (ES+) [M + H]+ |
|---|---|---|---|
| 113 | 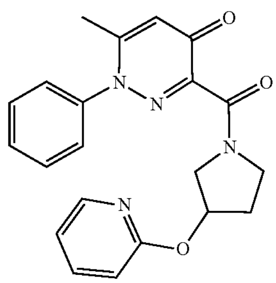 [SMILES: Cc1cc(=O)c(C(=O)N2CCC(Oc3ccccn3)C2)nn1-c1ccccc1] | 6-methyl-1-phenyl-3-(3-(pyridin-2-yloxy)pyrrolidine-1-carbonyl)pyridazin-4(1H)-one | 376/ |
| 114 | 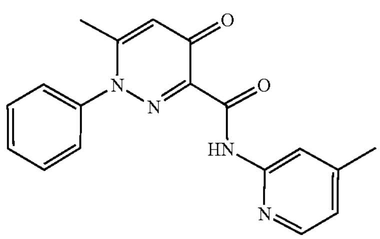 [SMILES: Cc1ccnc(NC(=O)c2nn(-c3ccccc3)c(C)cc2=O)c1] | 6-methyl-N-(4-methylpyridin-2-yl)-4-oxo-1-phenyl-1,4-dihydropyridazine-3-carboxamide | 320/ |
| 115 | 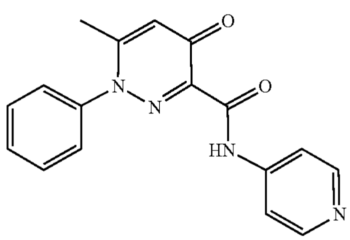 [SMILES: Cc1cc(=O)c(C(=O)Nc2ccncc2)nn1-c1ccccc1] | 6-methyl-4-oxo-1-phenyl-N-(pyridin-4-yl)-1,4-dihydropyridazine-3-carboxamide | 306/ |
| 116 | 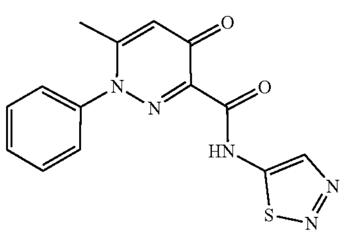 [SMILES: Cc1cc(=O)c(C(=O)Nc2cnns2)nn1-c1ccccc1] | 6-methyl-4-oxo-1-phenyl-N-(1,2,3-thiadiazol-5-yl)-1,4-dihydropyridazine-3-carboxamide | 313/ |
| 117 | 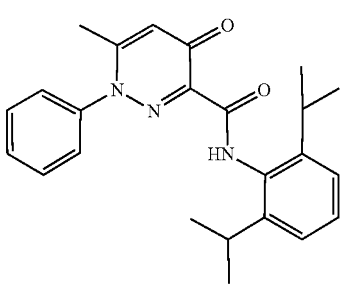 [SMILES: Cc1cc(=O)c(C(=O)Nc2c(C(C)C)cccc2C(C)C)nn1-c1ccccc1] | N-(2,6-diisopropylphenyl)-6-methyl-4-oxo-1-phenyl-1,4-dihydropyridazine-3-carboxamide | 389/ |

The following compounds can generally be made using the methods described above. It is expected that these compounds when made will have activity similar to those that have been made in the examples above.

| Structure | Name | Formula/Exact Mass |
|---|---|---|
| 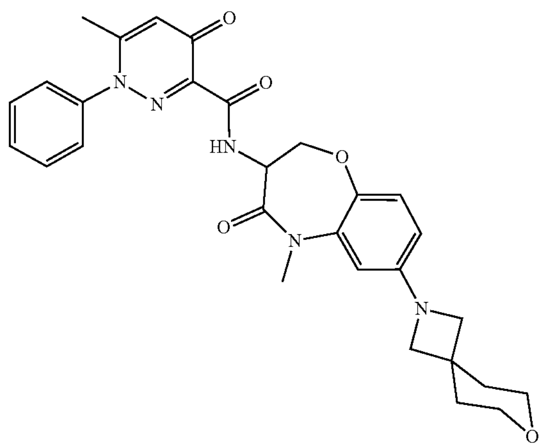 [SMILES: Cc1cc(=O)c(C(=O)NC2COc3ccc(N4CC5(CCOCC5)C4)cc3N(C)C2=O)nn1-c1ccccc1] | 6-methyl-N-(5-methyl-4-oxo-7-(7-oxa-2-azaspiro-[3.5]nonan-2-yl)-2,3,4,5-tetrahydrobenzo[b][1,4]-oxazepin-3-yl)-4-oxo-1-phenyl-1,4-dihydropyridazine-3-carboxamide | $C_{29}H_{31}N_5O_5$/ 529.23 |
| | N-(7-((5,6-dihydro-[1,2,4]triazolo[1,5-a]pyrazin-7(8H)-yl)methyl)-5-methyl-4-oxo-2,3,4,5-tetrahydro-benzo[b][1,4]oxazepin-3-yl)-6-methyl-4-oxo-1-phenyl-1,4-dihydropyridazine-3-carboxamide | $C_{28}H_{28}N_8O_4$/ 540.22 |
| 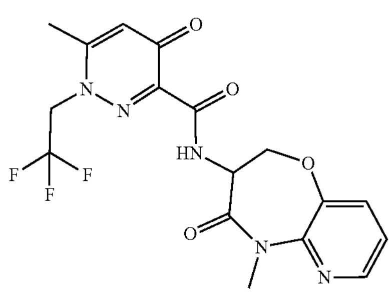 [SMILES: Cc1cc(=O)c(C(=O)NC2COc3cccnc3N(C)C2=O)nn1CC(F)(F)F] | 6-methyl-N-(5-methyl-4-oxo-2,3,4,5-tetrahydropyrido[3,2-b][1,4]oxazepin-3-yl)-4-oxo-1-(2,2,2-trifluoroethyl)-1,4-dihydropyridazine-3-carboxamide | $C_{17}H_{16}F_3N_5O_4$/ 411.12 |
| | 6-methyl-N-(5-methyl-4-oxo-2,3,4,5-tetrahydropyrido[3,2-b][1,4]oxazepin-3-yl)-4-oxo-1-(2,2,3,3,3-pentafluoropropyl)-1,4-dihydropyridazine-3-carboxamide | $C_{18}H_{16}F_5N_5O_4$/ 461.11 |

The activity of the compounds in Examples 1-116 as RIPK1 inhibitors is illustrated in the following assays.

Biological Activity Assays

Compounds described herein have been shown to bind RIPK1 in vitro, and to inhibit phosphorylation of a downstream molecular target in a cellular assay.

ADP-Glo Kinase Assay

In order to measure RIPK1 activity the ADP-Glo kinase assay (Promega, Catalog #V7002) was used to measure the conversion of ATP to ADP. This enzymatic assay was performed in a 384-well white, Optiplate (Perkin Elmer, Catalog #6007299) with assay buffer consisting of 50 mM HEPES pH 7.5 (Gibco, Catalog #15630-080), 50 mM NaCl (Teknova, Catalog #S0252), 30 mM $MgCl_2$ (Ambion, Catalog #AM9530G), 1 mM DTT (Santa Cruz Biotechnology, Catalog #sc-29089), 0.05% BSA (Sigma, Catalog #A3059-50G) and 0.02% CHAPS (Sigma, Catalog #C5070-5G). Stock solutions of the test compounds were prepared in 100% DMSO (Sigma, Catalog #D2650) and serially diluted 1:3 using 100% DMSO. Compounds were additionally diluted 1:40 in assay buffer, and 2 μL/well were transferred to the assay plate. 4 μL/well (final concentration of 5 nM) of RIPK1 protein (SignalChem, Catalog #R07-11G-05) diluted in assay buffer and added to the assay plate followed by a 10 minute preincutation at room temperature. 4 μL/well of ATP (Promega, Catalog #V7002) (final concentration of 50 μM) diluted in assay buffer were then added to the assay plate followed by a 6 hr reaction time. Final concentrations of RIPK1 and ATP refer to a 10 μL volume. Luminescence was measured using a BioTek Synergy™ NEO plate reader. $IC_{50}$ values were calculated using a four-parameter logistic curve fit using Genedata Screener software. Results are shown below in Table 4, where the average value across multiple runs is given.

TABLE 4

| RIPK1 activity | |
| --- | --- |
| Ex | RIPK1 $IC_{50}$ (nM) |
| 1 | 32 |
| 2 | 823 |
| 3 | 10238 |
| 4 | 80 |
| 5 | 1781 |
| 6 | N/A |
| 7 | 1600 |
| 8 | 53 |
| 9 | 78 |
| 10 | 390 |
| 11 | 15375 |
| 12 | 1178 |
| 13 | 7924 |
| 14 | 4614 |
| 15 | 13637 |
| 16 | 4403 |
| 17 | 52 |
| 18 | 4708 |
| 19 | 12646 |
| 20 | 4457 |
| 21 | 636 |
| 22 | 1497 |
| 23 | 1142 |
| 24 | 489 |
| 25 | 3867 |
| 26 | 668 |
| 27 | 1459 |
| 28 | 2681 |
| 29 | 1145 |
| 30 | 15547 |
| 31 | 519 |
| 32 | 2248 |
| 33 | 2190 |
| 34 | 3912 |
| 35 | 1775 |
| 38 | 57 |
| 39 | 18 |
| 40 | 36 |
| 41 | 35 |
| 42 | 36 |
| 43 | 23 |
| 44 | 62 |
| 45 | 28 |
| 46 | 1444 |
| 47 | 72 |
| 48 | 51 |
| 49 | 64 |
| 50 | 28 |
| 51 | 1971 |
| 52 | 37 |
| 53 | 652 |
| 54 | 27 |
| 55 | 33 |
| 56 | 85 |
| 57 | 20 |
| 59 | 33.5 |
| 60 | 84.9 |
| 61 | 57.4 |
| 62 | 48.0 |
| 64 | 43.1 |
| 65 | 47.6 |
| 66 | 30.2 |
| 67 | 68.2 |
| 68 | 57.8 |
| 69 | 8500 |
| 70 | 28.9 |
| 71 | 30.9 |
| 72 | 90.6 |
| 84 | 33334 |
| 85 | 38778 |
| 86 | 17598 |
| 87 | 20777 |
| 88 | 33334 |
| 89 | 18580 |
| 90 | 41898 |
| 91 | 5306 |
| 92 | 414 |
| 93 | 282 |
| 94 | 6350 |
| 95 | 3939 |
| 96 | 6490 |
| 97 | 11629 |
| 98 | 3567 |
| 99 | 3489 |
| 100 | 43838 |
| 101 | 4638 |
| 102 | 2374 |
| 103 | 5000 |
| 104 | 8254 |
| 105 | 36852 |
| 106 | 1784 |
| 107 | 20229 |
| 108 | 28716 |
| 109 | 28100 |
| 110 | 1594 |
| 111 | 39082 |
| 112 | 791 |
| 113 | 29491 |
| 114 | 5599 |
| 114 | 7501 |

TABLE 4-continued

RIPK1 activity

| Ex | RIPK1 IC$_{50}$ (nM) |
|---|---|
| 115 | 2917 |
| 115 | 3473 |
| 116 | 8517 |
| 116 | 17387 |
| 117 | 1192 |

Human U937 Cellular Necroptosis Assay

The human monocytic cell line U937 (CRL-1593.2) was purchased from ATCC. The cells were routinely maintained in RPMI-1640 Medium (Gibco, Catalog #11875-093) supplemented with 10% heat inactivated fetal bovine serum (Gibco, Catalog #16140-071), 100 units/mL penicillin and 100 µg/mL streptomycin (Gibco, Catalog #15140-122), in a humidified incubator (37° C., 5% CO$_2$). For the assay, cells were resuspended in RPMI-1640 phenol red free Media (Gibco, Catalog #11835-030) supplemented with 10% fetal bovine serum (Sigma, Catalog #F2442), 100 units/mL penicillin and 100 ug/mL streptomycin. Cells were stimulated with 25 ng/mL human TNFalpha (Cell Sciences, Catalog #CSI15659B) and 25 µM z-VAD-FMK (R&D Systems, Catalog #FMK001) followed by seeding 5000 cells per well in a volume of 40 µL to a white, CulturPlate-384 (Perkin Elmer, Catalog #6007680). Stock solutions of the test compounds were prepared in 100% DMSO (Sigma, Catalog #D2650) and serially diluted 1:3 using 100% DMSO. Compounds were additionally diluted 1:40 in assay medium, and 10 µL/well was transferred to the plate. Following the compound addition the plate was incubated at 37° C. and 5% CO$_2$ for 22 hr. After 22 hr, viability was assessed with the addition of 20 µL of Cell Titer-Glo 2.0 (Promega, Catalog #G9243). The tissue culture plate was shaken on an orbital shaker at 300 RPM for 15 minutes at room temperature in the dark. Luminescence was measured using a PerkinElmer Envision™ plate reader. IC$_{50}$ values were calculated using a four-parameter logistic curve fit using Genedata Screener software. Results are shown below in Table 5, where the average value across multiple runs is given.

TABLE 5 hU937 activity

| Ex | hU937 IC$_{50}$ (nM) |
|---|---|
| 1 | 136 |
| 8 | 172 |
| 9 | 170 |
| 17 | 631 |
| 24 | 2659 |
| 26 | 3173 |
| 32 | 5825 |
| 33 | 8491 |
| 38 | 82 |
| 39 | 69 |
| 40 | 47 |
| 41 | 39 |
| 42 | 141 |
| 43 | 48 |
| 44 | 160 |
| 45 | 72 |
| 47 | 86 |
| 48 | 70 |
| 49 | 66 |
| 50 | 33 |
| 51 | 1699 |
| 53 | 591 |
| 54 | 53 |
| 55 | 54 |
| 56 | 292 |
| 57 | 41 |
| 59 | 74 |
| 60 | 424 |
| 61 | 88 |
| 62 | 67 |
| 63 | 478.7 |
| 64 | 77.8 |
| 65 | 123.7 |
| 66 | 80.4 |
| 67 | 281.4 |
| 68 | 142.5 |
| 69 | 10000 |
| 70 | 227.2 |
| 71 | 50.2 |
| 72 | 222.3 |
| 73 | 295.9 |
| 74 | 58.2 |
| 75 | 28.4 |
| 76 | 5589 |
| 77 | 26.5 |
| 78 | 150.2 |
| 79 | 507.4 |
| 80 | 3710 |
| 81 | 788.2 |
| 82 | 56.4 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula I:

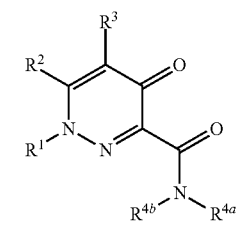

(I)

or a salt thereof, wherein:
$R^1$ is chosen from alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^5$;
$R^2$ is chosen from H, alkyl, haloalkyl, and (alkoxy)alkyl;
$R^3$ is chosen from H, CN, halo, alkyl, and alkoxy;
or $R^2$ and $R^3$, together with the intervening atoms, combine to form a 5-, 6-, or 7-membered cycloalkyl, heterocycloalkyl, aryl, or heteroaryl;
$R^{4a}$ is H;

$R^{4b}$ is chosen from

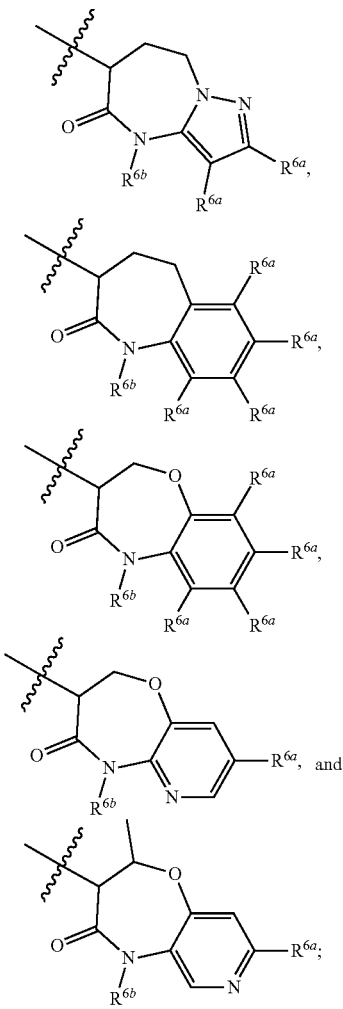

each $R^5$ is independently chosen from CN, halo, hydroxy, oxo, alkyl, and (alkyl)oxy; and
each $R^{6a}$ is independently chosen from H, CN, halo, hydroxy, oxo, $C_{1-6}$alkyl, halo$C_{1-6}$alkyl, $C_{3-7}$ cycloalkyl, 4- to 11-membered heterocycloalkyl, $C_{6-10}$aryl, 5- to 10-membered heteroaryl, ($C_{2-6}$alkenyl)$C_{1-6}$alkyl, ($C_{2-6}$alkynyl)$C_{1-6}$alkyl, ($C_{3-7}$cycloalkyl)$C_{1-6}$alkyl, (4- to 11-membered heterocycloalkyl)$C_{1-6}$alkyl, ($C_{6-10}$aryl)$C_{1-6}$alkyl, (5- to 10-membered heteroaryl)$C_{1-6}$alkyl, ($C_{1-6}$ alkyl)oxy, ($C_{3-7}$cycloalkyl)oxy, (4- to 11-membered heterocycloalkyl)oxy, ($C_{6-10}$aryl)oxy, and (5- to 10-membered heteroaryl)oxy; and
$R^{6b}$ is chosen from H and $C_{1-6}$alkyl.

2. A compound as recited in claim 1, or a salt thereof, wherein $R^1$ is chosen from phenyl, pyridyl, pyridazinyl, pyrimidinyl, pyrazinyl, (phenyl)methyl, (pyridyl)methyl, (pyridazinyl)methyl, (pyrimidinyl)methyl, and (pyrazinyl)methyl, any one of which is optionally substituted with 1, 2, or 3 $R^5$.

3. A compound as recited in claim 2, or a salt thereof, wherein $R^1$ is chosen from phenyl, pyridyl, (phenyl)methyl, and (pyridyl)methyl, any one of which is optionally substituted with 1 or 2 $R^5$.

4. A compound as recited in claim 3, or a salt thereof, wherein each $R^5$ is independently chosen from CN, F, Cl, Br, hydroxy, methyl, and methoxy.

5. A compound as recited in claim 4, or a salt thereof, wherein $R^3$ is H.

6. A compound of structural Formula IV:

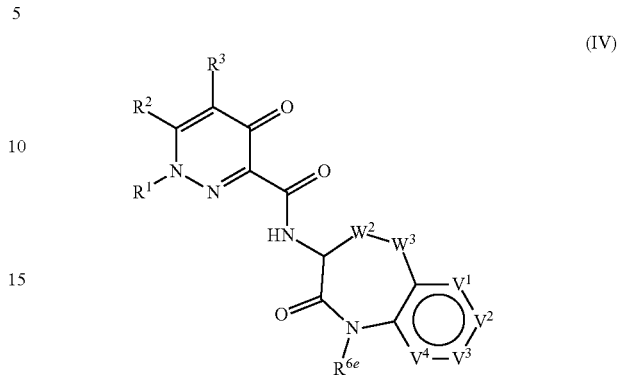

(IV)

or a salt thereof, wherein:
$R^1$ is chosen from alkyl, cycloalkyl, heterocycloalkyl, aryl, heteroaryl, (cycloalkyl)alkyl, (heterocycloalkyl)alkyl, (aryl)alkyl, and (heteroaryl)alkyl, any one of which is optionally substituted with one or more $R^5$;
$R^2$ is chosen from H, alkyl, haloalkyl, and (alkoxy)alkyl;
$R^3$ is chosen from H, CN, halo, alkyl, and alkoxy;
or $R^2$ and $R^3$, together with the intervening atoms, combine to form a 5-, 6-, or 7-membered cycloalkyl, heterocycloalkyl, aryl, or heteroaryl;
$V^1$ is chosen from a bond, $CR^{6g}$, N, $NR^{6g}$, O, and S;
$V^2$, $V^3$, and $V^4$ are independently chosen from $CR^{6g}$, N, $NR^{6g}$, O, and S;
$V^1$, $V^2$, $V^3$, and $V^4$, together with the intervening two carbons, combine to form a 5- or 6-membered aryl or heteroaryl;
$W^2$ is chosen from a bond and $CHR^{6g}$;
$W^3$ is chosen from a bond, $CHR^{6g}$, $NR^{6g}$, O, and S;
if $W^2$ is a bond, then $W^3$ is $CHR^{6g}$;
each $R^5$ is independently chosen from CN, halo, hydroxy, oxo, alkyl, and (alkyl)oxy;
$R^{6e}$ is chosen from H, alkyl, and cycloalkyl; and
each $R^{6g}$ is independently chosen from H, CN, halo, hydroxy, oxo, alkyl, cycloalkyl, heterocycloalkyl, (cycloalkyl)alkyl, (heterocycloalkyl)alkyl, aryl, and heteroaryl.

7. A compound as recited in claim 6, or a salt thereof, wherein:
$V^1$, $V^2$, $V^3$, and $V^4$ are independently chosen from $CR^{6g}$ and N; and
$V^1$, $V^2$, $V^3$, and $V^4$, together with the intervening two carbons, combine to form phenyl or a 6-membered heteroaryl.

8. A compound as recited in claim 7, or a salt thereof, wherein at most one of $V^1$, $V^2$, $V^3$, and $V^4$ is N.

9. A compound as recited in claim 8, or a salt thereof, wherein:
$V^1$, $V^2$, $V^3$, and $V^4$ are $CR^{6g}$; and
$V^1$, $V^2$, $V^3$, and $V^4$, together with the intervening two carbons, combine to form phenyl.

10. A compound as recited in claim 9, or a salt thereof, wherein each $R^{6g}$ is independently chosen from H, CN, and halo.

11. A compound as recited in claim 1, chosen from
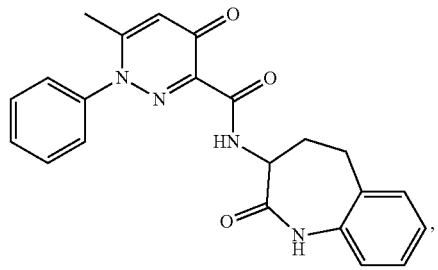
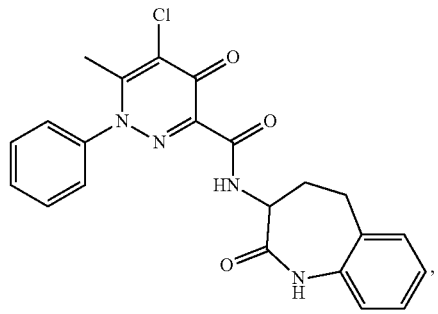
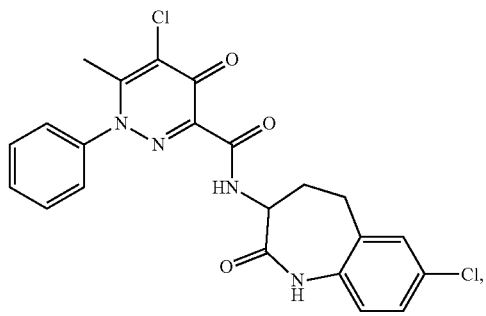
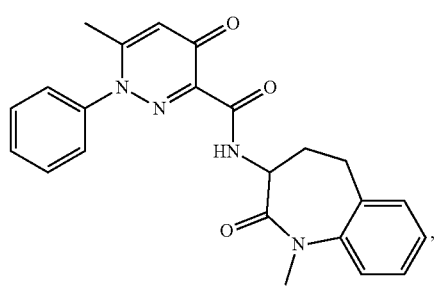
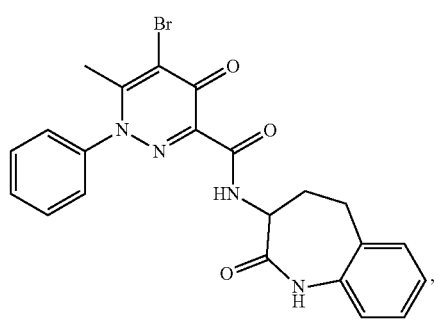
-continued
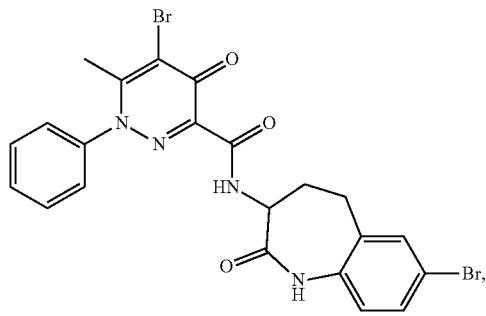
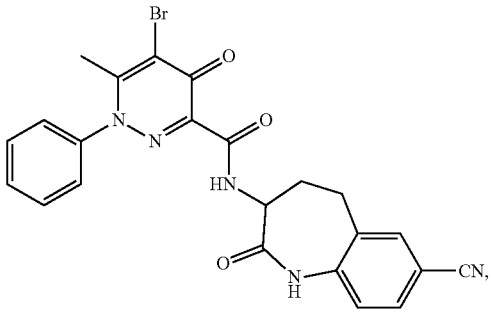
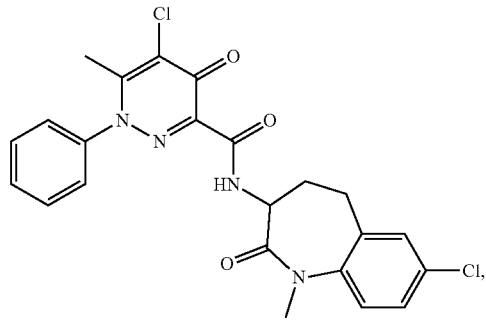
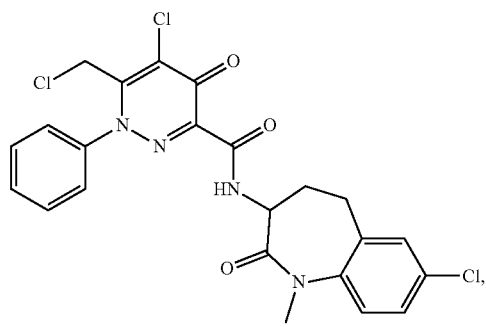
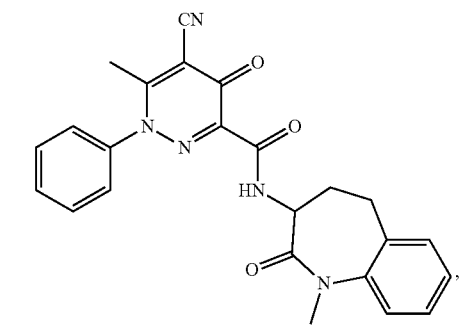

151
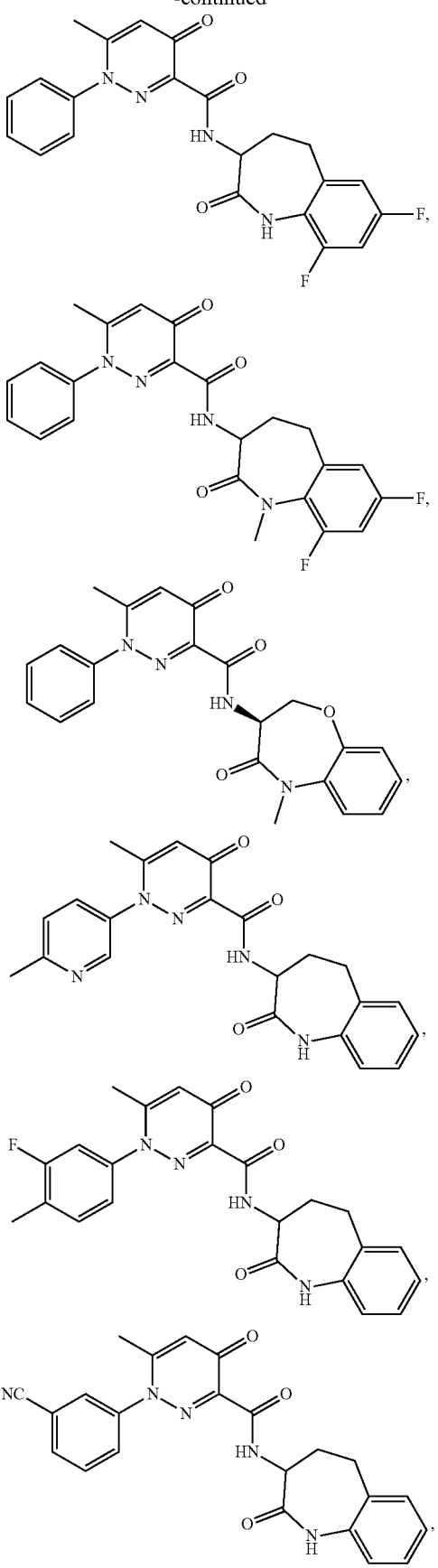
152
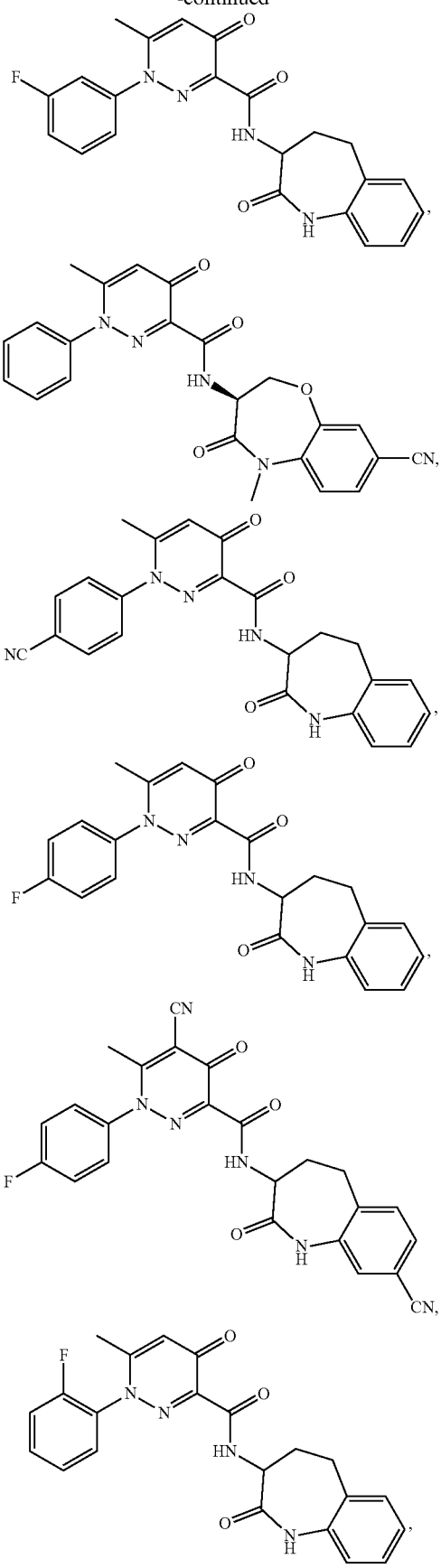

153
-continued
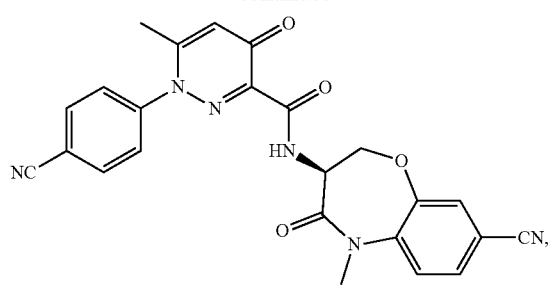
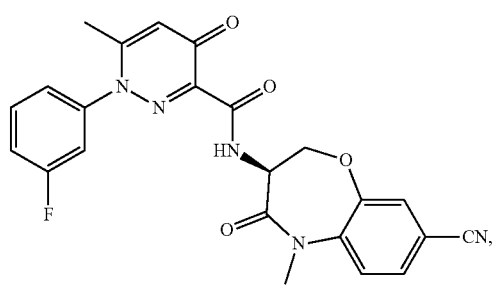
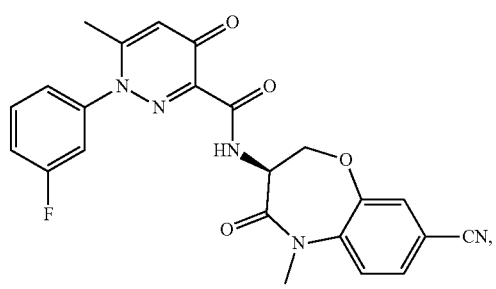
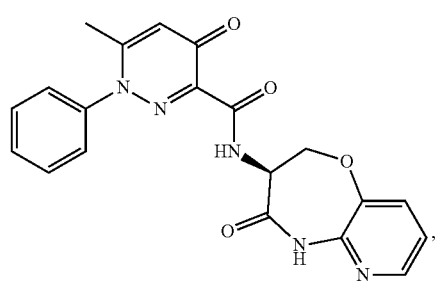
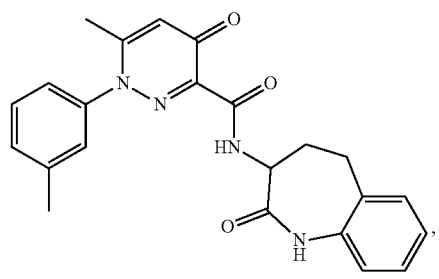
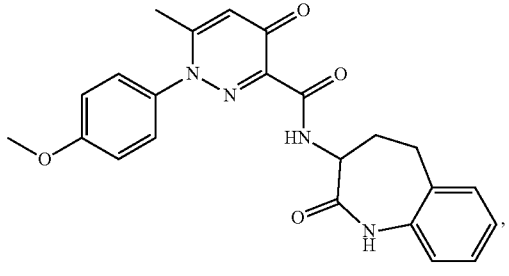
154
-continued
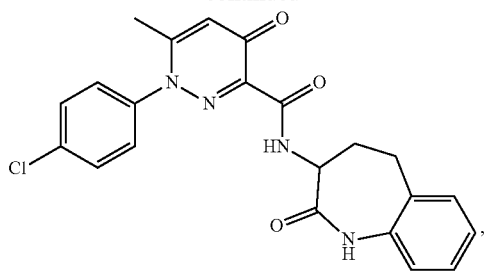
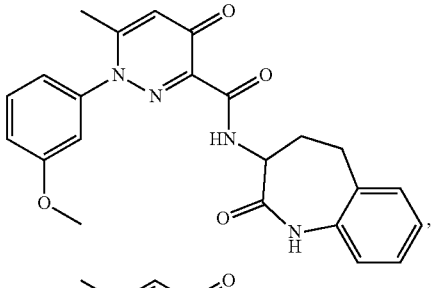
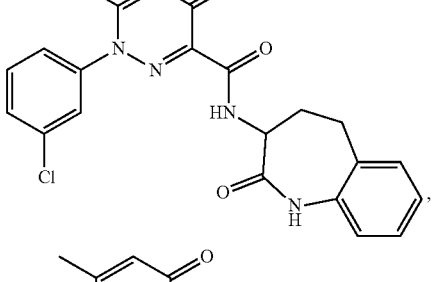
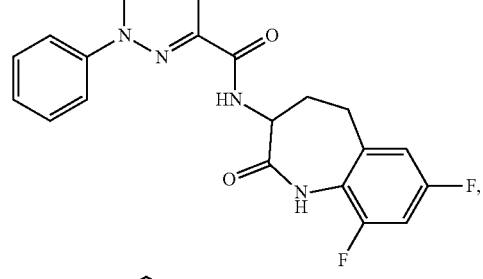
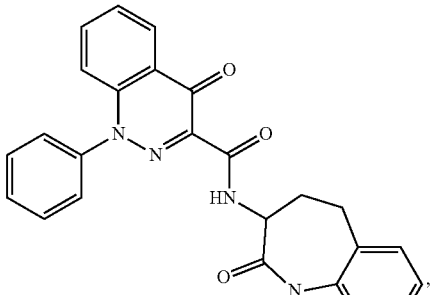
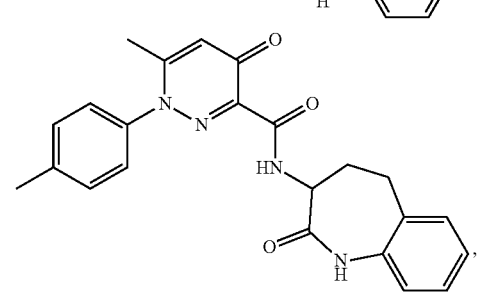

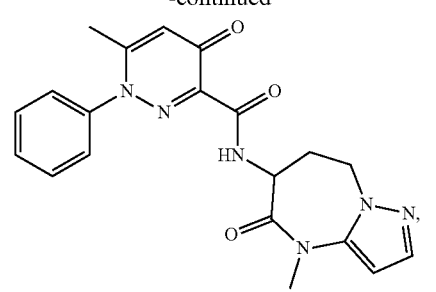
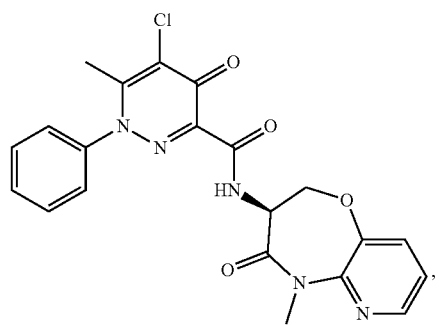
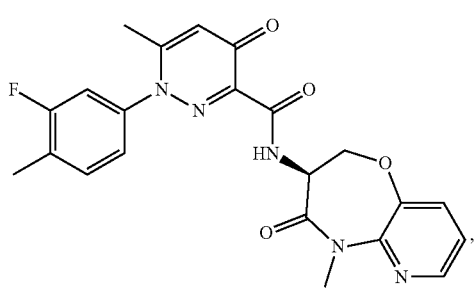
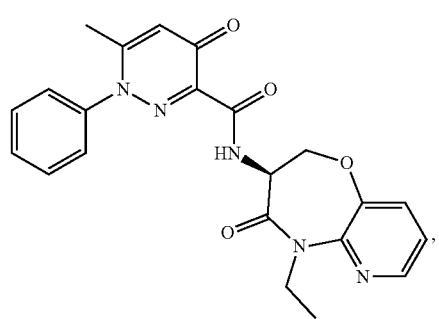
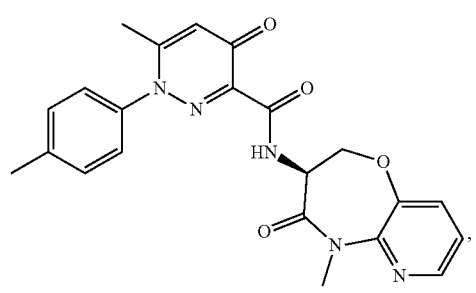
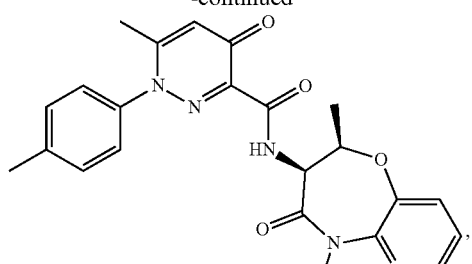
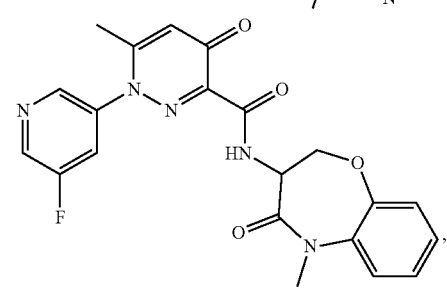
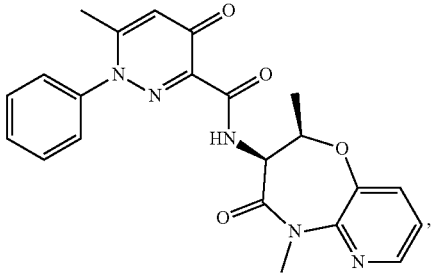
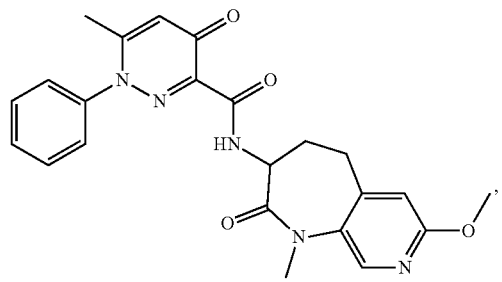
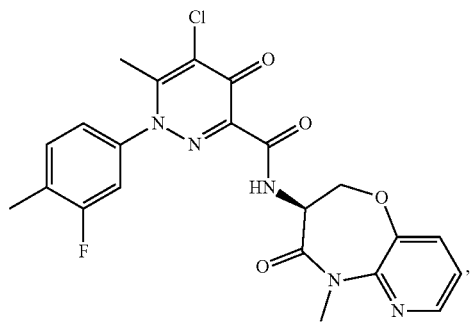
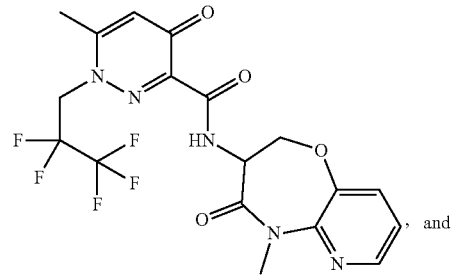

-continued

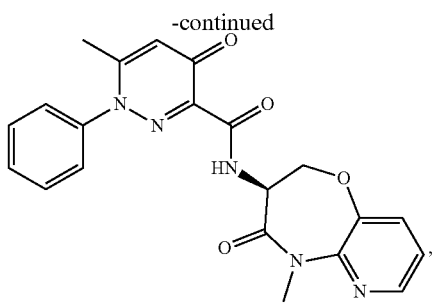

12. A pharmaceutical composition comprising a compound as recited in claim 6, or a salt thereof, together with a pharmaceutically acceptable carrier.

13. A method of inhibition of RIPK1 comprising contacting RIPK1 with a compound as recited in claim 1, or a salt thereof.

14. A method of treatment of a RIPK1-mediated disease comprising the administration of a therapeutically effective amount of a compound as recited in claim 1, or a salt thereof, to a patient in need thereof.

15. The method as recited in claim 14, wherein said disease is a neurological disease.

16. The method as recited in claim 14, wherein said disease is a retinal disease.

17. The method as recited in claim 14, wherein said disease is an autoimmune disorder.

18. The method as recited in claim 14, wherein said disease is an inflammatory disease.

19. The method as recited in claim 14, wherein said disease is cancer.

20. A method of treatment of injury to the CNS comprising the administration of a therapeutically effective amount of a compound as recited in claim 1, or a salt thereof, to a patient in need thereof.

21. A method of treatment of a RIPK1-mediated disease comprising the administration of:
   a. a therapeutically effective amount of a compound as recited in claim 1, or a salt thereof; and
   b. another therapeutic agent.

22. The method as recited in claim 21, wherein the disease is cancer.

23. The method as recited in claim 22, wherein the other therapeutic agent is a checkpoint inhibitor.

24. The method as recited in claim 23, wherein the checkpoint inhibitor is chosen from an anti-PD1 inhibitor, an anti-PDL1 inhibitor, an anti-CTLA4 inhibitor, an anti-OX50 inhibitor, an anti-TIM3 inhibitor, and an anti-LAG3 inhibitor.

* * * * *